(12) United States Patent
Domon et al.

(10) Patent No.: US 9,645,493 B2
(45) Date of Patent: May 9, 2017

(54) NEGATIVE RESIST COMPOSITION AND PATTERN FORMING PROCESS

(71) Applicant: Shin-Etsu Chemical Co., Ltd., Tokyo (JP)

(72) Inventors: Daisuke Domon, Joetsu (JP); Keiichi Masunaga, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/091,092

(22) Filed: Apr. 5, 2016

(65) Prior Publication Data

US 2016/0299430 A1  Oct. 13, 2016

(30) Foreign Application Priority Data

Apr. 7, 2015 (JP) ................. 2015-078433
Apr. 8, 2015 (JP) ................. 2015-078904

(51) Int. Cl.

| *G03F 7/004* | (2006.01) |
| *G03F 7/038* | (2006.01) |
| *C08F 220/18* | (2006.01) |
| *C07C 381/12* | (2006.01) |
| *C08F 220/24* | (2006.01) |
| *C08F 220/30* | (2006.01) |
| *G03F 1/76* | (2012.01) |
| *G03F 1/78* | (2012.01) |
| *G03F 7/20* | (2006.01) |
| *G03F 7/32* | (2006.01) |

(52) U.S. Cl.
CPC ............ *G03F 7/038* (2013.01); *C07C 381/12* (2013.01); *C08F 220/18* (2013.01); *C08F 220/24* (2013.01); *C08F 220/30* (2013.01); *G03F 1/76* (2013.01); *G03F 1/78* (2013.01); *G03F 7/0045* (2013.01); *G03F 7/0046* (2013.01); *G03F 7/0382* (2013.01); *G03F 7/20* (2013.01); *G03F 7/2004* (2013.01); *G03F 7/2059* (2013.01); *G03F 7/327* (2013.01)

(58) Field of Classification Search
CPC ...... G03F 7/004; G03F 7/0045; G03F 7/0046; G03F 7/0382; G03F 7/20; C08F 220/24; C08F 220/30; C08F 220/18; C07C 381/12
USPC ........ 430/5, 270.1, 927, 942, 322, 325, 329; 526/243, 319, 326, 281
See application file for complete search history.

(56) References Cited

U.S. PATENT DOCUMENTS

| 5,286,600 | A | 2/1994 | Ochiai et al. |
| 5,618,892 | A | 4/1997 | Furihata et al. |
| 6,506,534 | B1 | 1/2003 | Nozaki et al. |
| 7,300,739 | B2 | 11/2007 | Allen et al. |
| 7,393,624 | B2 | 7/2008 | Allen et al. |
| 7,563,558 | B2 | 7/2009 | Allen et al. |
| 7,977,027 | B2 | 7/2011 | Takeda et al. |
| 8,168,367 | B2 | 5/2012 | Watanabe et al. |
| 8,343,694 | B2 | 1/2013 | Koitabashi et al. |
| 8,361,692 | B2 | 1/2013 | Tanaka et al. |
| 8,426,109 | B2 * | 4/2013 | Kanda .................. G03F 7/0045 430/270.1 |
| 8,815,491 | B2 * | 8/2014 | Masunaga ............. G03F 7/0045 430/270.1 |
| 8,828,643 | B2 * | 9/2014 | Kobayashi ............ G03F 7/0045 430/270.1 |
| 9,023,587 | B2 * | 5/2015 | Hatakeyama ........... G03F 7/322 430/270.1 |
| 9,075,306 | B2 | 7/2015 | Takeda et al. |
| 9,182,670 | B2 * | 11/2015 | Masunaga ............. G03F 7/0045 |
| 9,188,865 | B2 * | 11/2015 | Yokokawa ............ G03F 7/0392 |
| 9,244,347 | B2 * | 1/2016 | Komuro ................ C07C 381/12 |
| 9,250,522 | B2 * | 2/2016 | Hatakeyama ......... G03F 7/0397 |
| 9,316,912 | B2 * | 4/2016 | Kobayashi ............. C07C 69/54 |
| 9,316,915 | B2 * | 4/2016 | Hatakeyama ......... G03F 7/2037 |
| 9,335,632 | B2 * | 5/2016 | Hatakeyama .......... G03F 7/039 |
| 2011/0287234 | A1 * | 11/2011 | Tsuchihashi ............ G03F 7/325 428/195.1 |
| 2013/0209922 | A1 | 8/2013 | Masunaga et al. |
| 2014/0212810 | A1 | 7/2014 | Hatakeyama et al. |

FOREIGN PATENT DOCUMENTS

| EP | 2 626 743 A1 | 8/2013 |
| JP | 6-232702 A | 9/1993 |
| JP | 8-202037 A | 8/1996 |
| JP | 2001-154357 A | 6/2001 |
| JP | 2001-226430 A | 8/2001 |
| JP | 2003-337414 A | 11/2003 |
| JP | 2008-102383 A | 5/2008 |
| JP | 2008-249762 A | 10/2008 |

(Continued)

OTHER PUBLICATIONS

Machine translation of JP 2008-249951 (no date).*
Machine translation of JP 2013-164588 (no date).*
Ito et al., "Negative Resist Compositions", IBM Technical Disclosure Bulletin, vol. 35, No. 1B, p. 397, Jun. 1992, (1 page).
Ito et al., "Acid-Catalyzed Dehydration A New Mechanism for Chemically Amplified Lithographic Imaging", American Chemical Society, Chapter 5, pp. 64-87, 1994, (24 pages).
Yoshida et al., "Cationic chemistry and chemically amplified resist materials for microlithography: synthesis and applications of copolymers of 4-(1-hydroxy-1-methylethyl) styrene and styrene or 4-hydroxystyrene", Polymer, vol. 35, No. 1, pp. 5-13, 1994, (9 pages).
Office Action dated Dec. 21, 2016, issued in counterpart Taiwanese Application No. 105110679. (4 pages).

*Primary Examiner* — Amanda C Walke
(74) *Attorney, Agent, or Firm* — Westerman, Hattori, Daniels & Adrian, LLP

(57) ABSTRACT

A negative resist composition is provided comprising (A) a polymer comprising recurring units having an acid-eliminatable group and recurring units capable of generating acid upon exposure and (B) a carboxylic acid onium salt. When the negative resist composition is processed by the microprocessing technology, especially EB lithography, it forms a pattern having a very high resolution and minimal LER.

11 Claims, No Drawings

(56) References Cited

FOREIGN PATENT DOCUMENTS

| | | | |
|---|---|---|---|
| JP | 2008249951 A | * | 10/2008 |
| JP | 2008-304590 A | | 12/2008 |
| JP | 2010-164933 A | | 7/2010 |
| JP | 2010-276910 A | | 12/2010 |
| JP | 2013-164588 A | | 8/2013 |
| TW | 201439679 A | | 10/2014 |

* cited by examiner

NEGATIVE RESIST COMPOSITION AND PATTERN FORMING PROCESS

CROSS-REFERENCE TO RELATED APPLICATION

This non-provisional application claims priority under 35 U.S.C. §119(a) on Patent Application Nos. 2015-078433 and 2015-078904 filed in Japan on Apr. 7, 2015 and Apr. 8, 2015, respectively, the entire contents of which are hereby incorporated by reference.

TECHNICAL FIELD

This invention relates to a negative resist composition, more particularly a chemically amplified negative resist composition comprising a polymer having a polarity switch function, best suited for the microprocessing of semiconductor substrates and photomask substrates, and a pattern forming process using the composition.

BACKGROUND ART

As is well known in the art, it is required to reduce the pattern rule so as to comply with the recent demand for higher integration densities and operating speeds in LSI devices. Accordingly the exposure method and resist composition have noticeably changed. Particularly in the lithography process of forming patterns with a feature size of 0.2 μm or less, the exposure light is switched to KrF or ArF excimer laser radiation or electron beam, and the photoresist composition is changed to a chemically amplified resist composition having a good sensitivity to such high-energy radiation and a high resolution.

Resist compositions include positive tone compositions wherein the exposed region is dissolved and negative tone compositions wherein the exposed region is left as a pattern. Either one is selected in accordance with the desired resist pattern, depending on ease of processing. The chemically amplified negative resist composition generally comprises a polymer which is soluble in aqueous alkaline developer, an acid generator which is decomposed to generate an acid upon exposure to radiation, and a crosslinker which forms crosslinks between polymer molecules under the catalysis of the acid to turn the polymer insoluble in the developer (sometimes, the polymer and the crosslinker are integrated together). Further a basic compound for controlling diffusion of the acid generated upon exposure is added.

Among negative resist compositions comprising the polymer which is soluble in aqueous alkaline developer, a number of negative resist compositions based on polymers using phenol units as the alkali-soluble unit were developed as best suited for the KrF excimer laser lithography. These compositions were not used in the ArF excimer laser lithography because phenol units have little or no transmittance to exposure light having a wavelength of 150 to 220 nm. Recently a highlight is drawn to these compositions again as the negative resist for the EB or EUV lithography capable of forming finer size patterns. For example, Patent Documents 1 to 3 disclose resist compositions which exhibit a very high resolution even when used in thin film form.

Beside the above-mentioned compositions, many other chemically amplified negative resist compositions have been developed. These negative working resist compositions use a crosslinker for insolubilizing the alkali-soluble polymer under the action of an acid generated upon exposure to high-energy radiation. Many crosslinkers including those disclosed in Patent Documents 1 to 3 have been developed. On the other hand, an attempt has been made to endow the polymer with the function of crosslinker. For example, it was proposed to introduce styrene units having an alkoxymethoxy group substituted thereon (Patent Document 4), recurring units having an alkoxymethylaraino group (Patent Document 5), recurring units having an epoxy group (Patent Document 6), recurring units of styrene having an acid-eliminatable group (Patent Document 7), recurring units of adamantyl having an acid-eliminatable hydroxyl group (Patent Document 8), and recurring units of aliphatic hydrocarbon and alicyclic hydrocarbon having an acid-eliminatable hydroxyl group (Patent Documents 9 to 11). Materials having an acid-eliminatable hydroxyl group are also disclosed in Non-Patent Documents 1 to 3.

CITATION LIST

Patent Document 1: JP-A 2010-276910
Patent Document 2: JP-A 2010-164933
Patent Document 3: JP-A 2008-249762
Patent Document 4: JP-A H05-232702
Patent Document 5: JP-A H08-202037
Patent Document 6: JP-A 2001-226430
Patent Document 7: JP-A 2003-337414
Patent Document 8: JP-A 2001-154357
Patent Document 9: U.S. Pat. No. 7,300,739
Patent Document 10: U.S. Pat. No. 7,393,624
Patent Document 11: U.S. Pat. No. 7,563,558
Patent Document 12: JP-A 2008-102383
Patent Document 13: JP-A 2008-304590
Patent Document 14: JP-A 2013-164588 (US 20130209922, EP 2626743)
Non-Patent Document 1: H. Ito and R. Sooriyakumaran, IBM Technical Disclosure Bulletin Vol. 35, No. 1B, 397 (1992)
Non-Patent Document 2: H. Ito, Y. Maekawa, R. Sooriyakumaran, and E. A. Mash, ACS Symposium Series 537, Chapter 5, pp 64-87 (1994)
Non-Patent Document 3: K, Yoshida and J. M. J. Frechet, Polymer, 35 (1), 5 (1994)

DISCLOSURE OF INVENTION

While the demand for writing of finer size patterns continues, it is desired to improve resolution, LER, and temperature dependence. Although the resist composition described in Patent Document 14 exhibits improved resolution and overcomes pattern density dependence, there is still a demand for further improvements in performance. It is one of tradeoffs of chemically amplified resist compositions that resist sensitivity is increased at the sacrifice of resolution. Thus reducing the sensitivity of resist composition is considered as one countermeasure for improving resolution. However, a reduction of sensitivity means an increased quantity of electric current during writing, raising a new problem that the dependence of pattern size on bake temperature increases. It is thus desired to have a resist composition which is less dependent on bake temperature even when writing at a current quantity of at least 50 A, especially a high current quantity of at least 200 A. During high current quantity writing, heat is locally generated, by which some components (e.g., acid generated from PAG, and basic compound) in the exposed region will volatilize off and re-deposit on the unexposed region. This phenomenon, called "chemical flare," raises some problems to the resolution and dimensional control of pattern, which remain unsolved.

An object of the invention is to provide a negative tone resist composition which establishes a high resolution corresponding to a sub-50 nm size and a low LER, which is not affected by the heat generated by irradiation of high-energy radiation, typically EB, and which has less temperature dependence and stability to chemical flare; and a pattern forming process using the composition.

Aiming to improve the resist composition of Patent Document 14 comprising a polymer comprising cyclic olefin units having aromatic ring and acid-eliminatable group units on side chain and exhibiting high resolution, the inventors continued trial-and-error experiments.

It is presumed that the cause of temperature dependence is accounted for by the volatilization of the quencher by the heat generated locally in the image region as a result of high current quantity writing. In an experiment using an amine compound having a relatively high boiling point, the temperature dependence is mitigated, but not to a satisfactory extent, and LER is rather increased. Quite unexpectedly, the inventors have found that by using a carboxylic acid salt compound as the quencher and incorporating into the polymer chain units capable of generating acid upon exposure, there is obtained a resist composition which is less temperature dependent and forms a pattern at a satisfactory level of resolution and roughness.

In one aspect, the invention provides a negative resist composition comprising (A) a polymer comprising recurring units having the general formula (1) and recurring units of at least one type selected from units having the general formulae (a1), (a2), and (a3) and (B) a salt having the general formula (3a).

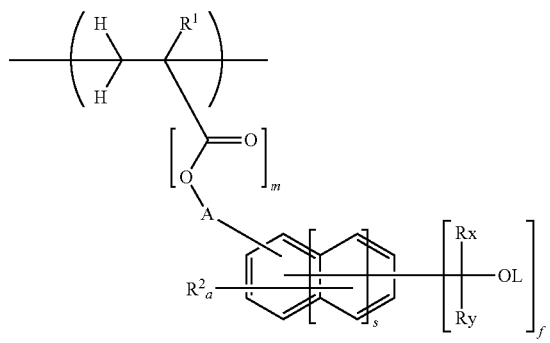

Herein A is a single bond or a $C_1$-$C_{10}$ alkylene group which may contain an ethereal oxygen atom at an intermediate of the chain, $R^1$ is hydrogen, fluorine, methyl or trifluoromethyl, $R^2$, is hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, L is hydrogen, a monovalent, straight, branched or cyclic, aliphatic $C_1$-$C_{10}$ hydrocarbon group which may contain an ethereal oxygen atom, carbonyl moiety or carbonyloxy moiety at an intermediate of the chain, or an optionally substituted monovalent aromatic group, Rx and Ry each are hydrogen, a $C_1$-$C_{15}$ alkyl group which may be substituted with hydroxy or alkoxy, or an optionally substituted monovalent aromatic group, Rx and Ry may bond together to form a ring with the carbon atom to which they are attached, excluding the case where Rx and Ry are hydrogen at the same time, f is an integer of 1 to 3, s is an integer of 0 to 2, a is an integer (5+2s-f), and m is 0 or 1,

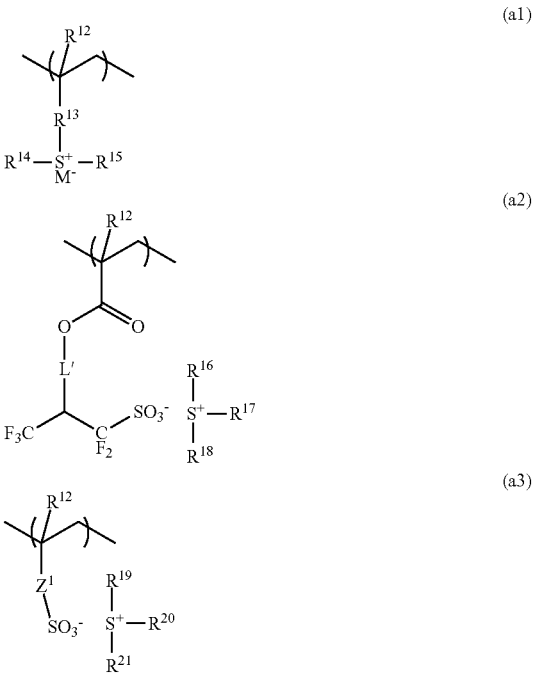

Herein $R^{12}$ is each independently hydrogen or methyl, $R^{13}$ is a single bond, phenylene group, —O—$R^{22}$—, or —C(=O)—$Z^2$—$R^{22}$—, $Z^2$ is oxygen or NH, $R^{22}$ is a straight, branched or cyclic $C_1$-$C_6$ alkylene, alkenylene or phenylene group which may contain a carbonyl (—CO—), ester (—COO—), ether (—O—) or hydroxyl moiety, L' is a single bond or —$Z^3$—C(=O)—O—, $Z^3$ is a straight, branched or cyclic divalent $C_1$-$C_{20}$ hydrocarbon group which may be substituted with a heteroatom, $Z^1$ is a single bond, methylene, ethylene, phenylene, fluorinated phenylene, —O—$R^{23}$—, or —C(=O)—$Z^4$—$R^{23}$—, $Z^4$ is oxygen or NH, $R^{23}$ is a straight, branched or cyclic $C_1$-$C_6$ alkylene, alkenylene or phenylene group which may contain a carbonyl, ester, ether or hydroxyl moiety, M⁻ is a non-nucleophilic counter ion, $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which at least one hydrogen atom may be replaced by a heteroatom selected from oxygen, sulfur, nitrogen and halogen, or in which a heteroatom selected from oxygen, sulfur and nitrogen may intervene, so that a hydroxyl group, cyano group, carbonyl group, ether bond, ester bond, sulfonic acid ester bond, carbonate bond, lactone ring, sultone ring, carboxylic anhydride, or haloalkyl group may form or intervene, or $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom.

Herein $R^{11}$ is a straight, branched or cyclic $C_1$-$C_{20}$ alkyl group, $C_2$-$C_{20}$ alkenyl group or $C_6$-$C_{20}$ aryl group, which may contain fluorine, nitrogen, ether moiety, ester moiety, lactone ring, lactam ring, carbonyl moiety, or hydroxyl moiety, and M is a substituent-bearing counter cation selected from sulfonium, iodonium and ammonium cations.

In a preferred embodiment, the polymer (A) further comprises recurring units of at least one type selected from units having the general formulae (2) and (3).

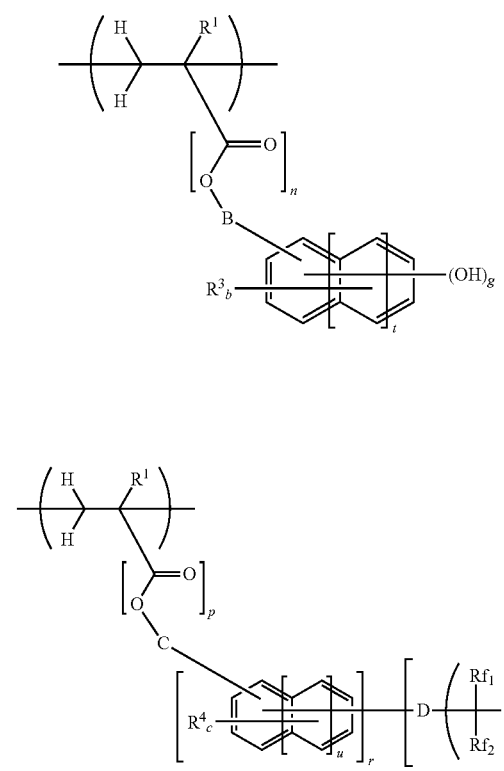

Herein B and C each are a single bond or a $C_1$-$C_{10}$ alkylene group which may contain an ethereal oxygen atom at an intermediate of the chain, D is a single bond or a (v+1)-valent, straight, branched or cyclic, aliphatic $C_1$-$C_{10}$ hydrocarbon group which may be substituted with fluorine and which may contain an ethereal oxygen atom, carbonyl moiety or carbonyloxy moiety at an intermediate of the chain, $R^1$ is hydrogen, fluorine, methyl, or trifluoromethyl, $R^3$ and $R^4$ are each independently hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, $Rf_1$ and $Rf_2$ each are a $C_1$-$C_6$ alkyl group having at least one fluorine, $Rf_1$ may bond with D to form a ring with the carbon atom to which they are attached, g is an integer of 0 to 3, h is 1 or 2, r is 0 or 1, v is 1 or 2, t and u each are an integer of 0 to 2, b is an integer (5+2t-g), c is an integer (5+2u-h), n and p are each independently 0 or 1, with the proviso that p is 1 when r is 0.

In a preferred embodiment, the polymer (A) further comprises recurring units of at least one type selected from units having the general formulae (4) and (5).

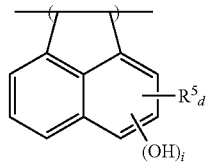

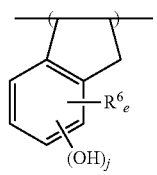

Herein $R^5$ and $R^6$ are each independently hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, i and j each are an integer of 0 to 3, a is an integer of 0 to 5, and e is an integer of 0 to 3.

In a preferred embodiment, the resist composition further comprises (C) an additional polymer comprising recurring units having the general formula (1), but free of recurring units having a site capable of generating an acid upon exposure to high-energy radiation.

The resist composition may further comprise a compound capable of generating an acid upon exposure to high-energy radiation.

In another aspect, the invention provides a photomask blank coated with the negative resist composition defined above.

In a further aspect, the invention provides a pattern forming process comprising the steps of applying the negative resist composition defined above onto a processable substrate to form a resist film thereon, exposing patternwise the resist film to high-energy radiation, and developing the resist film in an alkaline developer to form a resist pattern.

Preferably the high-energy radiation is EUV or EB. Typically, the processable substrate is a photomask blank. The photomask blank preferably has an outermost surface formed of a chromium based material.

Advantageous Effects of Invention

When the negative tone resist composition of the invention is processed by the microprocessing technology, especially EB lithography, it forms a pattern having a very high resolution and minimal LER. By virtue of the mitigated temperature dependence of feature size, the resist composition is successful in fully suppressing the size shift between the design and an actual feature size caused by the heat locally generated by EB writing in a high current quantity.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The acronym "PAG" stands for photoacid generator, "PEB" for post-exposure bake, "LER" for line edge roughness, "PCD" for post-coating delay, "GPC" for gel permeation chromatography, "Mw" for weight average molecular weight, and "Mw/Mn" for molecular weight dispersity. In the chemical formulae, the broken line designates a valence bond, Me stands for methyl, and Ac for acetyl.

The term "high-energy radiation" is intended to encompass ultraviolet (UV) radiation, deep UV, extreme ultraviolet (EUV), electron beam (EB), x-ray, excimer laser, γ-ray and synchrotron radiation.

According to the invention, the negative resist composition is defined as comprising (A) a polymer comprising recurring units having the general formula (1) and recurring units of at least one type selected from units having the general formulae (a1), (a2), and (a3) and (B) a salt having the general formula (3a). It is preferred that the resist composition is free of a crosslinker.

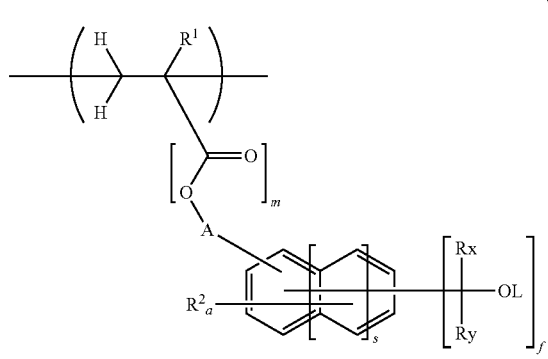
(1)

In formula (1), A is a single bond or a $C_1$-$C_{10}$ alkylene group which may contain an ethereal oxygen atom at an intermediate of the chain. $R^1$ is hydrogen, fluorine, methyl or trifluoromethyl, $R^2$ is hydrogen, halogen, an optionally halo-substituted, straight, branched or cyclic: $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group. L is hydrogen, a monovalent, straight, branched or cyclic, aliphatic $C_1$-$C_{10}$ hydrocarbon group which may contain an ethereal oxygen atom, carbonyl moiety or carbonyloxy moiety at an intermediate of the chain, or an optionally substituted monovalent aromatic group. Rx and Ry each are hydrogen, a $C_1$-$C_{15}$ alkyl group which may be substituted with hydroxy or alkoxy, or an optionally substituted monovalent aromatic group, Rx and Ry may bond together to form a ring with the carbon atom to which they are attached, excluding the case where Rx and Ry are hydrogen at the same time. The subscript f is an integer of 1 to 3, s is an integer of 0 to 2, a is an integer (5+2s-f), and m is 0 or 1.

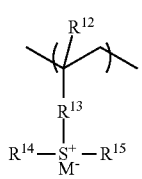
(a1)

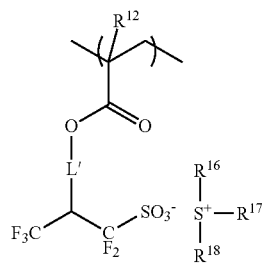
(a2)

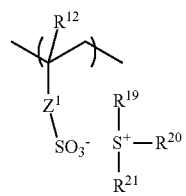
(a3)

In formulae (a1), (a2) and (a3), $R^{12}$ is each independently hydrogen or methyl. $R^{13}$ is a single bond, phenylene group, —O—$R^{22}$—, or —C(=O)—$Z^2$—$R^{22}$—, wherein $Z^2$ is oxygen or NH, $R^{22}$ is a straight, branched or cyclic $C_1$-$C_6$ alkylene, alkenylene or phenylene group which may contain a carbonyl (—CO—), ester (—COO—), ether (—O—) or hydroxyl moiety, L' is a single bond or —$Z^3$—C(=O)—O—, wherein $Z^3$ is a straight, branched or cyclic divalent $C_1$-$C_{20}$ hydrocarbon group which may be substituted with a heteroatom. $Z^1$ is a single bond, methylene, ethylene, phenylene, fluorinated phenylene, —O—$R^{23}$—, or —C(=O)—$Z^4$—$R^{23}$—, wherein $Z^4$ is oxygen or NH, $R^{23}$ is a straight, branched or cyclic $C_1$-$C_6$ alkylene, alkenylene or phenylene group which may contain a carbonyl, ester, ether or hydroxyl moiety. $M^-$ is a non-nucleophilic counter ion. $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which at least one hydrogen atom may be replaced by a heteroatom selected from oxygen, sulfur, nitrogen and halogen, or in which a heteroatom selected from oxygen, sulfur and nitrogen may intervene, so that a hydroxyl group, cyano group, carbonyl group, ether bond, ester bond, sulfonic acid ester bond, carbonate bond, lactone ring, sultone ring, carboxylic anhydride, or haloalkyl group may form or intervene, or $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom.

$$R^{11}-CO_2^- M^+ \quad (3a)$$

In formula (3a), $R^{11}$ is a straight, branched or cyclic $C_1$-$C_{20}$ alkyl group, $C_2$-$C_{20}$ alkenyl group or $C_6$-$C_{20}$ aryl group, which may contain fluorine, nitrogen, ether moiety, ester moiety, lactone ring, lactam ring, carbonyl moiety, or hydroxyl moiety. M is a substituent-bearing counter cation selected from sulfonium, iodonium and ammonium cations.

The recurring unit of formula (1) included in the polymer performs in such a way that an acid-eliminatable group (—CRxRy-OL) may undergo elimination reaction under the catalysis of an acid generated by the acid generator upon exposure to high-energy radiation whereby the unit itself induces alkali insolubilization and crosslinking reaction between polymer molecules.

The acid-eliminatable group-bearing side chain substitutes on the aromatic ring, and f indicative of the number of substitutions ranges from 1 to 3. L is hydrogen, a monovalent, straight, branched or cyclic, aliphatic $C_1$-$C_{10}$ hydrocarbon group which may contain an ethereal oxygen atom, carbonyl moiety or carbonyloxy moiety at an intermediate of the chain, or an optionally substituted monovalent aromatic group. Preferred examples of L include hydrogen, methyl, ethyl, propyl, isopropyl, cyclopentyl, cyclohexyl, adamantyl, methylcarbonyl, and phenyl.

Rx and Ry each are hydrogen, a $C_1$-$C_{15}$ alkyl group which may be substituted with hydroxy or alkoxy, or an optionally substituted monovalent aromatic group, excluding the case where Rx and Ry are hydrogen at the same time. Preferred structures of Rx and Ry include methyl, ethyl, popyl, butyl, and structural isomers thereof, and the foregoing groups having a hydroxyl or alkoxy moiety substituted thereon. Rx and Ry may bond together to form a ring with the carbon atom to which they are attached. The preferred examples include cyclopentyl group, cyclohexyl group, adamantyl group, and the foregoing groups having a hydroxy or alkoxy moiety substituted thereon.

In formula (1), the aromatic ring may be bonded to the main chain via a single bond, via a carbonyloxy group or via a linker "A." The subscript s is an integer of 0 to 2. The structure represents a benzene ring when s=0, a naphthalene ring when s=1, or an anthracene ring when s=2.

"A" is a single bond, or a $C_1$-$C_{10}$ alkylene group which, may contain an ethereal oxygen atom (or ether bond) at an intermediate of the chain. Preferred alkylene groups include methylene, ethylene, propylene, butylene, pentylene, hexylene, and structural isomers of carbon skeleton having a branched or cyclic structure. When an ethereal oxygen atom is contained, in case m=1 in formula (1), it may be at any position excluding between the α- and β-position carbons relative to the ester oxygen. In case m=0 in formula (1), the atom bonding to the main chain is an ethereal oxygen atom, and a second ethereal oxygen atom may be contained at any position excluding between the α- and β-position carbons relative to that ethereal oxygen.

Preferred examples of the recurring unit having formula (1) are illustrated below.

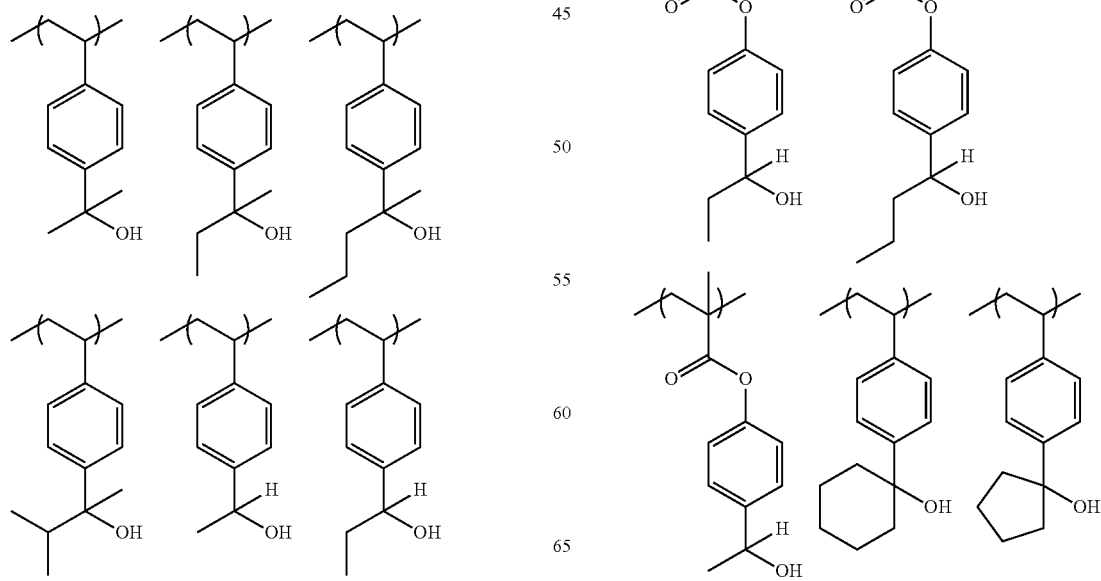

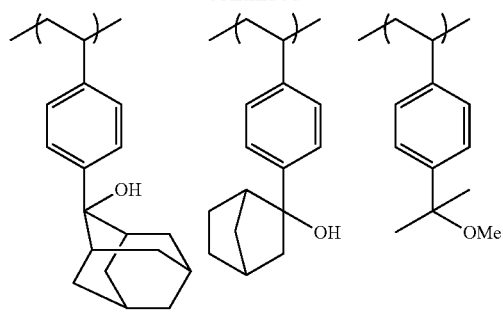

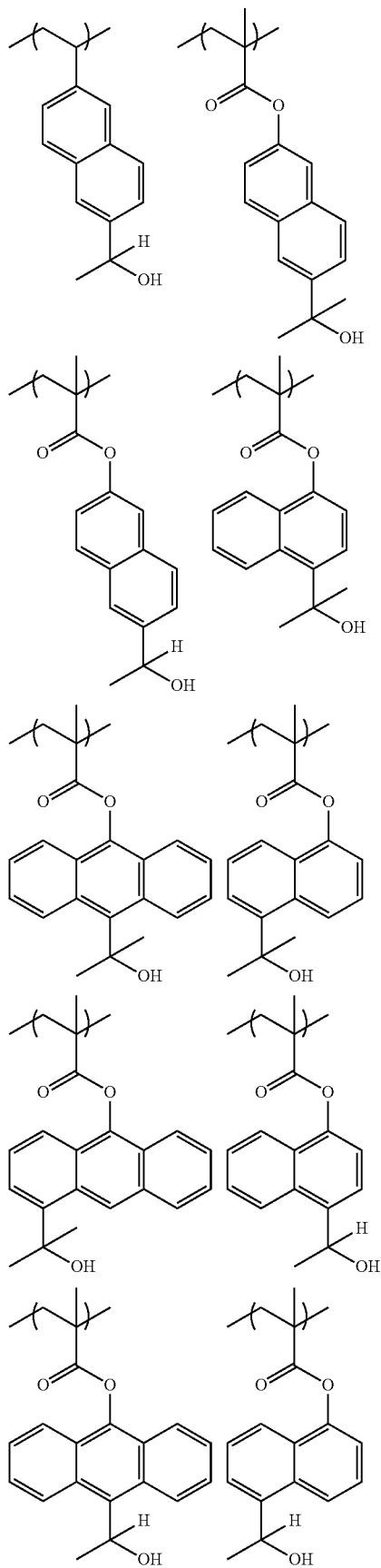
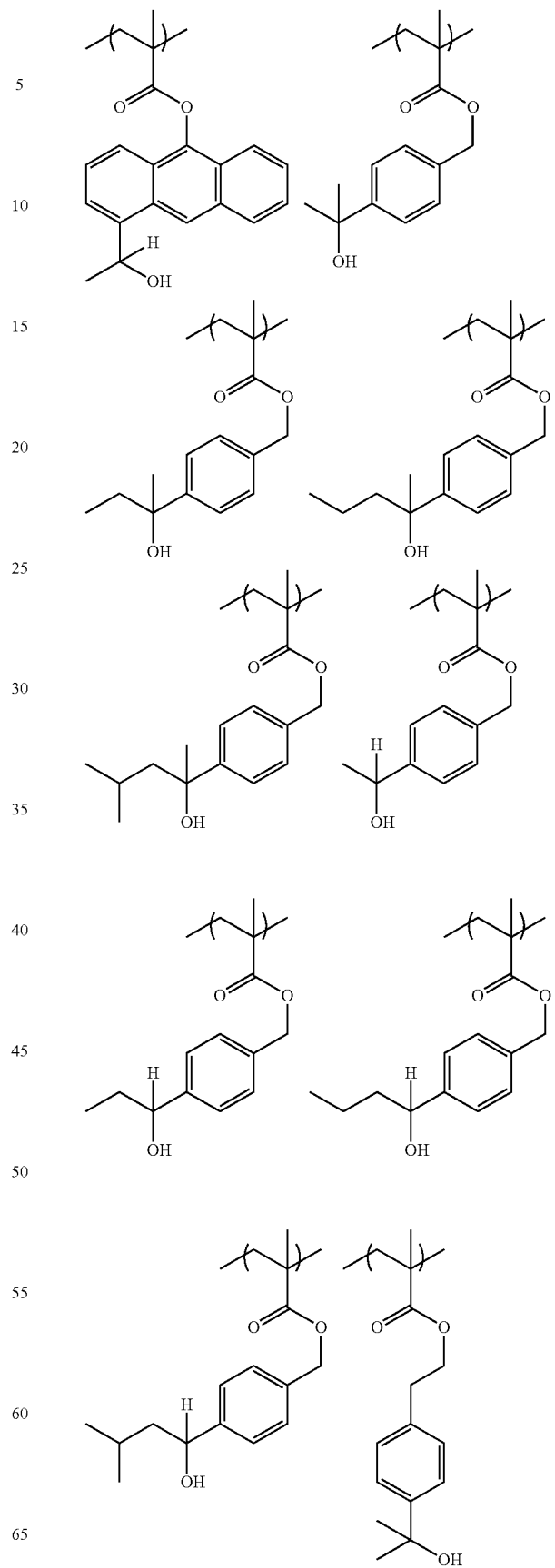

-continued

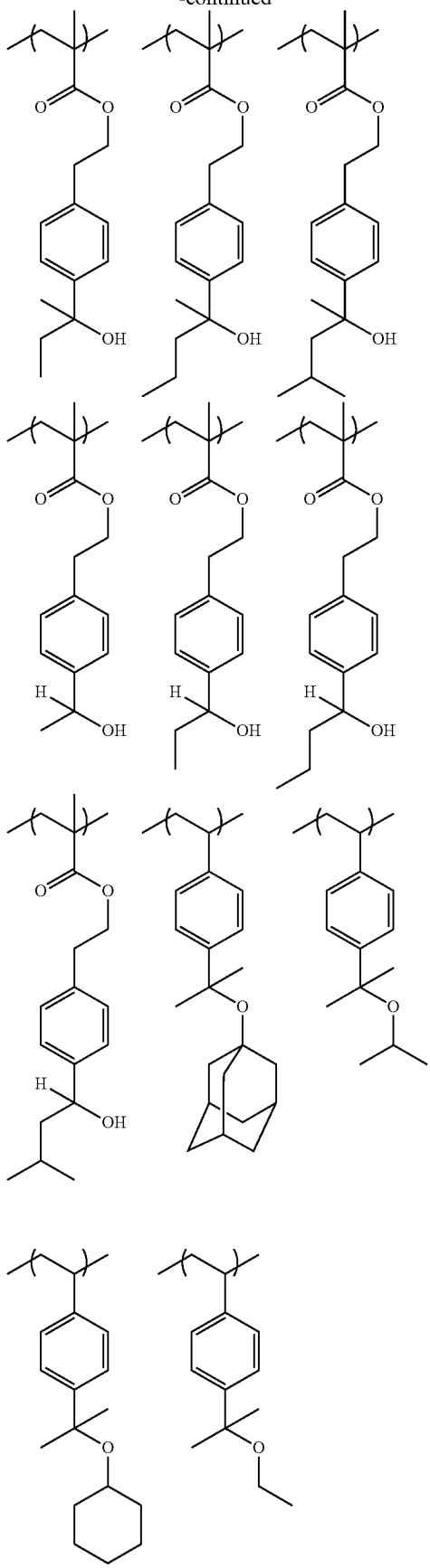

-continued

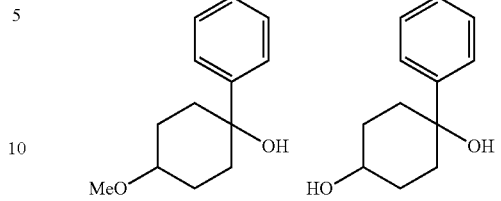

In addition to the recurring units of formula (1), the polymer should comprise recurring units of at least one type selected from units having the general formulae (a1), (a2), and (a3).

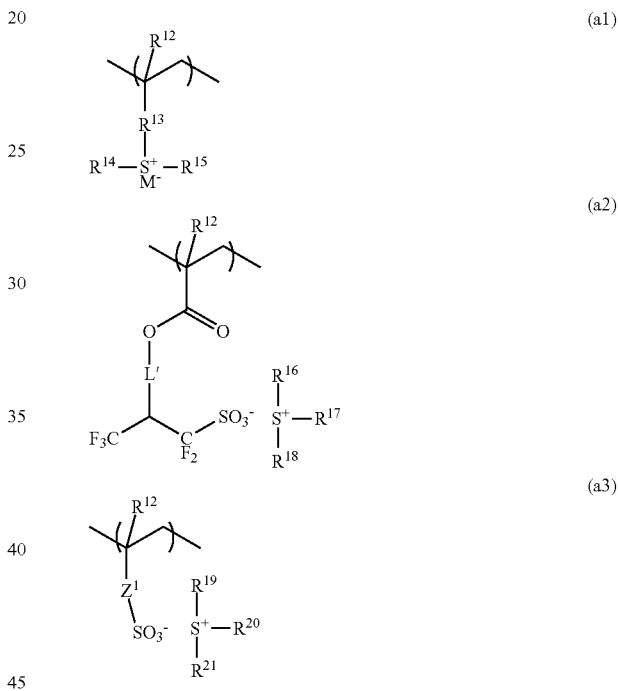

In formulae (a1), (a2), and (a3), $R^{12}$ is each independently hydrogen or methyl, $R^{13}$ is a single bond, phenylene group, —O—$R^{22}$—, or —C(=O)—$Z^2$—$R^{22}$—, wherein $Z^2$ is oxygen or MH, $R^{22}$ is a straight, branched or cyclic $C_1$-$C_6$ alkylene, alkenylene or phenylene group which may contain a carbonyl (—CO—), ester (—COO—), ether (—O—) or hydroxyl moiety. L' is a single bond or —$Z^3$—C(=O)—O—, wherein is a straight, branched or cyclic divalent $C_1$-$C_{20}$ hydrocarbon group which may be substituted with a heteroatom. $Z^1$ is a single bond, methylene, ethylene, phenylene, fluorinated phenylene, —O—$R^{23}$—, or —C(=O)—$Z^4$—$R^{23}$—, wherein $Z^4$ is oxygen or NH, $R^{23}$ is a straight, branched or cyclic $C_1$-$C_6$ alkylene, alkenylene or phenylene group which may contain a carbonyl, ester, ether or hydroxyl moiety. M is a non-nucleophilic counter ion. $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which at least one hydrogen atom may be replaced by a heteroatom selected from oxygen, sulfur, nitrogen and halogen, or in which a heteroatom selected from oxygen, sulfur and nitrogen may intervene, so that a hydroxyl group, cyano group, carbonyl group, ether bond, ester bond, sulfonic acid ester bond, carbonate bond, lactone ring, sultone ring, carboxylic anhydride, or haloalkyl group may form or intervene, or $R^{14}$ and may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom.

In formula (a2), when L' is —$Z^3$—C(=O)—O—, $Z^3$ is a straight, branched or cyclic divalent $C_1$-$C_{20}$ hydrocarbon group which may be substituted with a heteroatom. Examples of the divalent hydrocarbon group are illustrated below, but not limited thereto.

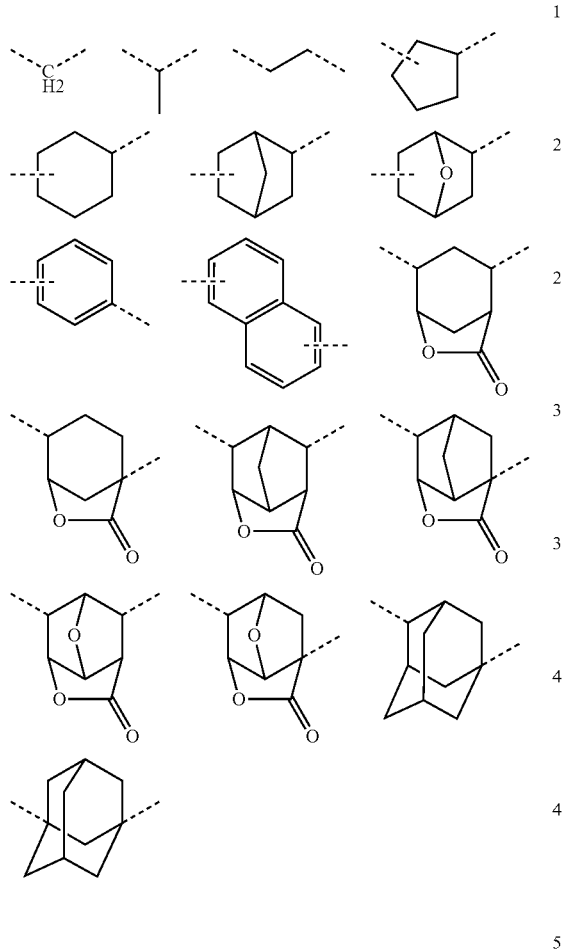

In formulae (a1) to (a3), $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom. Exemplary ring structures are shown below.

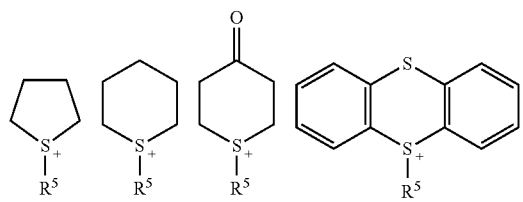

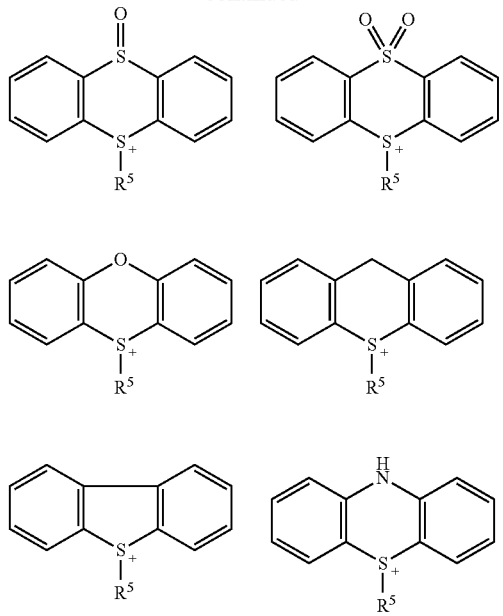

Herein, $R^5$ is as defined and exemplified for $R^{14}$ to $R^{21}$.

Exemplary structures of the sulfonium cation in formulae (a2) and (a3) are shown below, but not limited thereto.

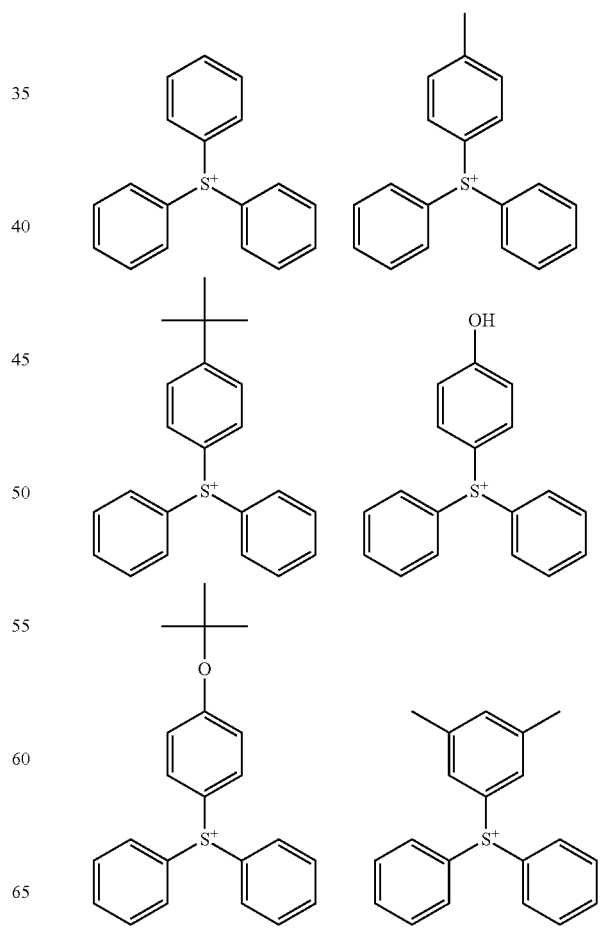

-continued
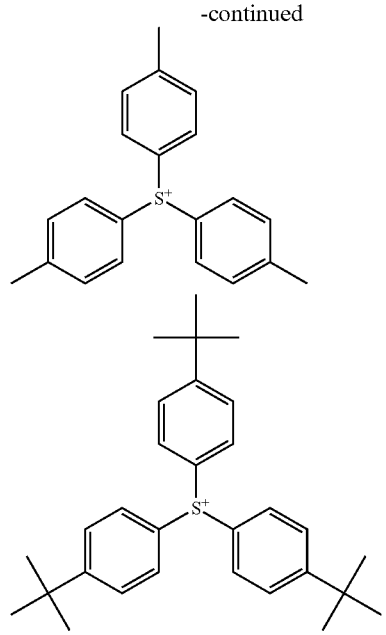
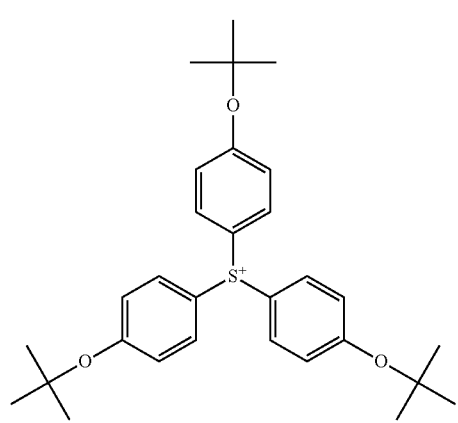 [SMILES: CC(C)(C)Oc1ccc([S+](c2ccc(OC(C)(C)C)cc2)c2ccc(OC(C)(C)C)cc2)cc1]
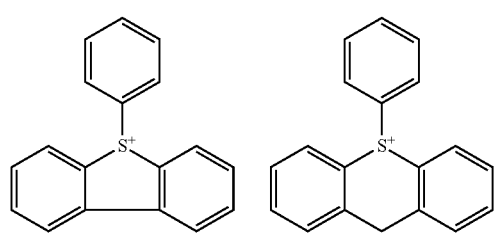
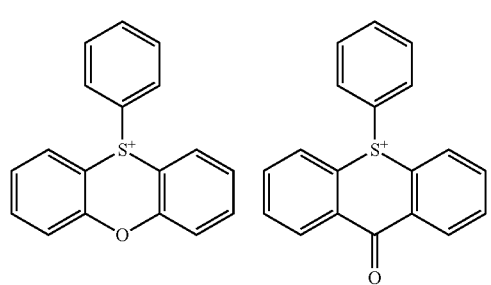
-continued
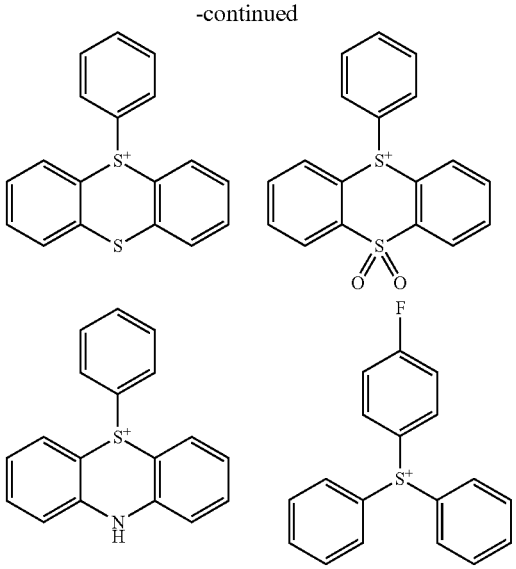
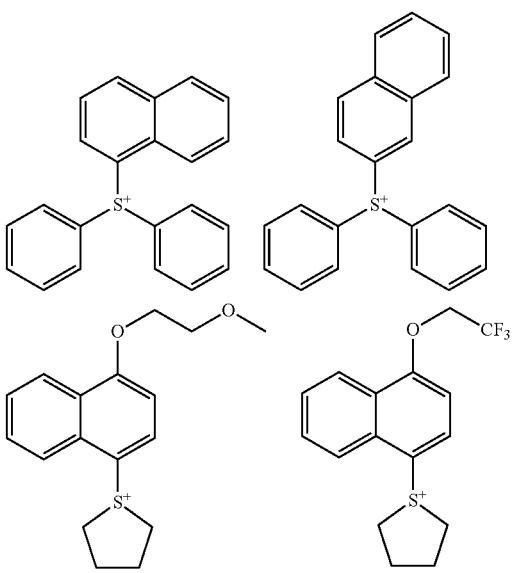
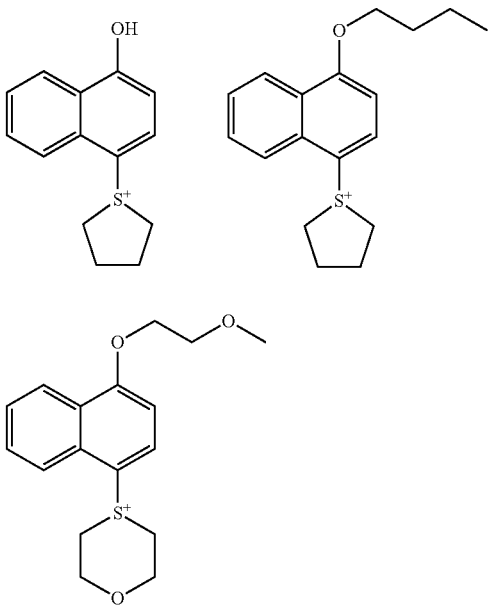

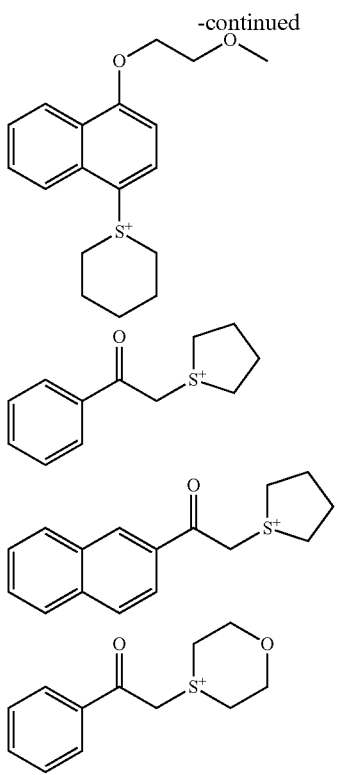

The units of formulae (a1), (a2) and (a3) are capable of generating an acid upon exposure to high-energy radiation. It is believed that when these units are bound to the polymer, acid diffusion is appropriately suppressed, and so a pattern having reduced LER is formed. The binding of acid-generating units in the polymer suppresses the chemical flare phenomenon that acid volatilizes off the exposed region and re-deposits on the unexposed region during bake in vacuum. This is effective for reducing LER and for suppressing the unwanted negative-working reaction in the unexposed region, thus reducing defects.

The negative resist composition further comprises a salt having the general formula (3a).

$$R^{11}\!-\!CO_2^-M^+ \tag{3a}$$

In formula (3a), $R^{11}$ is a straight, branched or cyclic $C_1$-$C_{20}$ alkyl group, $C_2$-$C_{20}$ alkenyl group or $C_6$-$C_{20}$ aryl group, which may contain fluorine, nitrogen, ether moiety, ester moiety, lactone ring, lactam ring, carbonyl moiety, or hydroxyl moiety. M is a substituent-bearing counter cation selected from sulfonium, iodonium and ammonium cations.

In the resist composition, the salt of formula (3a) is preferably added in an amount of 0.01 to 20 parts by weight, more preferably 0.05 to 15 parts by weight per 100 parts by weight of the polymer of formula (1).

The salt of formula (3a) functions as an acid diffusion regulator since it undergoes exchange reaction with the acid generated upon exposure. Since this salt is an ionic compound, it does not volatilize by heat. In contrast, amine compounds which are commonly used as the acid diffusion regulator can volatilize by heat, during bake or image writing. Since an ionic compound is used as the acid diffusion regulator, the negative resist composition of the invention has the advantages that it is not affected by the heat generated during bake or image writing and the temperature dependence of feature size is mitigated.

Exemplary structures of the anion moiety in the salt of formula (3a) are shown below, but not limited thereto.

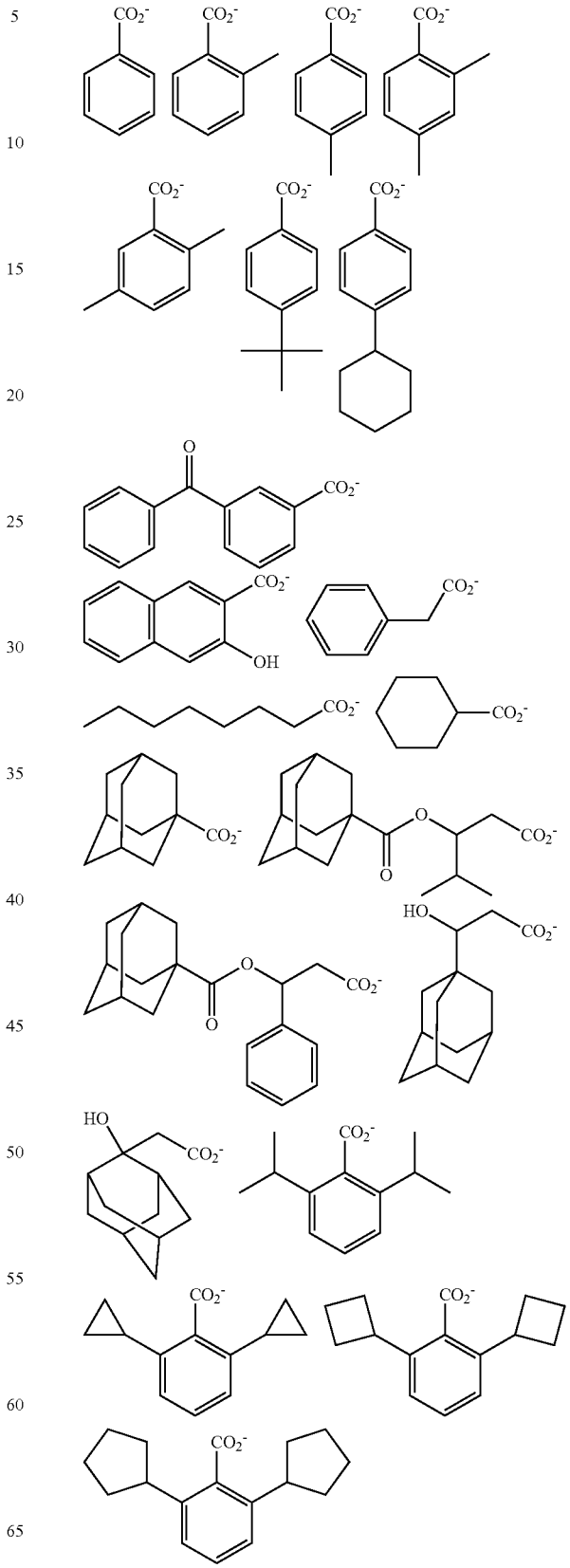

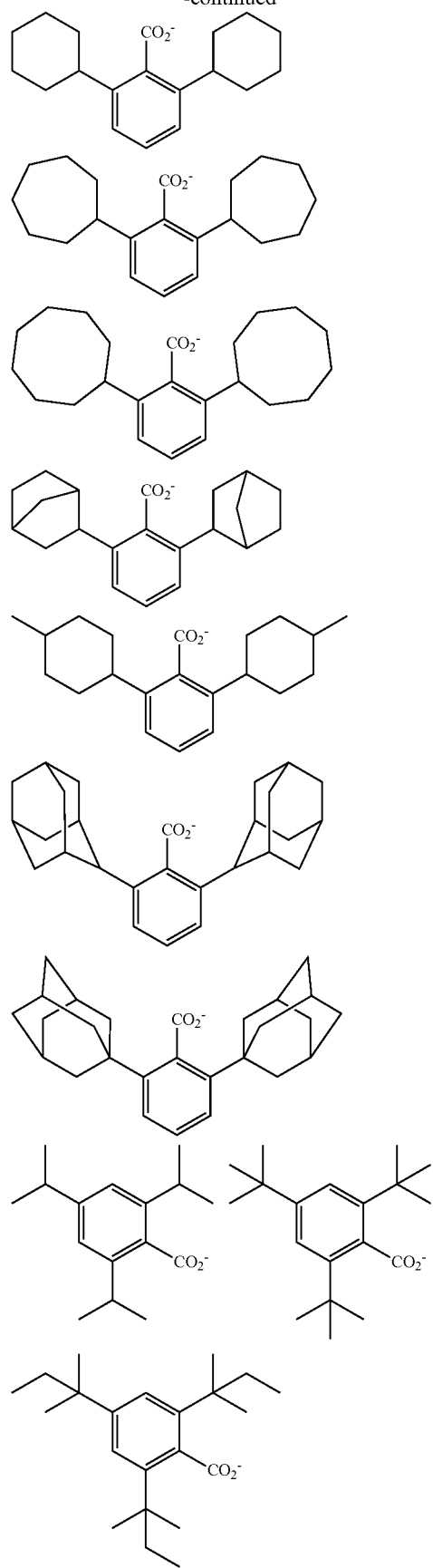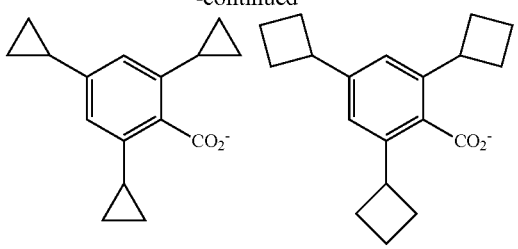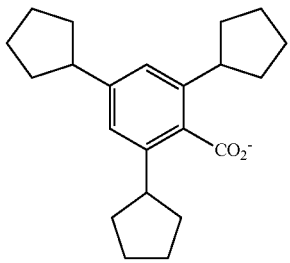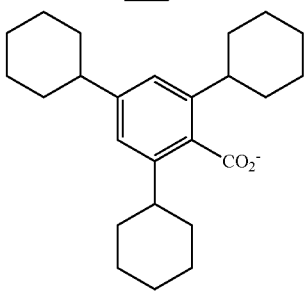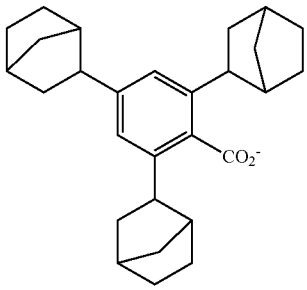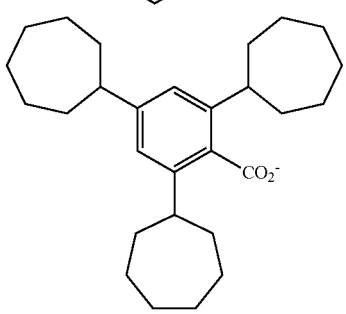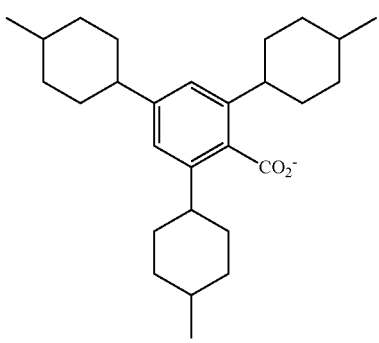

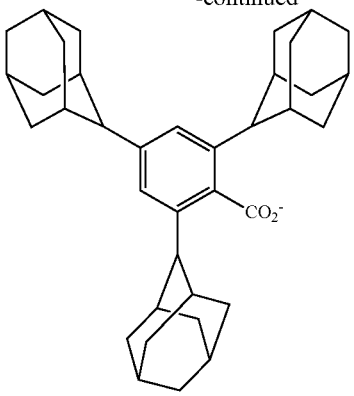

Exemplary structures of the cation moiety in the salt of formula (3a) include those illustrated above for the ring structure of $R^{14}$-$R^{15}$, $R^{16}$-$R^{17}$-$R^{18}$ or $R^{19}$-$R^{20}$-$R^{21}$, and more specifically, the structures exemplified for the sulfonium cations of formulae (a2) and (a3).

For the purpose of achieving a high resolution, preferably the polymer in the negative resist composition further comprises recurring units having the general formula (2) and/or (3) as the unit that allows for appropriate thermal motion of the polymer so as to effectively promote the insolubilizing reaction associated with elimination of the acid-eliminatable group in the recurring unit having formula (1). Also preferably the polymer may further comprise recurring units having the general formula (4) and/or (5).

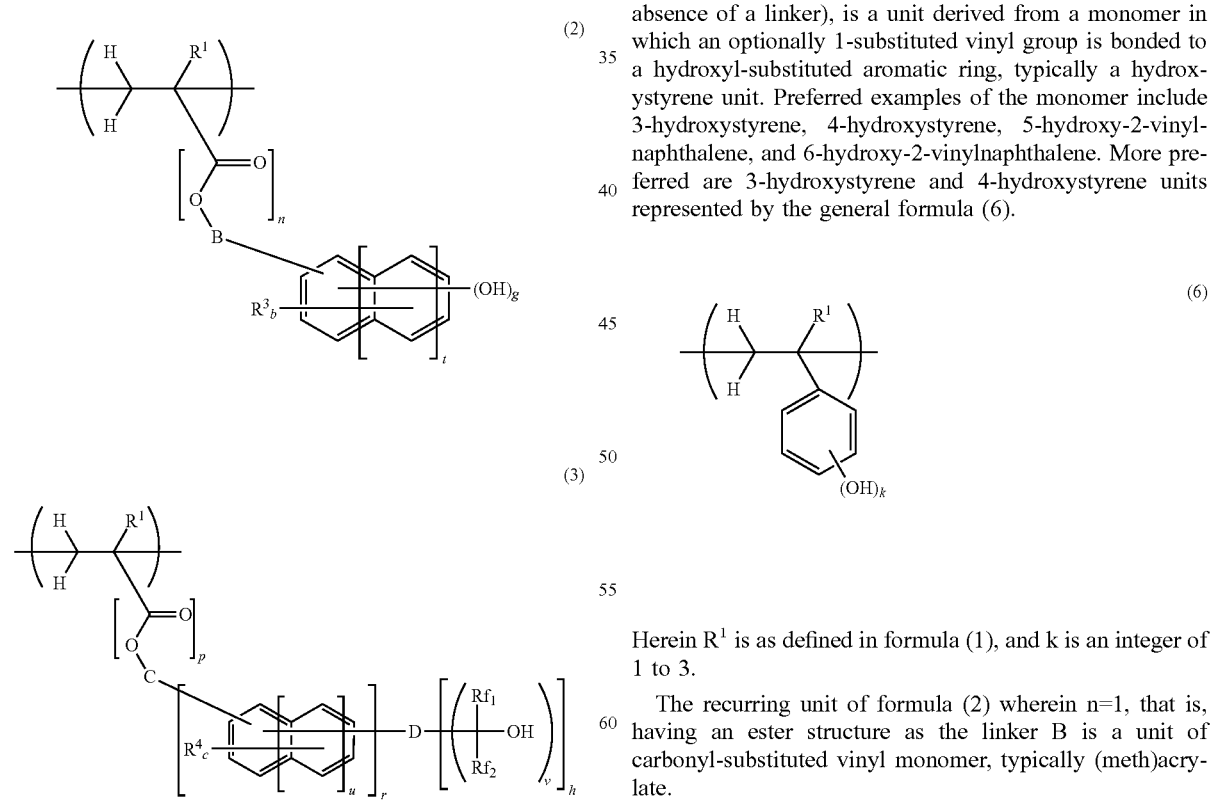

In formula (2), $R^1$ is as defined in formula (1). $R^3$ and b are as defined for $R^2$ and a in formula (1), respectively. Preferred examples of these groups are the same as enumerated above. The linker B is as defined for A in formula (1), and preferred examples thereof are the same as enumerated above.

In formula (2), g indicative of the number of hydroxyl groups substituting on the aromatic ring ranges from 0 to 3. The resist polymer should preferably comprise either recurring units having a phenolic hydroxyl group or recurring units having formula (3) for endowing the resist polymer with solubility in aqueous alkaline developer and substrate adhesion, as will be described later. Also, in order that the polymer achieve a high resolution by establishing a high activity to the insolubilizing reaction associated with elimination of the acid-eliminatable group in the recurring unit having formula (1), the resist polymer preferably comprises recurring units of formula (2) wherein g is at least 1, more preferably at least 50 mol % of recurring units of formula (2) wherein q is at least 1. Notably, the unit of formula (2) wherein g=0 may be used for adjusting the dissolution rate and for adjusting the degree of allowance for thermal vibration of the polymer although this unit may be omitted in a certain polymer design.

Like formula (1), the aromatic ring in the recurring unit may be bonded to the main chain via a single bond, via a carbonyloxy group or via a linker B. The subscript t is an integer of 0 to 2. The structure represents a benzene ring when t=0, a naphthalene ring when t=1, or an anthracene ring when t=2.

The recurring unit of formula (2) wherein g is at least 1, n is 0, and B is a single bond, that is, the aromatic ring is bonded directly to the polymer main chain (indicative of the absence of a linker), is a unit derived from a monomer in which an optionally 1-substituted vinyl group is bonded to a hydroxyl-substituted aromatic ring, typically a hydroxystyrene unit. Preferred examples of the monomer include 3-hydroxystyrene, 4-hydroxystyrene, 5-hydroxy-2-vinylnaphthalene, and 6-hydroxy-2-vinylnaphthalene. More preferred are 3-hydroxystyrene and 4-hydroxystyrene units represented by the general formula (6).

Herein $R^1$ is as defined in formula (1), and k is an integer of 1 to 3.

The recurring unit of formula (2) wherein n=1, that is, having an ester structure as the linker B is a unit of carbonyl-substituted vinyl monomer, typically (meth)acrylate.

Of the recurring units of formula (2) having a linker (—CO—O—B—) derived from (meth)acrylates, those units wherein g is at least 1 are exemplified by the following examples.

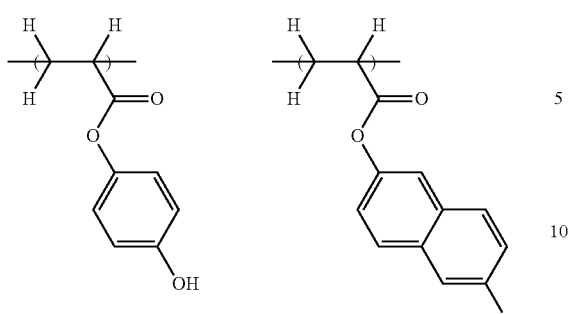
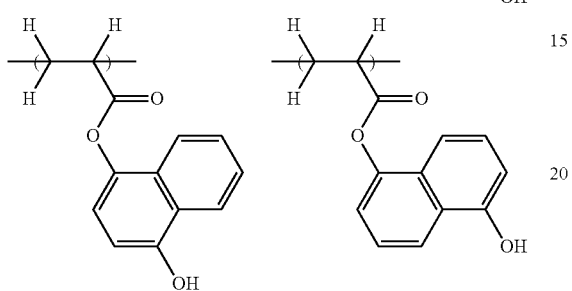
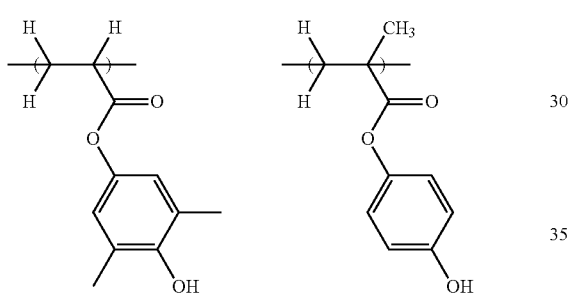
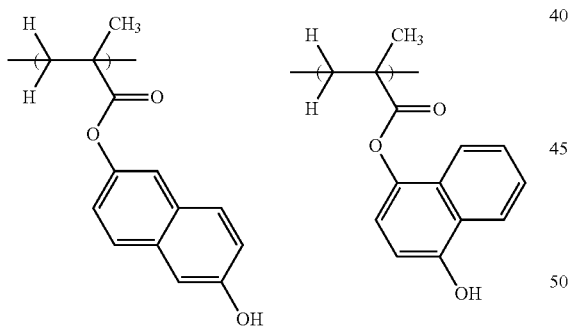
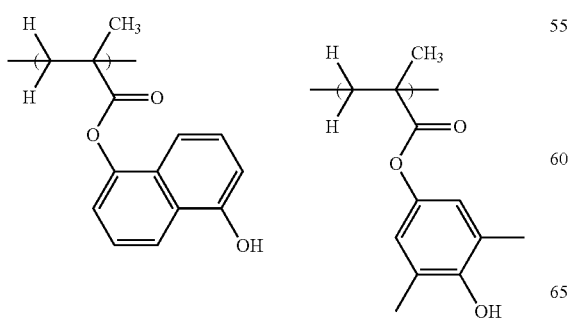
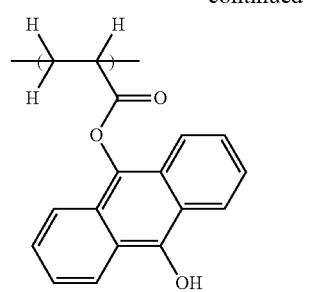
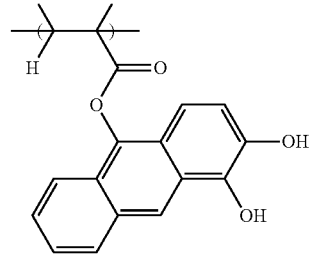
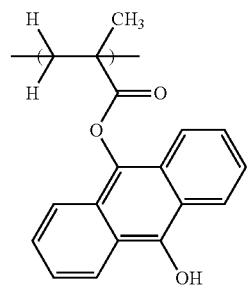
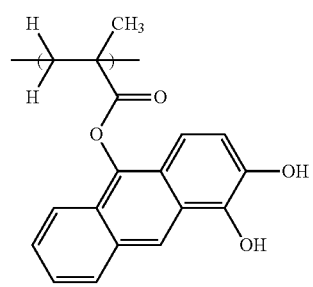
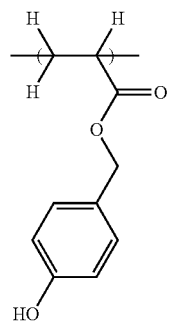
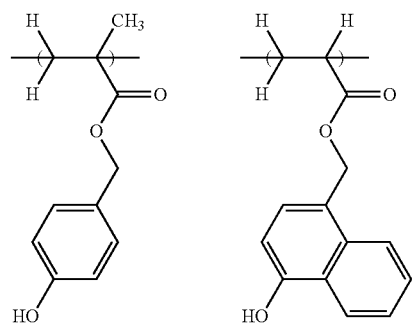

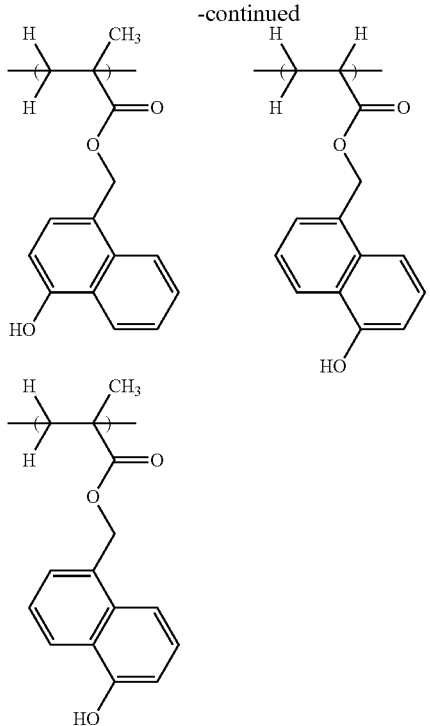

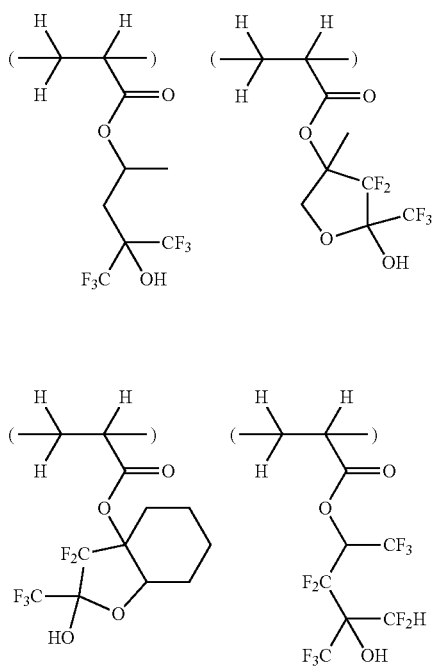

Examples of the recurring units of formula (2) wherein g=0 include styrene, vinylnaphthalene, vinylanthracene, and substituted forms of the foregoing wherein the aromatic ring is substituted with a halogen, acyloxy, alkyl or alkoxy group. Examples of the recurring units of formula (2) wherein g=0 and having a linker (—CO—O—B—) derived from a (meth)acrylate include the preferred structures wherein g is at least 1, with the hydroxyl group being eliminated or with the hydrogen of the hydroxyl group being substituted by an acyl or alkyl group.

In formula (3), $R^1$ is as defined in formula (1). $R^4$ and c are as defined for $R^2$ and a in formula (1), respectively. Preferred examples of these groups are the same as enumerated above. The linker C is as defined for A in formula (1), and preferred examples thereof are the same as enumerated above.

In formula (3), D is a single bond or a (v+1)-valent, straight, branched or cyclic, aliphatic hydrocarbon group of 1 to 10 carbon atoms which may be substituted with fluorine and which may contain an ethereal oxygen atom, carbonyl group or carbonyloxy group at an intermediate of the chain. $Rf_1$ and $Rf_2$ each are a $C_1$-$C_6$ alkyl group having at least one fluorine atom, and $Rf_1$ may bond with D to form a ring with the carbon atom to which they are attached.

In the case of r=1, an aromatic ring intervenes between the polymer main chain and the hydroxyl group on the carbon bonded to fluoro-substituted vicinal carbons. The subscript v indicative of the number of substituents on D is 1 or 2. Where D is not a single bond, D has one or two hydroxyl groups each on the carbon bonded to fluoro-substituted vicinal carbons.

In the case of r=0, p is 1, C is a single bond, and D is bonded to the polymer main chain via a carbonyloxy group. In this case too, D has one or two hydroxyl groups each on the carbon bonded to fluoro-substituted vicinal carbons.

Preferred examples of the recurring unit having formula (3) are shown below, but not limited thereto.

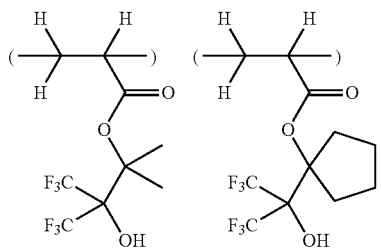

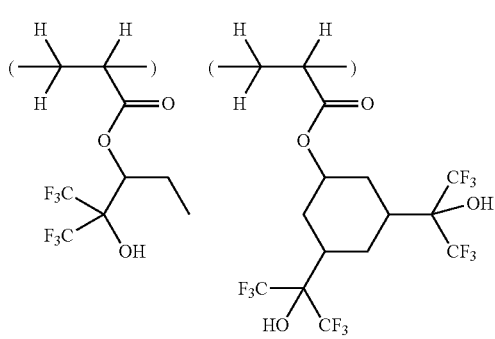

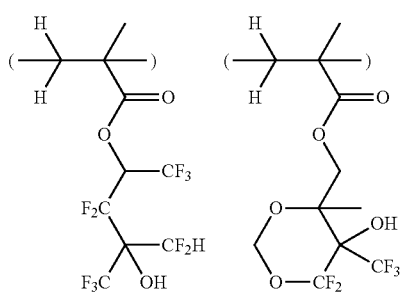

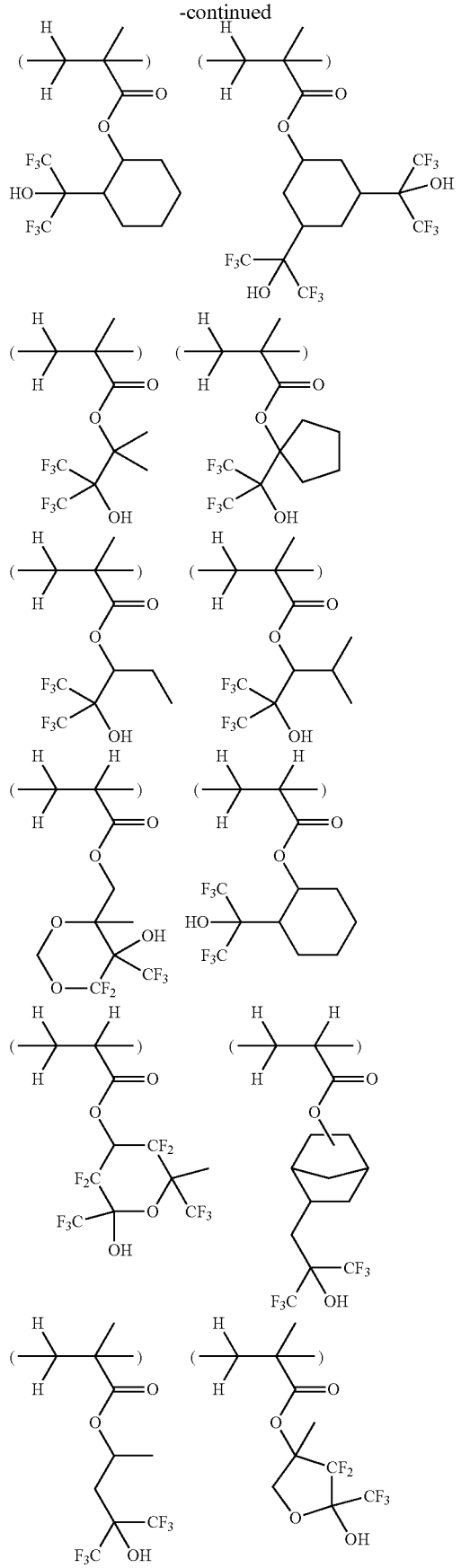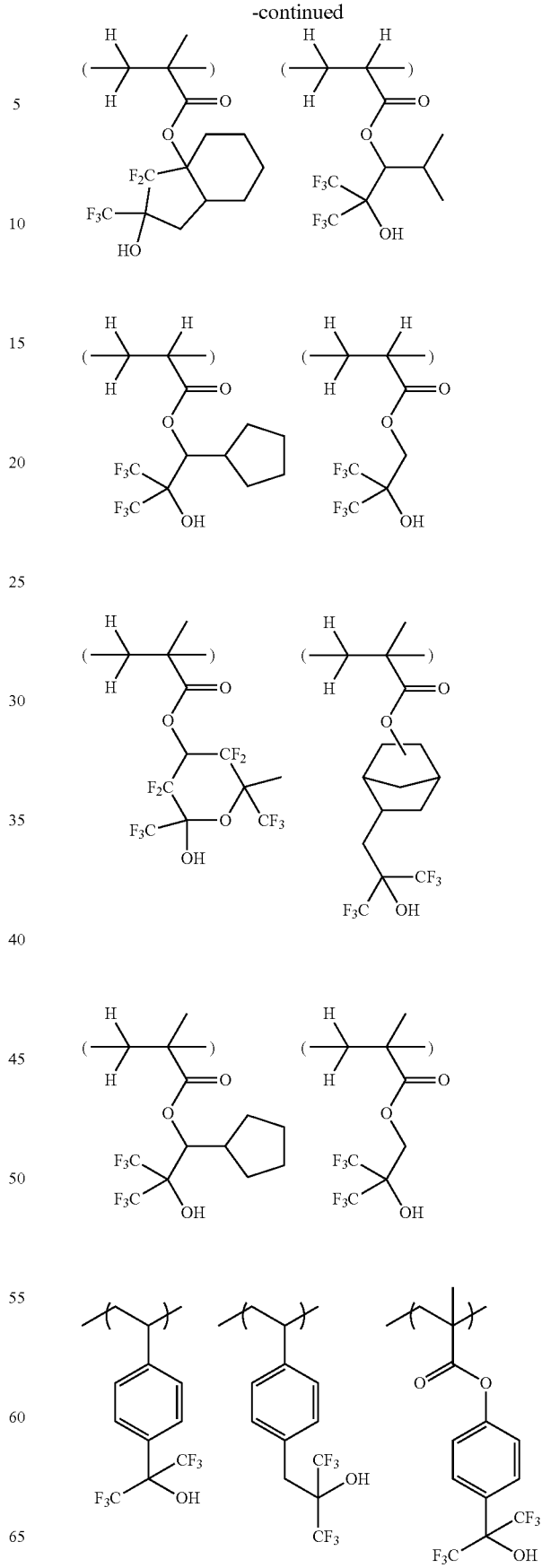

-continued

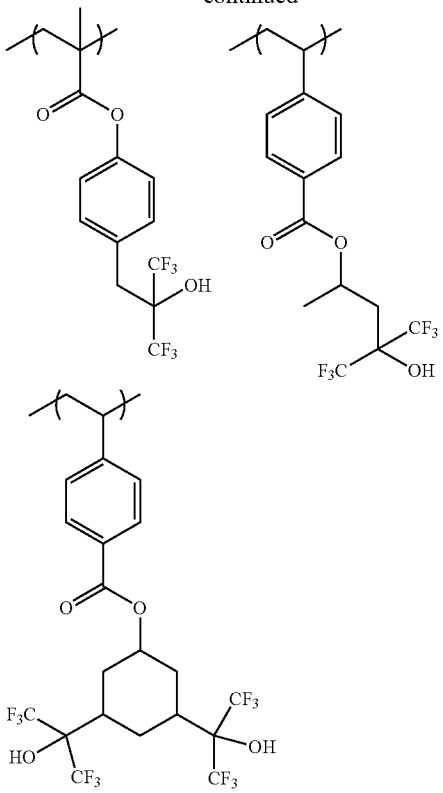

The recurring unit having the general formula (4) or (5) is derived from an aromatic ring-bearing cyclic olefin.

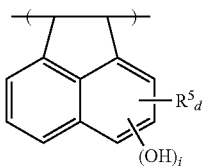
(4)

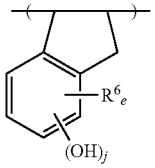
(5)

When a resist film of a resist composition based on a polymer comprising recurring units of formula (1), recurring units of at least one type selected from formulae (2) and (3), and recurring units of at least one type selected from formulae (4) and (5) is exposed to a pattern of EB or EUV including both isolated feature and isolated space portions, the resist composition is successful in fully suppressing the size shift between the irradiated pattern and the formed pattern and establishing a high resolution at the same time.

In formulae (4) and (5), $R^5$ and d, and $R^6$ and e are as defined for $R^2$ and a in formula (1), respectively. Preferred examples are the same as enumerated above.

From a relationship to the other recurring units, units of formula (4) or (5) wherein i or j is at least 1 may be used for enhancing the alkali dissolution of the polymer. In such a case, the following derivatives are preferably used to attain the desired effect while they are readily available.

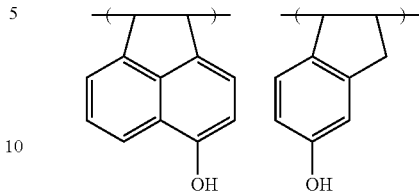

In the polymer, at least one of the recurring units other than formula (1) should have a phenolic hydroxyl unit and/or fluoroalcohol unit. The sum of the recurring units other than formula (1), i.e., the sum of units (a1), (a2), (a3), (2), (3), (4) and (5) preferably accounts for 25 to 95 mol %, more preferably 40 to 90 mol % based on the overall recurring units of the polymer.

The polymer used in the negative resist composition is dissolvable in an aqueous alkaline developer. The recurring units of formula (2) wherein g≥1, recurring units of formula (3), recurring units of formula (4) wherein i≥1, and recurring units of formula (5) wherein j≥1 constitute a class of recurring units contributing to alkaline solubility and substrate adhesion. Then the total of recurring units belonging to this class should preferably account for 25 to 95 mol %, more preferably 40 to 80 mol % based on the overall recurring units of the polymer. Notably, if the sum of recurring units of formula (4) wherein i≥1 and recurring units of formula (5) wherein j≥1 accounts for more than half the total of recurring units belonging to this class, the total of recurring units belonging to this class should preferably be at least 40 mol % based on the overall recurring units of the polymer. If the sum of recurring units of formula (2) wherein g≥1 and recurring units of formula (3) accounts for at least 20 mol % based on the overall recurring units of the polymer, the total of recurring units belonging to this class should preferably be up to 80 mol % based on the overall recurring units of the polymer. If the total of recurring units belonging to this class is below the lower limit, there is a likelihood of scumming upon development and bridging between resist pattern features. A high resolution is readily achieved when recurring units of formula (2) wherein g≥1 account for 50 to 70 mol % based on the overall recurring units of the polymer.

Advantages of the negative resist composition are attributable to the negative working function of the hydroxyl group in the recurring unit of formula (1) which undergoes elimination reaction under the action of acid. To exert this effect, the recurring units of formula (1) should preferably account for 5 to 75 mol %, more preferably 10 to 60 mol %, based on the overall recurring units of the polymer. If the content of recurring units of formula (1) is less than 5 mol %, a change of alkaline solubility due to acid-catalyzed reaction of recurring units of formula (1) is insufficient, failing to achieve the desired effect.

To give the polymer an appropriate allowance for thermal vibration, the sum of recurring units of formulae (4) and (5) is preferably 3 to 30 mol %, more preferably 5 to 20 mol % based on the overall recurring units of the polymer.

Also the recurring units capable of generating acid upon exposure as represented by formulae (a1), (a2) and (a3) are preferably incorporated in an amount of 0.5 to 20 mol %, more preferably 1 to 10 mol %. If the recurring units of formulae (a1), (a2) and (a3) are more than 20 mol %, then the polymer may become less soluble in the resist solvent, with the risk of defect formation.

Other recurring units may be incorporated in the polymer. Suitable recurring units which can be additionally incorporated include units having the general formulae (13), (14) and (15):

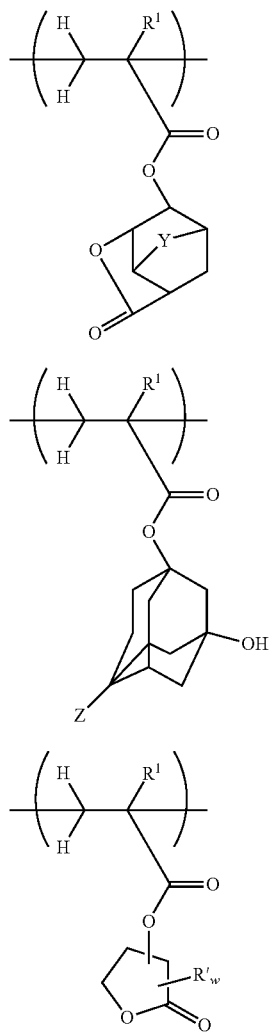

wherein $R^1$ is hydrogen, methyl or trifluoromethyl, Y is an oxygen atom or methylene group, Z is hydrogen or hydroxyl, R' is $C_1$-$C_4$ alkyl, and w is an integer of 0 to 3. Due to a lack of acidity, these units may be used as a supplemental unit for providing adhesion to substrates or adjusting solubility.

In summary, the polymer as component (A) should desirably comprise 5 to 75 mol %, more preferably 10 to 60 mol % of recurring units of formula (1), 0.5 to 20 mol %, more preferably 1 to 10 mol % of recurring units of formulae (a1) to (a3), 5 to 94.5 mol %, more preferably 15 to 86 mol % of recurring units of formula (2) and (3), 0 to 20 mol %, more preferably 3 to 15 mol % of recurring units of formula (4) and (5), and 0 to 20 mol %, more preferably 0 to 10 mol % of other recurring units.

In another embodiment, the negative resist composition may further comprise (C) an additional polymer comprising recurring units having the general formula (1), but free of recurring units having a site capable of generating an acid upon exposure to high-energy radiation. Typical of the additional polymer are polymers essentially comprising recurring units having formula (1), recurring units of at least one type selected from formulae (2) and (3), and recurring units of at least one type selected from formulae (4) and (5).

Specifically, the additional polymer as component (C) should desirably comprise 5 to 70 mol %, more preferably 10 to 60 mol % of recurring units of formula (1), 25 to 95 mol %, more preferably 40 to 80 mol % of recurring units of formula (2) and (3), 0 to 30 mol %, more preferably 3 to 20 mol % of recurring units of formula (4) and (5), and 0 to 20 mol %, more preferably 0 to 10 mol % of other recurring units.

When the additional polymer (C) is used in combination with the polymer (A), it becomes possible to adjust solubility in the resist solvent and solubility in the developer, and an improvement in resolution is sometimes achieved. The additional polymer (C) is blended in an amount of 0 to 5,000 parts, preferably 0 to 2,000 parts, and more preferably 0 to 1,000 parts by weight per 100 parts by weight of the polymer (A).

As the base polymer, a blend of different polymers (e.g., polymers A, or polymer A+ polymer C) may be used. When a blend is not used, a polymer may be designed by selecting recurring units each having one or more of the above functions, and determining a formulation ratio of individual recurring units so as to endow a resist film with the desired resolution.

The polymer (A) or (C) comprising a plurality of the recurring units defined above can be obtained in a standard way by performing copolymerization of corresponding monomers while combining protection and deprotection reactions if necessary. The preferred copolymerization reaction is radical polymerization, but not limited thereto. With respect to the polymerization reaction, reference may be made to Patent Document 3.

The polymer (A) or (C) preferably has a weight average molecular weight (Mw) of 1,000 to 50,000, and more preferably 1,000 to 20,000 as measured by GPC versus polystyrene standards. A polymer with a Mw of less than 1,000 may be reduced in resolution and form a pattern having a rounded top and degraded LER. A polymer with a Mw in excess of the range tends to increase LER, though depending on the pattern to be resolved. It is recommended to control the Mw of a polymer to 20,000 or less, particularly when a pattern having a line width of up to 100 nm is formed.

The polymer (A) or (C) preferably has a narrow dispersity as demonstrated by a molecular weight distribution Mw/Mn in the range of 1.0 to 3.0, more preferably 1.0 to 2.5. A broader dispersity may cause drawbacks to the pattern such as foreign matter after development and degraded profile.

In the negative resist composition, (D) a polymer comprising recurring units having the general formula (8), and fluorine-containing recurring units of at least one type selected from recurring units having the general formulae (9), (10), (11) and (12) may be added for the purpose of preventing chemical flare of acid upon exposure to high-energy radiation. In a process involving the step of coating an anti-charging film material onto the resist film, the polymer (D) is also effective for inhibiting mixing of any acid from the anti-charging film and thus preventing unexpected unnecessary negative working reaction. The inclusion of polymer (D) is also effective for increasing the dissolution rate of the unexposed region of resist film in alkaline developer and thus effective for reducing development defects.

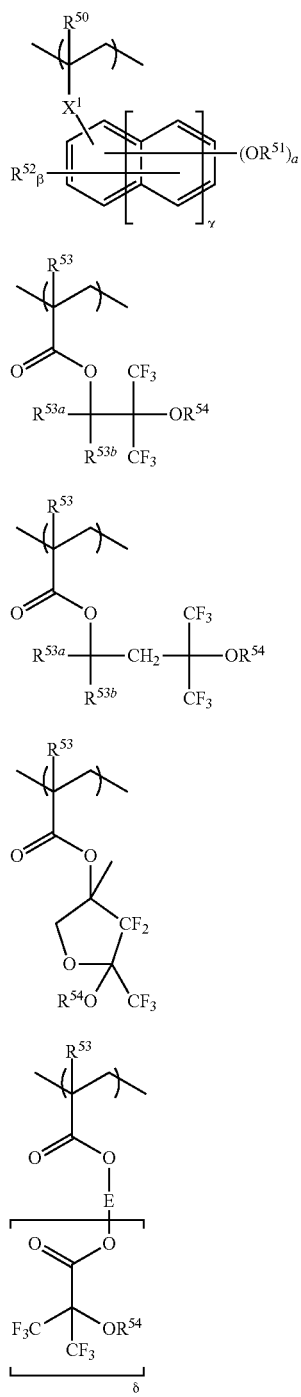

Herein $R^{50}$ is hydrogen or methyl, $R^{51}$ is hydrogen or a straight or branched $C_1$-$C_5$ monovalent hydrocarbon group which may be separated by a heteroatom, $R^{52}$ is a straight or branched $C_1$-$C_5$ monovalent hydrocarbon group which may be separated by a heteroatom, $R^{53}$ is each independently hydrogen, fluorine, methyl or trifluoromethyl, $R^{53a}$ and $R^{53b}$ are each independently hydrogen or a straight, branched or cyclic $C_1$-$C_{10}$ alkyl group, $R^{54}$ is each independently hydrogen, an acid labile group or a straight, branched or cyclic $C_1$-$C_{15}$ monovalent hydrocarbon or fluorinated hydrocarbon group in which an ether bond (—O—) or carbonyl moiety (—C(=O)—) may intervene in a carbon-carbon bond, α is an integer of 1 to 3, β is an integer in the range: 0≤β≤5+2γ-α, γ is 0 or 1, δ is an integer of 1 to 3, $X^1$ is a single bond, —C(=O)O— or —C(=O)NH—, and E is a straight, branched or cyclic $C_1$-$C_{20}$ (δ+1)-valent hydrocarbon or fluorinated hydrocarbon group.

Exemplary of the monovalent hydrocarbon group are alkyl, alkenyl and alkynyl groups, with the alkyl groups being preferred. Suitable alkyl groups include methyl, ethyl, n-propyl, isopropyl, n-butyl, isobutyl, sec-butyl, n-pentyl. In these groups, a heteroatom selected from oxygen, sulfur and nitrogen may intervene in a carbon-carbon bond.

In formula (8), the group: —$OR^{51}$ is preferably hydrophilic. In this case, $R^{51}$ is preferably hydrogen or a $C_1$-$C_5$ alkyl group whose carbon-carbon bond is separated by an oxygen atom.

Examples of the recurring unit having formula (8) are shown below, but not limited thereto.

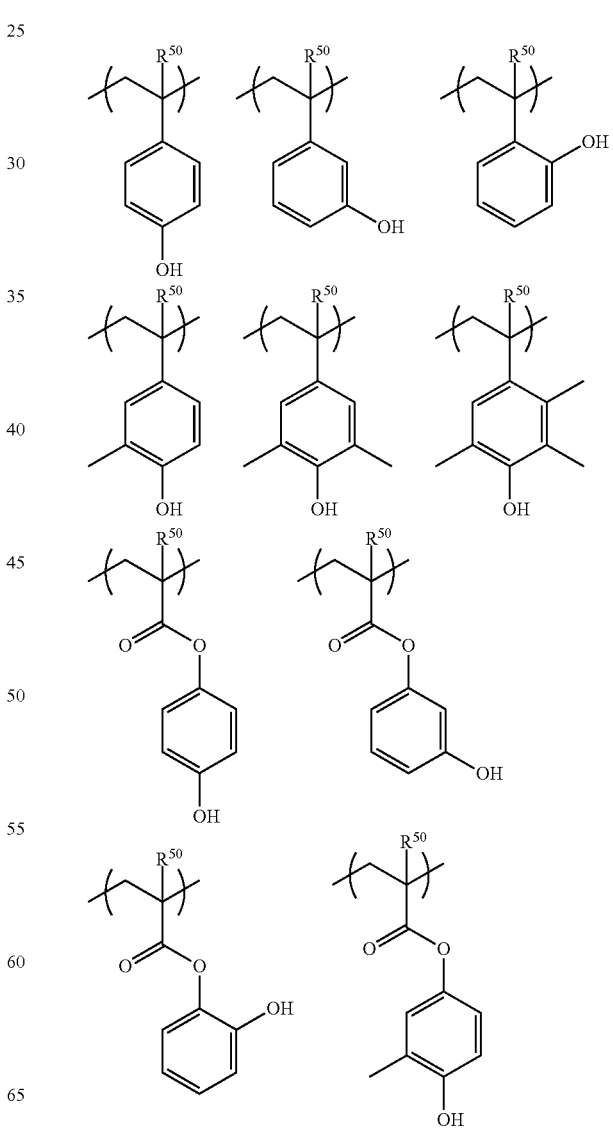

-continued
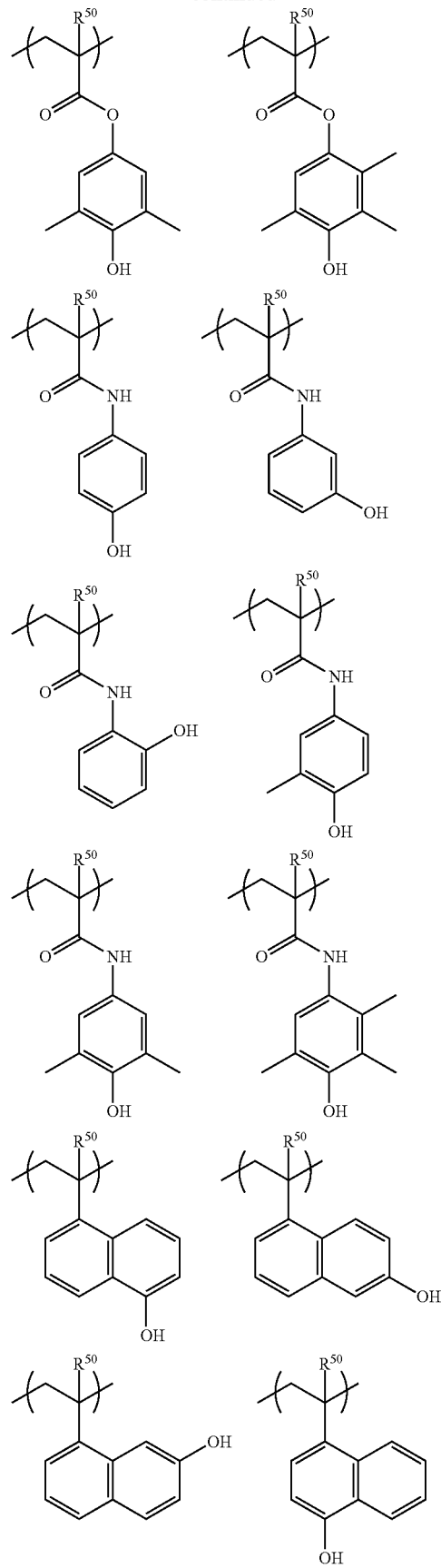
-continued
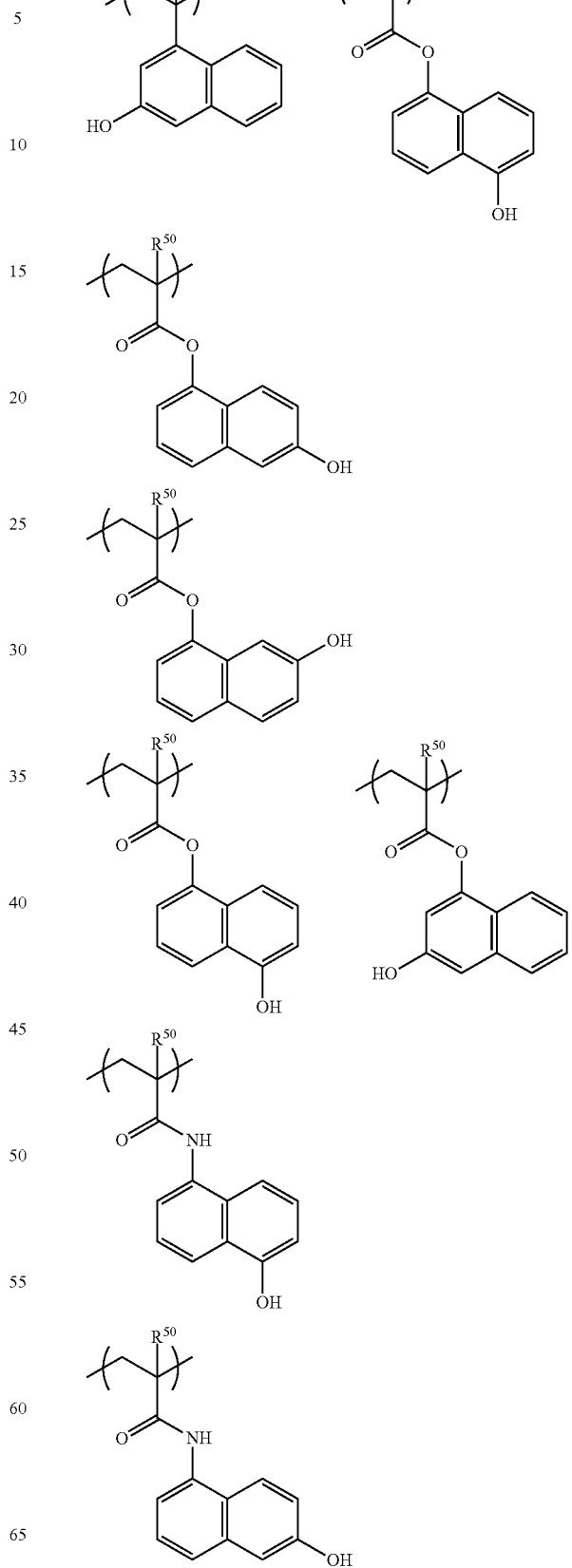

-continued

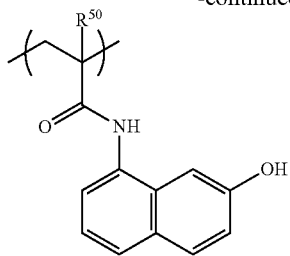

Notably R$^{50}$ is as defined above.

In the recurring unit having formula (8), X$^1$ is preferably —C(=O)O— or —C(=O)NH— rather than a single bond. Also preferably R$^{50}$ is hydrogen or methyl. Due to inclusion of a carbonyl moiety in X$_1$, an ability to trap the acid originating from the anti-charging film is improved. When R$^{50}$ is methyl, a rigid polymer having a higher glass transition temperature (Tg) is available, which is effective for suppressing acid diffusion. The resulting resist film has age stability sufficient to avoid the degradation of resolution and pattern profile.

The recurring units containing at least one fluorine atom are preferably units of at least one type selected from recurring units having formulae (9) to (12).

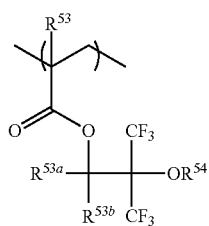

(9)

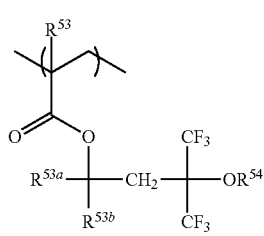

(10)

-continued

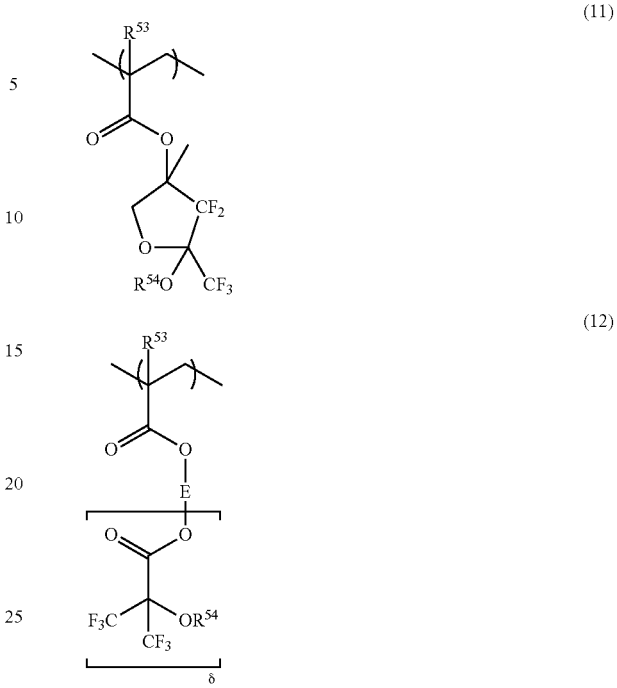

Herein R$^{53}$ is each independently hydrogen, fluorine, methyl or trifluoromethyl. R$^{53a}$ and R$^{53b}$ are each independently hydrogen or a straight, branched or cyclic C$_1$-C$_{10}$ alkyl group. R$^{54}$ is each independently hydrogen, a straight, branched or cyclic C$_1$-C$_{15}$ monovalent hydrocarbon group or monovalent fluorinated hydrocarbon group, or an acid labile group. When R$^{54}$ is a monovalent hydrocarbon group or monovalent fluorinated hydrocarbon group, an ether bond (—O—) or carbonyl moiety (—C(=O)—) may intervene in a carbon-carbon bond. E is a straight, branched or cyclic C$_1$-C$_{20}$ ($\delta$+1)-valent hydrocarbon or fluorinated hydrocarbon group, and 5 is an integer of 1 to 3.

Examples of the straight, branched or cyclic C$_1$-C$_{10}$ alkyl group include methyl, ethyl, n-propyl, isopropyl, cyclopropyl, n-butyl, isobutyl, sec-butyl, t-butyl, cyclobutyl, n-pentyl, cyclopentyl, n-hexyl, cyclohexyl, n-heptyl, n-octyl, n-nonyl, n-decyl, adamantyl, and norbornyl. Inter alia, the straight, branched or cyclic C$_1$-C$_6$ alkyl groups are preferred.

Exemplary of the straight, branched or cyclic C$_1$-C$_{15}$ monovalent hydrocarbon group are alkyl, alkenyl and alkynyl groups, with the alkyl groups being preferred. Suitable alkyl groups include n-undecyl, n-dodecyl, tridecyl, tetradecyl and pentadecyl as well as the aforementioned groups. Examples of the straight, branched or cyclic C$_1$-C$_{15}$ monovalent fluorinated hydrocarbon group include the foregoing examples of the monovalent hydrocarbon group in which one or more or even all carbon-bonded hydrogen atoms are substituted by fluorine atoms.

Examples of the straight, branched or cyclic C$_1$-C$_{20}$ ($\delta$+1)-valent hydrocarbon or fluorinated hydrocarbon group include the foregoing examples of the monovalent hydrocarbon or fluorinated hydrocarbon group, with the number ($\delta$) of hydrogen atoms being eliminated.

Examples of the recurring units having formulae (9) to (12) are shown below, but not limited thereto.

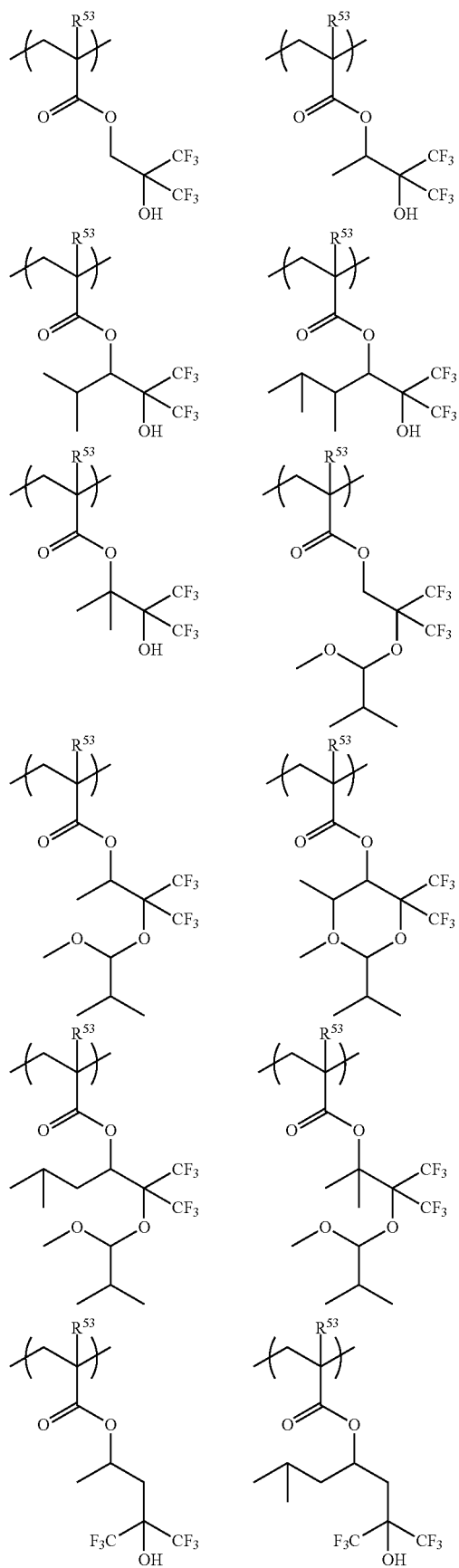
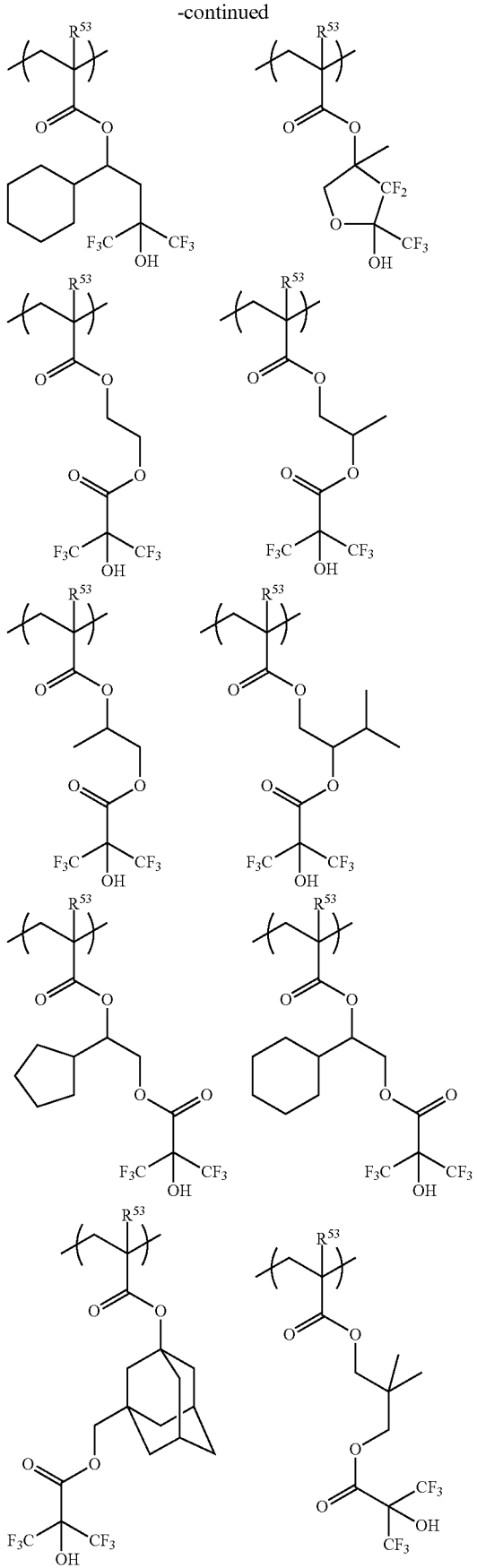

-continued

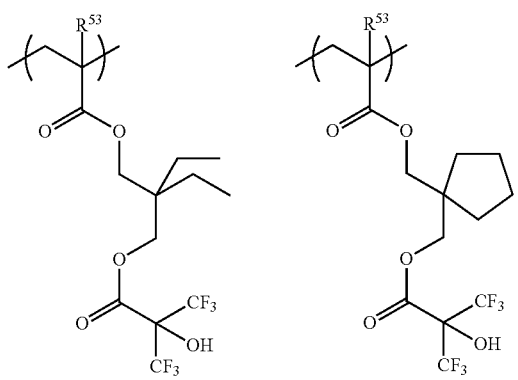

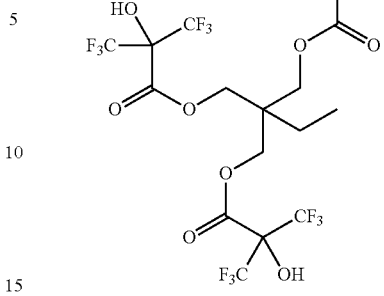

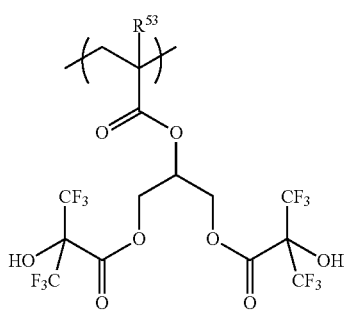

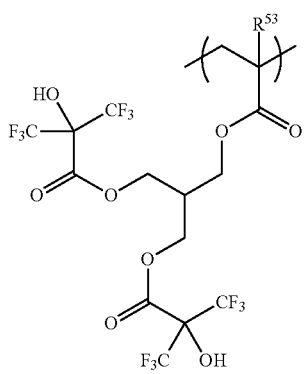

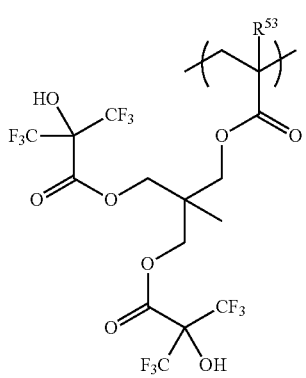

Herein $R^{53}$ is as defined above.

It is noted that the recurring units having formula (8) are incorporated in a range of 5 to 80 mol%, preferably 15 to 70 mol % based on the overall recurring units of the polymer (D). The recurring units having formulae (9) to (12) may be of one type or a mixture of two or more types. Preferably the recurring units having formulae (9) to (12) are incorporated in a range of 20 to 95 mol%, more preferably 30 to 85 mol % based on the overall recurring units of the polymer (D).

In addition to the foregoing units, the polymer (D) may further comprise other units, for example, units described in JP-A 2014-177407, paragraphs [0046] to [0078]. When the polymer (D) comprises other recurring units, the other recurring units are preferably incorporated in a range of up to 50 mol % based on the overall recurring units.

The polymer (D) may be prepared by any well-known techniques, by selecting suitable monomers and effecting copolymerlzation while optionally combining protection and deprotection reactions. The copolymerlzation reaction is preferably radical or anionic polymerization though not limited thereto. Reference may be made to JP-A 2004-115630.

The polymer (D) preferably has a weight average molecular weight (Mw) of 2,000 to 50,000, and more preferably 3,000 to 20,000, as measured by GPC versus polystyrene standards using tetrahydrofuran solvent. A polymer with a Mw of less than 2,000 may promote acid diffusion, degrade resolution or detract from age stability. A polymer with too high Mw is less soluble in the solvent and tends to cause coating defects. The polymer (D) should preferably have a dispersity (Mw/Mn) of 1.0 to 2.2, especially 1.0 to 1.7.

The polymer (D) is blended in an amount of 0 to 30 parts by weight, preferably 0.01 to 30 parts by weight, and more preferably 0.1 to 20 parts by weight per 100 parts by weight of the polymer (A) as base resin.

In most cases, a crosslinker is not added to the chemically amplified negative resist composition. If fine adjustment of performance is desired, however, a crosslinker may be added in an amount of 0.5 to 5 parts by weight per 100 parts by weight of the total of the polymers. Numerous crosslinkers for chemically amplified negative resist compositions are well known, as exemplified in Patent Documents 1 to 3.

Preferred examples of the crosslinker to foe separately added include alkoxymethylglycolurils and alkoxymethylmelamines such as tetramethoxymethylglycoluril, 1,3-bis-methoxymethyl-4,5-bismethoxyethyleneurea, bis-methoxymethylurea, hexamethoxymethylmelamine, and hexaethoxymethylmelamine. The crosslinkers may be used alone or in admixture.

It is not essentially necessary to add an acid generator to the negative resist composition because the polymer therein contains a site capable of generating acid upon exposure. However, an acid generator may be added for the purpose of adjusting sensitivity and resolution. When used, the acid generator is preferably added in an amount of 1 to 20 parts by weight, more preferably 2 to 15 parts by weight per 100 parts by weight of the total of the polymers. Any of well-known acid generators may be selected depending on physical properties to be adjusted. Suitable acid generators include sulfonium salts, iodonium salts, sulfonyldiazomethane, N-sulfonyloxyimide, and oxime-O-sulfonate acid generators, which may be used alone or in admixture.

Examples of the acid generator are described in JP-A 2008-111103, paragraphs [0122] to [0142] (U.S. Pat. No. 7,537,880). Of such exemplary acid generators, those of arylsulfonate type are preferred because they generate an acid having an appropriate strength for an acid-eliminatable group to undergo elimination reaction to induce alkali insolubilization by itself and crosslinking reaction between polymer molecules. Also the preferred PAG generates an acid having a pKa value in the range of −3.0 to 1.5, more preferably −1.0 to 1.5 because when the PAG is combined with the onium salt in the inventive resist composition, exchange reaction takes place to exert an effect of improving LER.

The preferred PAGs are compounds having a sulfonium anion of the structure shown below while a pairing cation may be any of the exemplary cations listed above for the sulfonium cations having formulae (a2) and (a3).

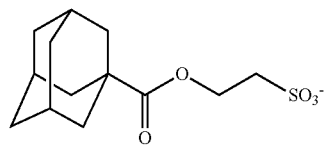
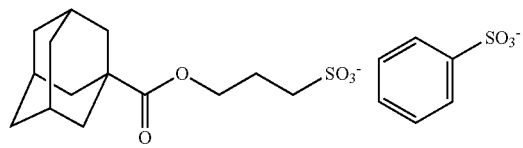
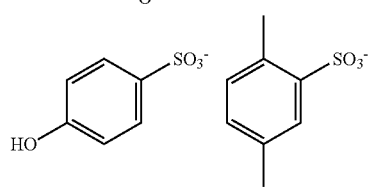
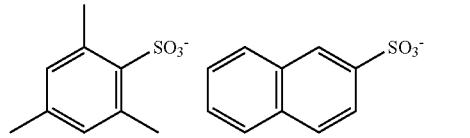
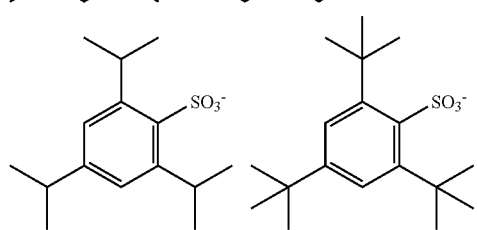

-continued

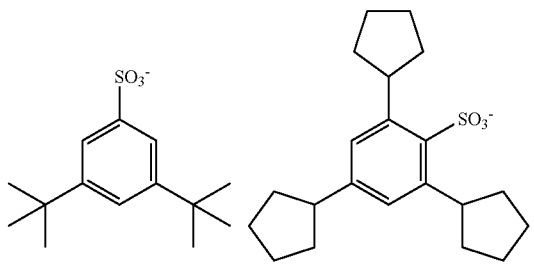
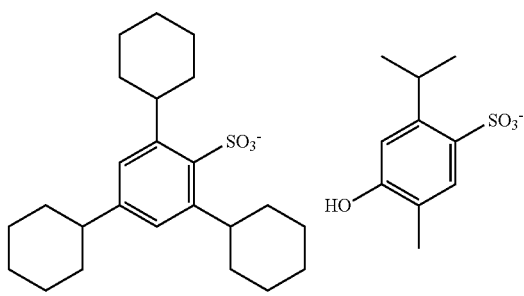
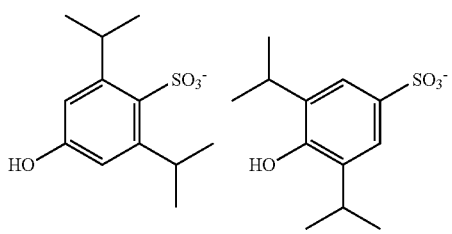
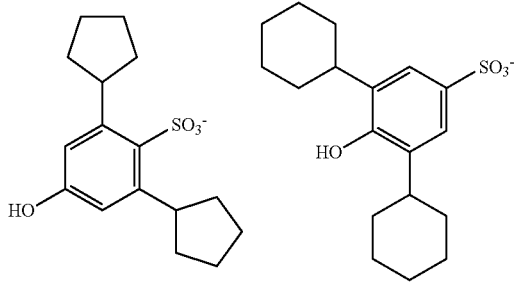
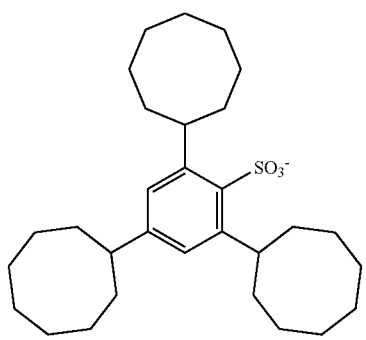

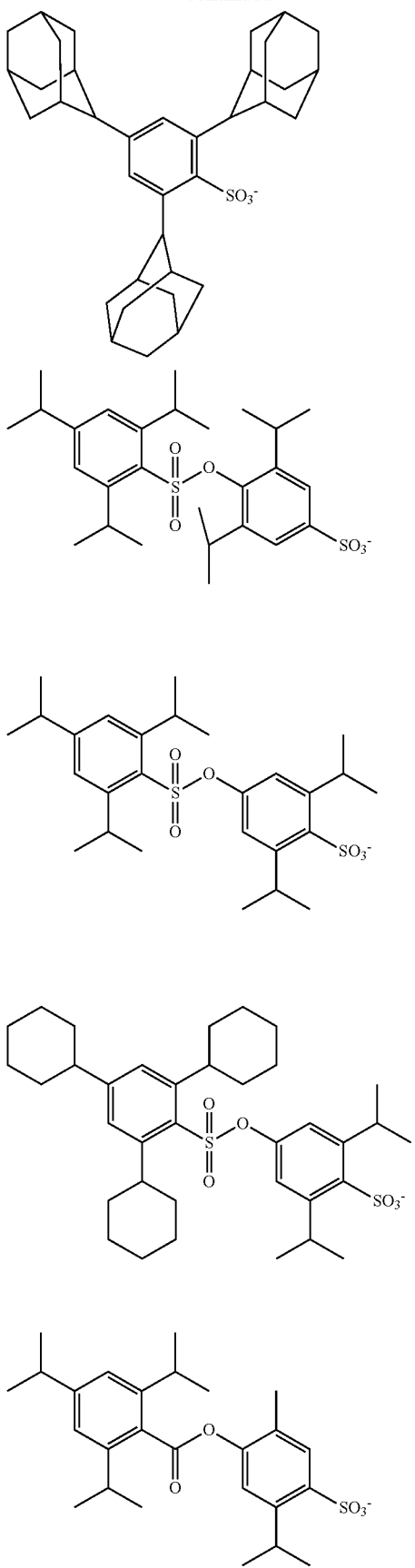
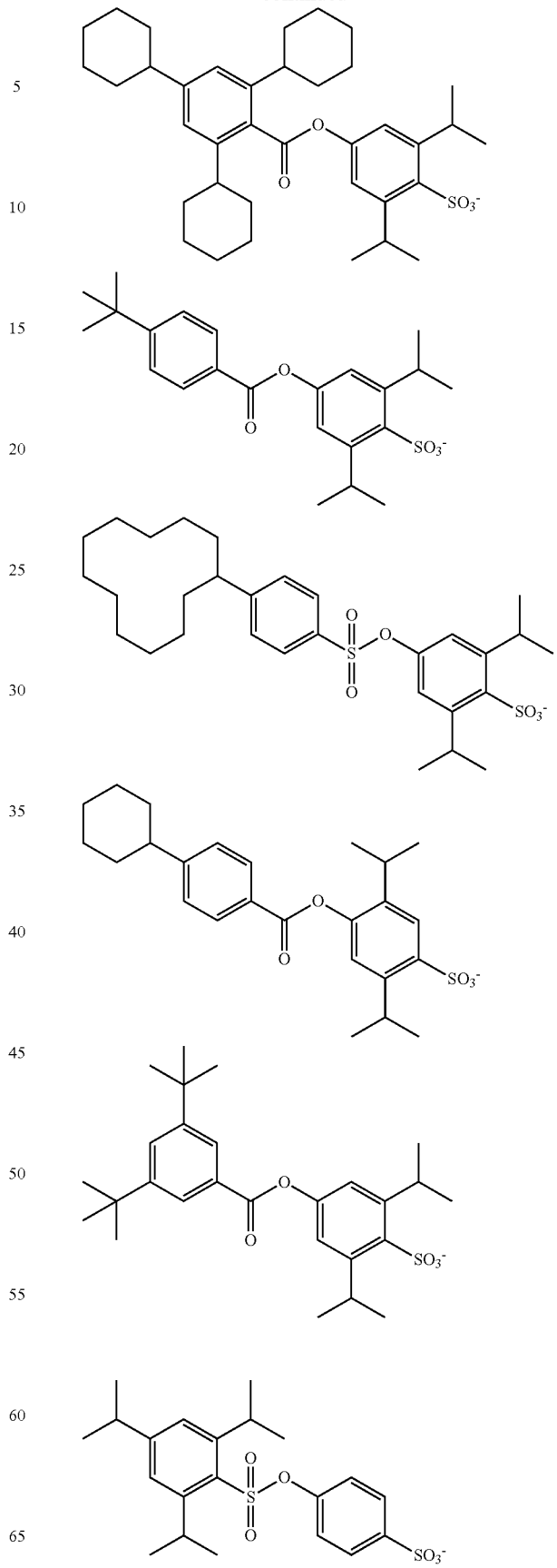

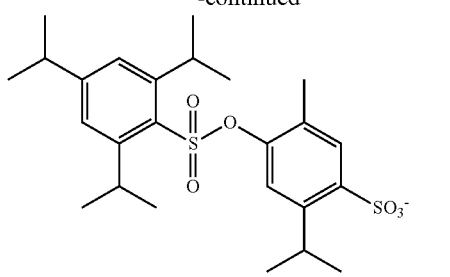
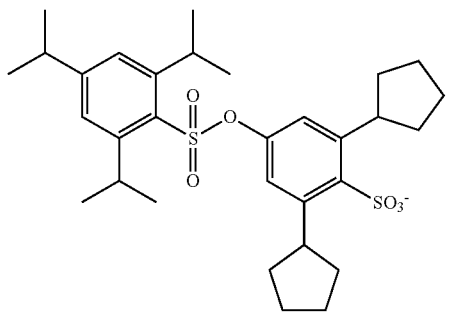
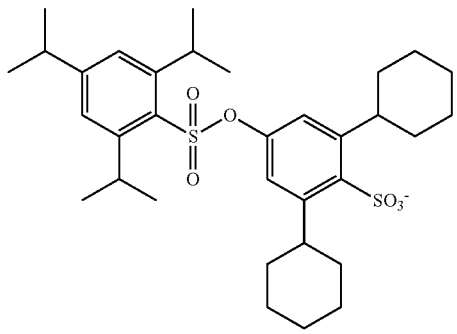
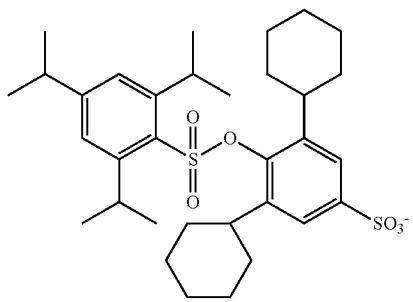
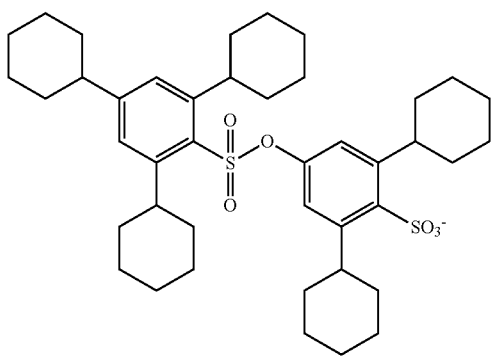
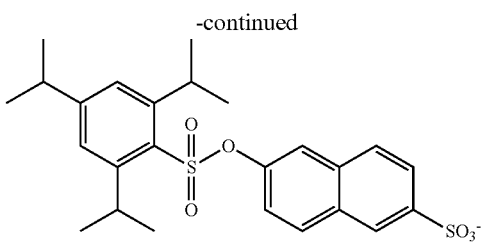
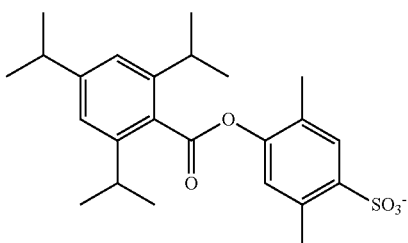
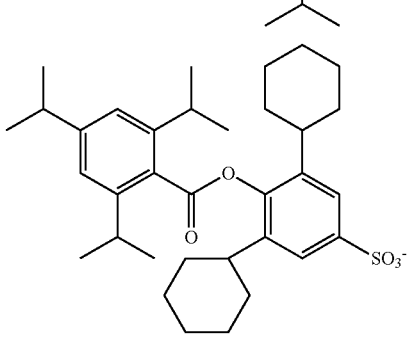
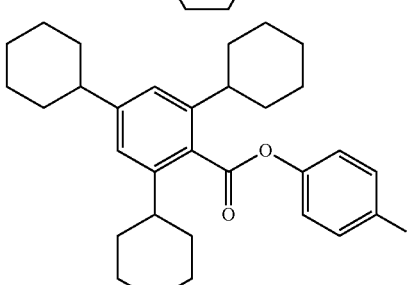
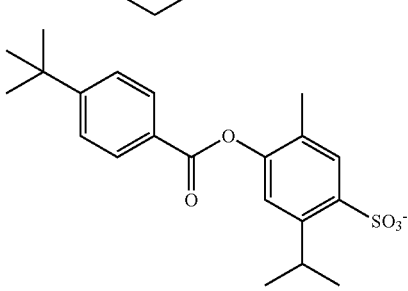
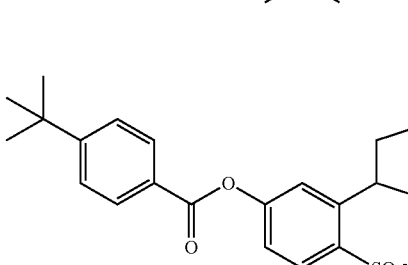

53
-continued
54
-continued
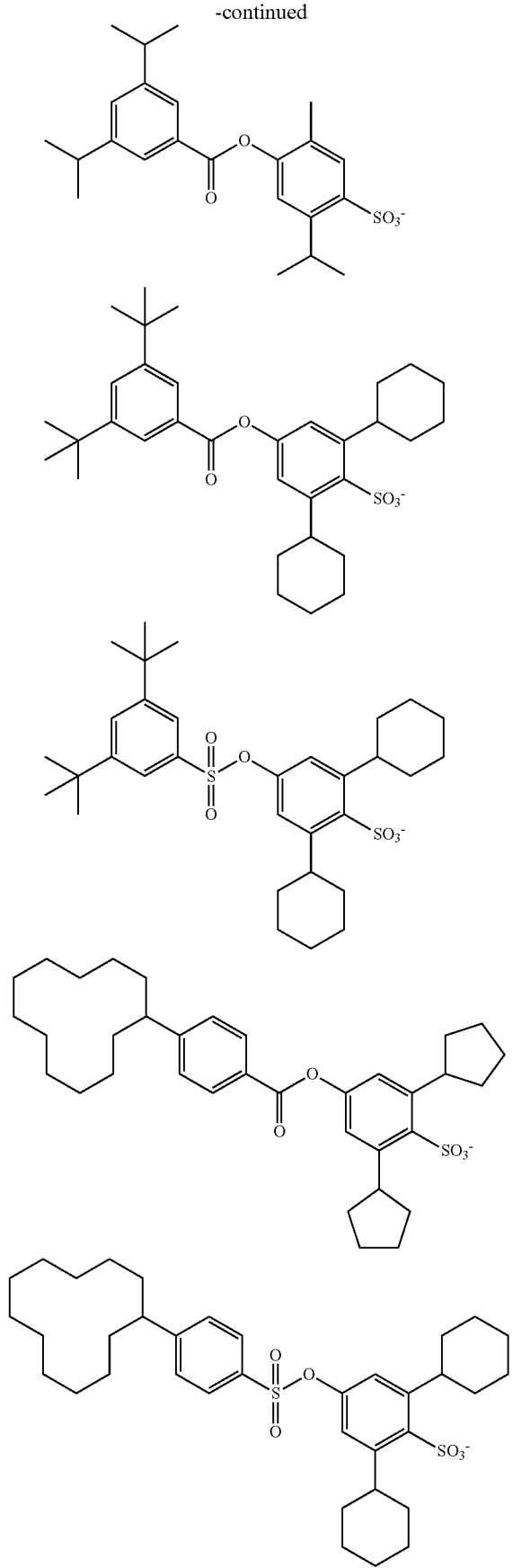
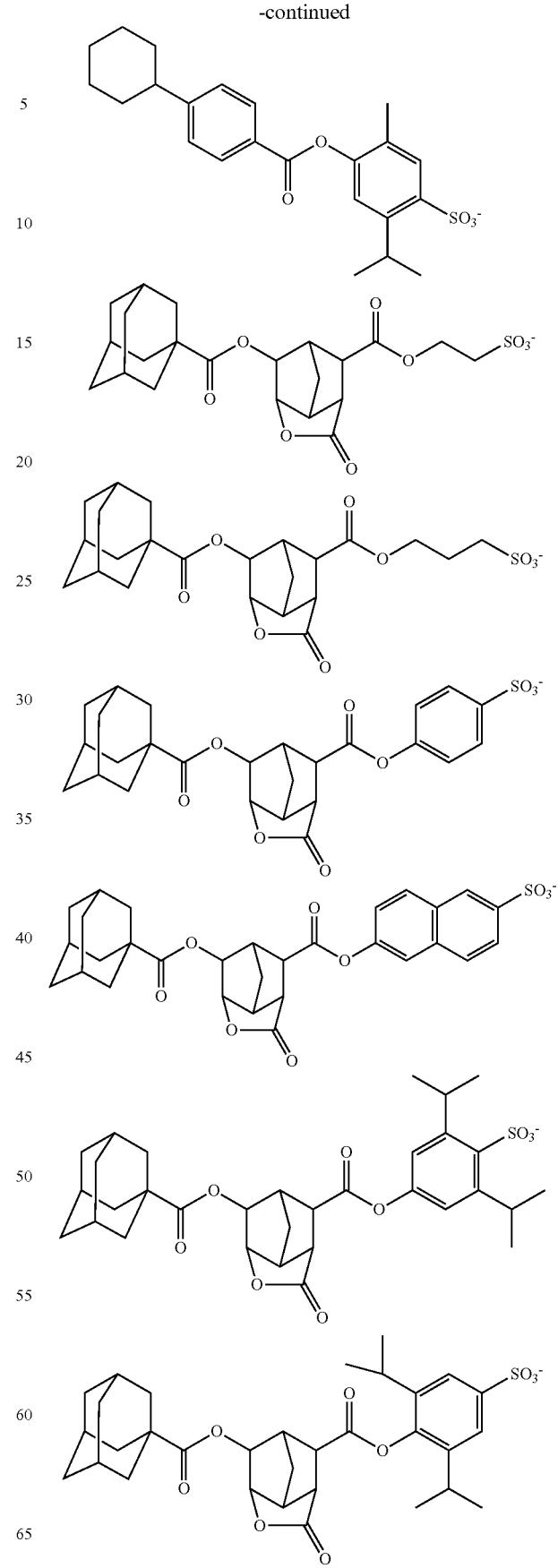

55
-continued
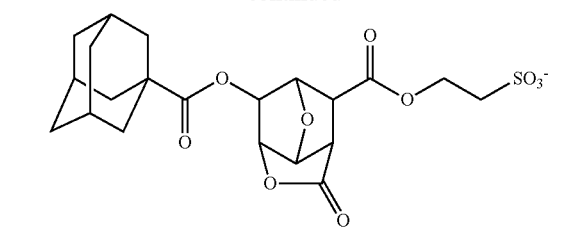
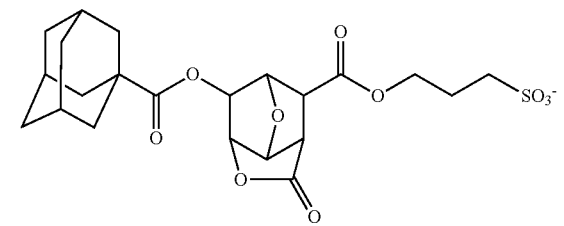
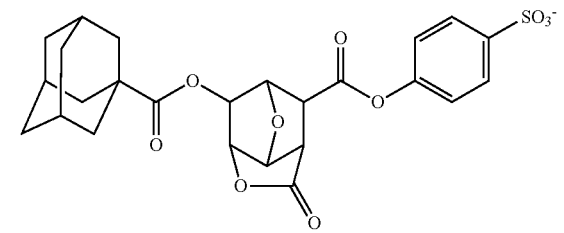
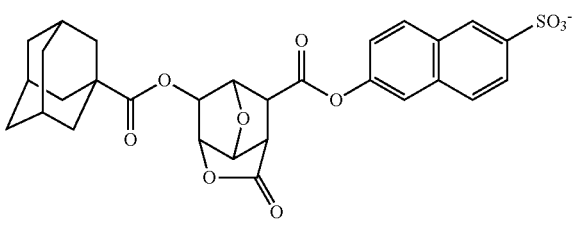
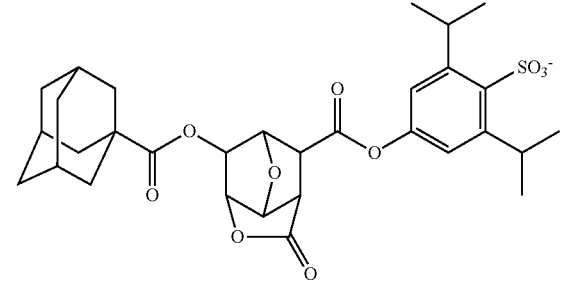
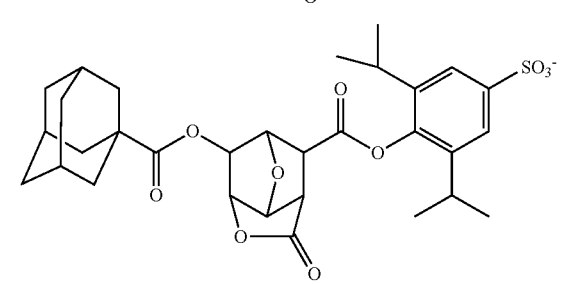
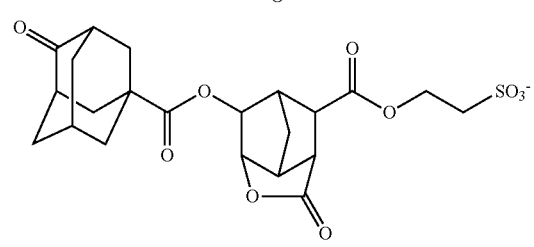
56
-continued
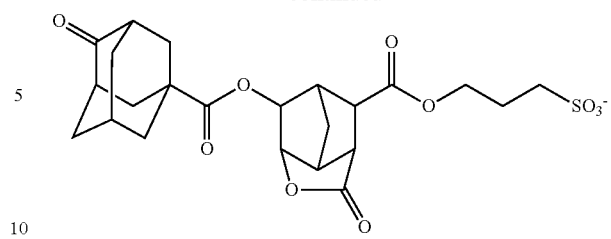
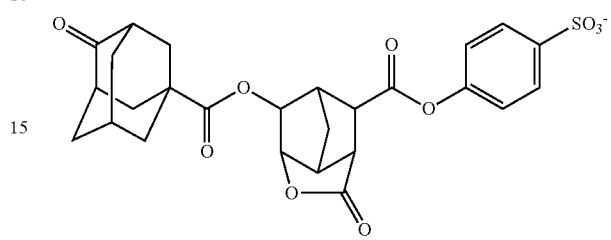
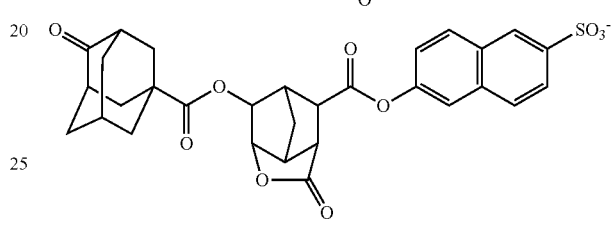
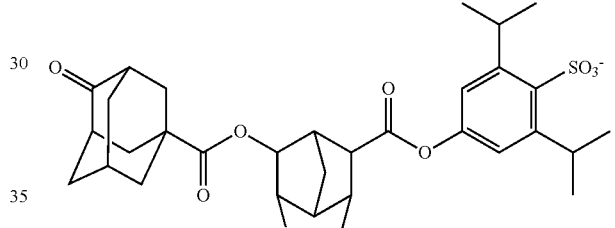
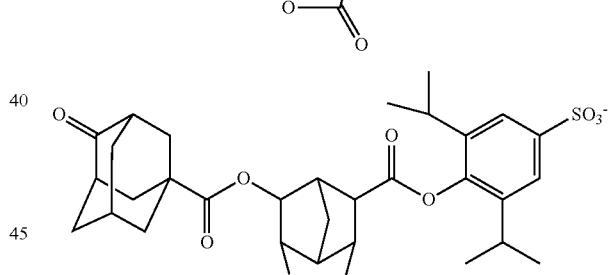
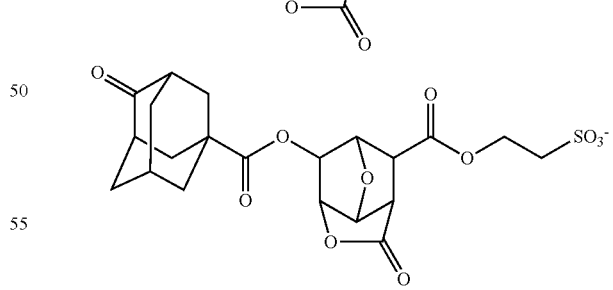
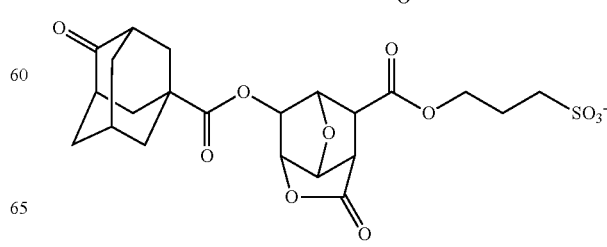

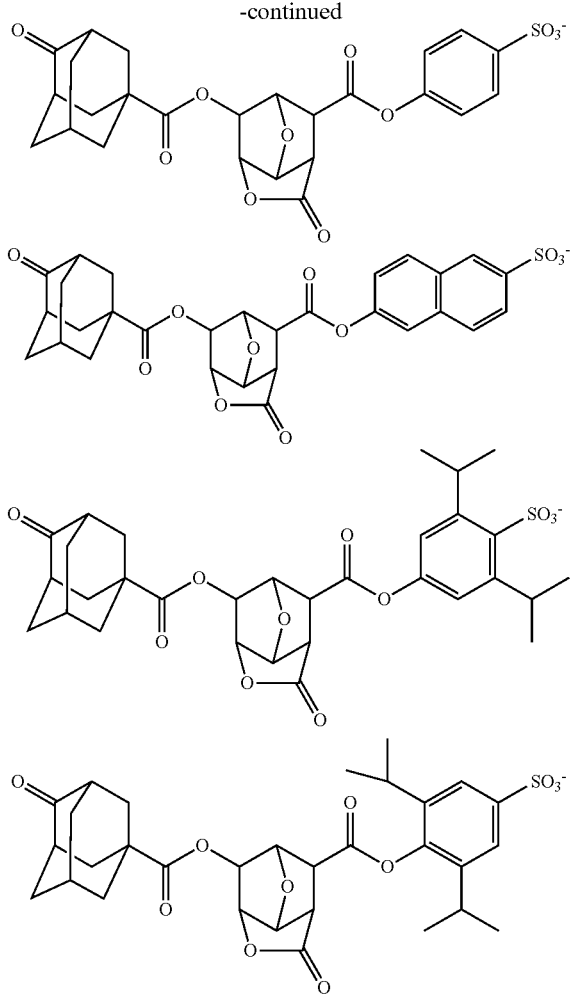

An acid diffusion regulator is, in fact, essential for sensitivity adjustment and resolution enhancement. While the carboxylic acid salt having formula (3a) as the acid diffusion regulator is present in the negative resist, composition, another basic compound may be added thereto. When added, the basic compound is typically used in an amount of 0.01 to 2:0 parts, more preferably 0.05 to 10 parts by weight per 100 parts by weight of the total of the polymers. A number of basic compounds are known as described in Patent Documents 1 to 5. Suitable basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Examples of these compounds are described in many patent documents including Patent Document 2, JP-A 2008-111103 (paragraphs [0146]-[0164]), and JP 3790649. Any basic compounds may be used alone or in admixture of two or more. Inter alia, tris(2-(methoxymethoxy)ethyl)amine, tris[2-(methoxymethoxy)ethyl]amine-N-oxide, morpholine derivatives, and imidazole derivatives are preferred.

To the resist composition, any of surfactants commonly used for improving coating characteristics may be added. A number of surfactants are well known as described in Patent Documents 1 to 5 and any suitable one may be selected therefrom. Besides, fluorine-containing polymers as described in Patent Document 13 may be added.

In the resist composition, the surfactant is preferably formulated in an amount of up to 2 parts, and more preferably up to 1 part by weight, per 100 parts by weight, of the overall polymers. When used, the surfactant is preferably added in an amount of at least 0.01 part by weight.

An organic solvent may be used in the preparation of the negative resist composition. It may be any of organic solvents in which the polymer, acid generator and other additives are dissolvable. Suitable organic solvents include, but are not limited to, ketones such as cyclohexanone and methyl n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in admixture. Of these solvents, ethyl lactate, propylene glycol monomethyl ether, PGMEA, and mixtures thereof are preferred because the acid generator is most soluble therein.

In the resist composition, the organic solvent is preferably used in an amount of 1,000 to 10,000 parts by weight, more preferably 2,000 to 9,700 parts by weight per 100 parts by weight of the overall polymers. When adjusted to such a concentration, the resist composition is applicable by a spin coating technique to form a resist film having a thickness of 10 to 300 nm and an improved flatness in a consistent manner.

If desired, any of well-known dissolution inhibitors may be added to the resist composition.

Process

Pattern formation using the negative resist composition of the invention may be performed by well-known lithography processes. The process generally involves coating, prebaking, exposure to high-energy radiation (typically EB or EDV), PEB, and development with alkaline developer. The resist composition is first applied onto a substrate for IC fabrication (silicon wafer having a surface layer of Si, $SiO_2$, SiN, SiON, TiN, WSi, BPSG, SOG, organic antireflective coating or the like) by a suitable coating technique such as spin coating. The coating is prebaked on a hot plate at a temperature of 60 to 150° C. for 1 to 10 minutes, preferably 80 to 140° C. for 1 to 5 minutes to form a resist film of 0.05 to 2.0 μm thick.

Then the resist film is exposed to high-energy radiation, such as deep UV, excimer laser, x-ray or EUV through a mask having a desired pattern. The exposure dose is preferably 1 to 200 mJ/cm², more preferably 10 to 100 mJ/cm². The exposure may be performed by conventional lithography whereas the immersion lithography of holding a liquid between the mask and the resist film may be employed if desired. In this case, a protective film which is insoluble in water may be applied on the resist film. The resist film is then baked (PEB) on a hot plate at 60 to 150° C. for 1 to 10 minutes, preferably 80 to 140° C. for 1 to 5 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

Where the processable substrate is a photomask blank, the resist composition is first applied onto a substrate for mask circuit fabrication (quartz substrate having a surface layer of Cr, CrO, CrQN, MoSi or the like). The coating is prebaked on a hot plate at a temperature of 80 to 130° C. for 4 to 20 minutes, preferably 90 to 110° C. for 8 to 12 minutes to form a resist film of 0.05 to 2.0 µm thick. The resist film is then subjected to pattern exposure in order to form the desired pattern in the film. Since the processing of a photomask blank is kept apart from the concept of fabrication of many identical products, a pattern is generally written on the resist film by the EB lithography. The resist film may be exposed to EB in a dose of 1 to 100 µC/cm$^2$, preferably 10 to 100 µC/cm$^2$. The resist film is then baked (PEB) on a hot plate at 60 to 150° C. for 0.1 to 5 minutes, preferably 80 to 140° C. for 0.5 to 3 minutes. Thereafter the resist film is developed with a developer in the form of an aqueous base solution, for example, 0.1 to 5 wt %, preferably 2 to 3 wt % aqueous solution of TMAH for 0.1 to 3 minutes, preferably 0.5 to 2 minutes by conventional techniques such as dip, puddle and spray techniques. In this way, a desired resist pattern is formed on the substrate.

Since the negative resist composition has very high etch resistance, it is useful in the application where resistance under severe etching conditions and a minimal LER are required. The resist composition is effectively applicable to a processable substrate, specifically a substrate having a surface layer of material to which a resist film is less adherent and which is likely to invite pattern stripping or pattern collapse, and particularly a substrate having sputter deposited thereon a surface layer material susceptible to pattern collapse, typically metallic chromium or a chromium compound containing at least one light element selected from oxygen, nitrogen and carbon. Substrates of this nature are often used in photomask blanks, and the invention is effective for pattern formation on these substrates.

EXAMPLE

Synthesis Examples, Examples, and Comparative Examples are given below by way of illustration and not by way of limitation. The average molecular weights including Mw and Mn are determined by GPC versus polystyrene standards, from which a dispersity (Mw/Mn) is computed. The compositional ratio of a copolymer is on a molar basis.

Synthesis Example 1

Synthesis of Polymer 1

In a 3000-mL dropping funnel under nitrogen blanket, a solution was prepared by dissolving 890 g of 50.0 wt % PGMEA solution of 4-hydroxystyrene, 47.7 g of acenaphthylene, 169.6 g of 4-(2-hydroxy-2-propyl)styrene, 87.0 g of triphenylsulfonium 1,1,3,3,3-pentafluoro-2-methacryloyloxy-propane-1-sulfonate, and 96.1 g of dimethyl 2,2'-azobis(2-methylpropionate) (V601, Wako Pure Chemical Industries, Ltd.) in 360 g of γ-butyrolactone and 220 g of PGMEA as solvent. A 5000-mL polymerization flask was purged with nitrogen, charged with 580 g of γ-butyrolactone, and heated at 80° C. In this state, the solution was added dropwise to the flask over 4 hours. After the completion of dropwise addition, stirring was continued for 18 hours while maintaining the polymerization temperature of 80° C., The polymerization solution was then cooled down to room temperature and added dropwise to 22,500 g of diisopropyl ether whereupon a copolymer agglomerated. The diisopropyl ether was decanted off, after which the copolymer was dissolved in 2,250 g of acetone. The acetone solution was added dropwise to 22,500 g of diisopropyl ether whereupon the copolymer precipitate was collected by filtration. The copolymer was dissolved in 2,250 g of acetone again. The acetone solution was added dropwise to 22,500 g of water, whereupon the copolymer precipitate was collected by filtration and dried at 40° C. for 40 hours, obtaining 700 g of a white polymer, designated Polymer 1. The polymer was analyzed by $^{13}$C-NMR, $^1$H-NMR, and GPC, with the results shown below.

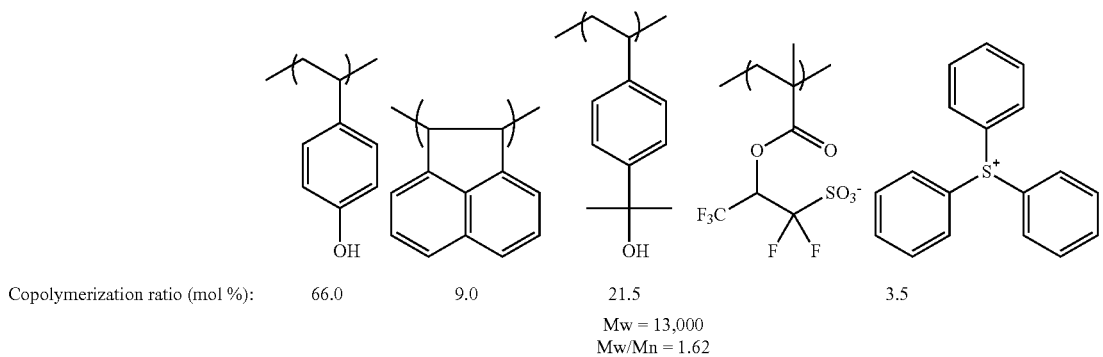

Copolymerization ratio (mol %):   66.0   9.0   21.5   3.5

Mw = 13,000
Mw/Mn = 1.62

Synthesis Example 2

Synthesis of Polymers 2 to 14 and Comparative Polymers 1, 2

Polymers 2 to 14 and Comparative Polymers 1, 2 shown in Table 1 were synthesized by the same procedure as Synthesis Example 1 except that the type and amount of monomers were changed. In Table 1, a ratio of each unit incorporated is on a molar basis. Recurring units incorporated in polymers have the structures shown in Tables 2 to 5.

TABLE 1
|  |  | Unit 1 | | Unit 2 | | Unit 3 | | Unit 4 | |
|---|---|---|---|---|---|---|---|---|---|
|  |  | Type | Ratio (mol %) | Type | Ratio (mol %) | Type | Ratio (mol %) | Type | Ratio (mol %) |
| Polymer | 1 | A-1 | 66.0 | B-2 | 9.0 | C-1 | 21.5 | P-1 | 3.5 |
|  | 2 | A-2 | 66.0 | B-2 | 10.5 | C-1 | 20.0 | P-1 | 3.5 |
|  | 3 | A-1 | 63.0 | B-1 | 12.0 | C-1 | 21.5 | P-1 | 3.5 |
|  | 4 | A-2 | 63.0 | B-1 | 12.0 | C-1 | 21.5 | P-1 | 3.5 |
|  | 5 | A-1 | 68.0 | B-2 | 10.0 | C-1 | 18.5 | P-2 | 3.5 |
|  | 6 | A-1 | 67.0 | B-2 | 9.5 | C-1 | 20.0 | P-3 | 3.5 |
|  | 7 | A-1 | 69.0 | B-2 | 10.0 | C-1 | 17.5 | P-4 | 3.5 |
|  | 8 | A-1 | 65.0 | B-2 | 9.5 | C-1 | 22.0 | P-5 | 3.5 |
|  | 9 | A-1 | 64.0 | B-2 | 10.0 | C-1 | 22.5 | P-6 | 3.5 |
|  | 10 | A-1 | 65.0 | B-3 | 10.0 | C-1 | 21.5 | P-1 | 3.5 |
|  | 11 | A-2 | 62.0 | B-4 | 10.0 | C-1 | 24.5 | P-3 | 3.5 |
|  | 12 | A-1 | 68.5 | B-2 | 8.0 | C-2 | 20.0 | P-1 | 3.5 |
|  | 13 | A-1 | 70.5 | B-2 | 8.0 | C-3 | 18.0 | P-1 | 3.5 |
|  | 14 | A-1 | 71.5 | B-2 | 9.0 | C-4 | 16.0 | P-1 | 3.5 |
TABLE 1-continued
|  |  | Unit 1 | | Unit 2 | | Unit 3 | | Unit 4 | |
|---|---|---|---|---|---|---|---|---|---|
|  |  | Type | Ratio (mol %) | Type | Ratio (mol %) | Type | Ratio (mol %) | Type | Ratio (mol %) |
| Comparative Polymer | 1 | A-1 | 75.5 | B-2 B-5 | 9.0 12.0 | — | — | P-1 | 3.5 |
|  | 2 | A-1 | 74.0 | B-1 B-5 | 10.5 12.0 | — | — | P-1 | 3.5 |
TABLE 2
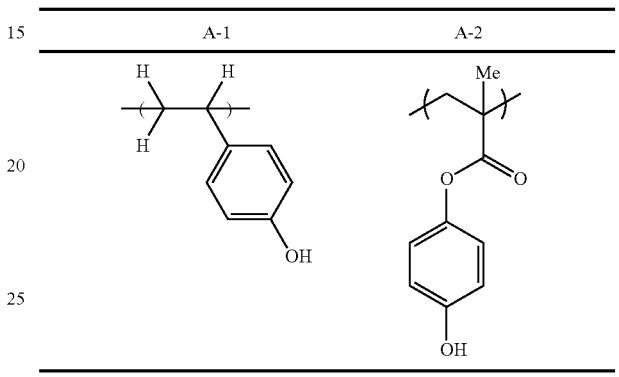
TABLE 3
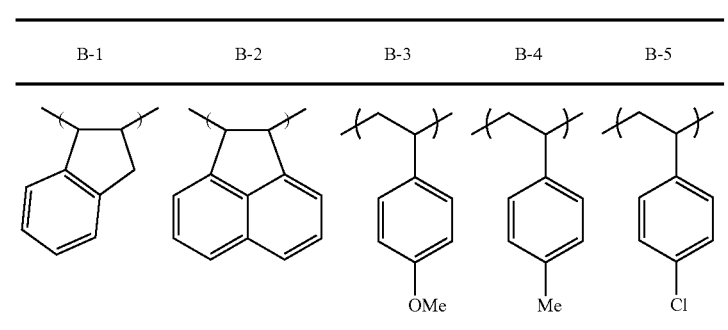
TABLE 4
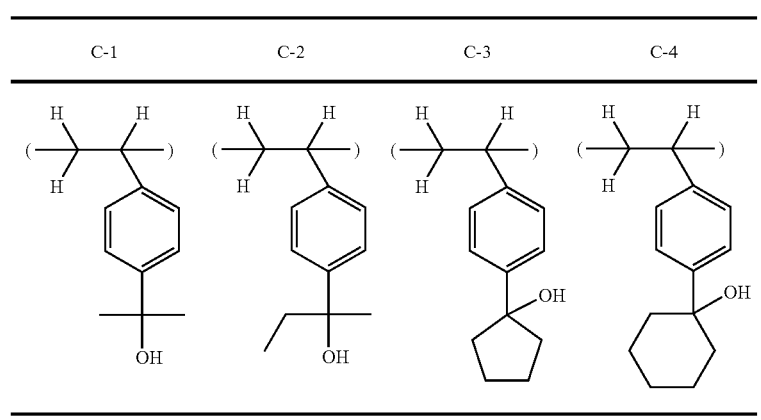

TABLE 5
P-1
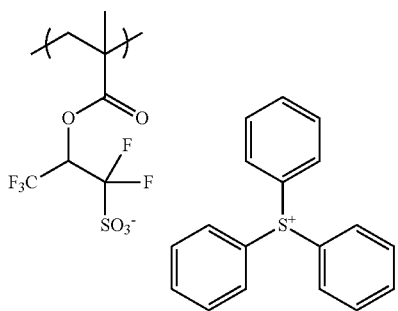
P-2
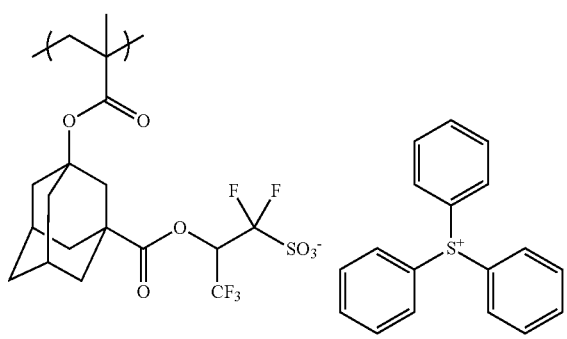
P-3
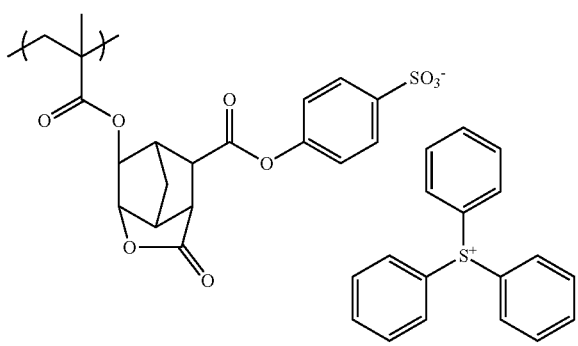
P-4
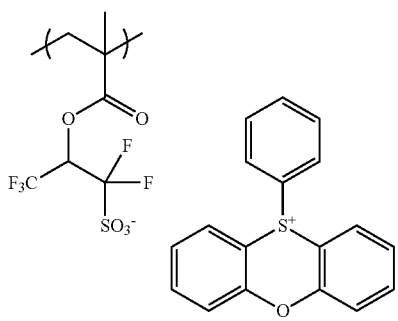
P-5

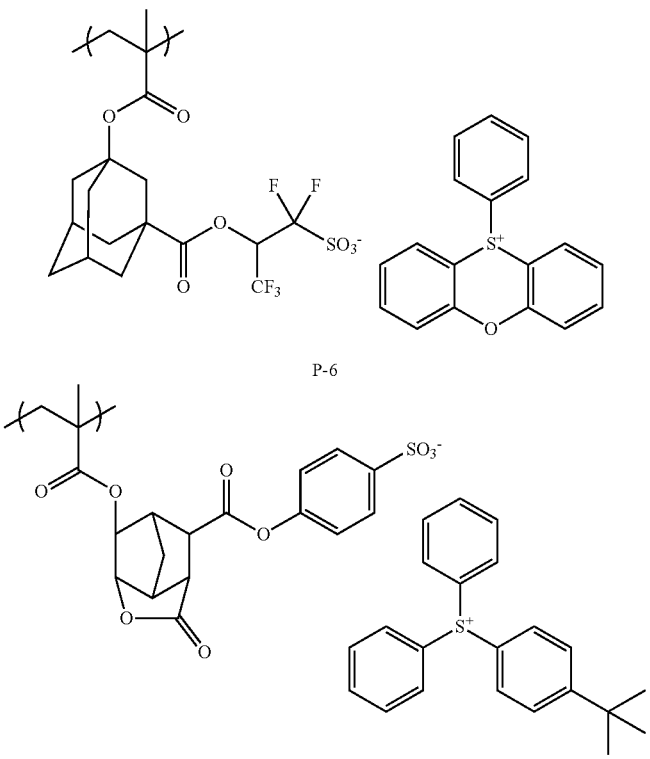

P-6

Synthesis Example 3

Synthesis of Polymer 15

In a 200-mL dropping funnel under nitrogen blanket, a solution was prepared by dissolving 39.26 g of 4-acetoxystyrene, 6.14 g of acenaphthylene, 19.6 g of 4-(2-hydroxy-2-propyl)styrene, and 7.43 g of dimethyl 2,2'-azobis(2-methylpropionate) (V601, Wako Pure Chemical Industries, Ltd.) in 90 g of methyl ethyl ketone (MEK) as solvent. A 500-mL polymerization flask was purged with nitrogen, charged with 60 g of MEK, and heated at 80° C. In this state, the solution was added dropwise to the flask over 4 hours. After the completion of dropwise addition, stirring was continued for 18 hours while maintaining the polymerization temperature of 80° C. The polymerization solution was then cooled down to room temperature and added dropwise to 1,000 g of hexane whereupon a copolymer precipitated. The copolymer precipitate was collected by filtration and washed twice with 200 g of hexane. Under nitrogen blanket, the copolymer was dissolved in a mixture of 126 g of THF and 42 g of methanol in a 1-L flask, to which 16.3 g of ethanol amine was added and stirred at 60° C. for 3 hours. The reaction solution was concentrated in a reduced pressure, the concentrate was dissolved in a mixture of 300 g of ethyl acetate and 80 g of water. The resulting solution was transferred to a separatory funnel, to which 8.2 g of acetic acid was added, followed by separatory operation. After the lower layer was distilled off, 80 g of water and 10.9 g of pyridine were added to the organic layer, followed by separatory operation. After the lower layer was distilled off, 80 g of water was added to the organic layer, followed by water washing and separatory operation. The water washing and separatory operation was repeated 5 times in total. The organic layer after separation was concentrated, and the concentrate was dissolved in 140 g of acetone. The acetone solution was added dropwise to 2,500 g of water whereupon the crystallized precipitate was collected by filtration, washed with water, and suction filtered for 2 hours. The mass collected by filtration was dissolved in 150 g of acetone again. The acetone solution was added dropwise to 2,800 g of water. The crystallized precipitate was filtered, washed with water, and dried, yielding 45.0 g of a white polymer, designated Polymer 15. The polymer was analyzed by $^{13}$C-NMR, $^1$H-NMR, and GPC, with the results shown below.

Copolymerization ratio (mol %): 60.0 / 10.0 / 30.0

Mw = 3,500
Mw/Mn = 1.58

Synthesis Example 4

Synthesis of Polymer 16

In a 200-mL dropping funnel under nitrogen blanket, a solution was prepared by dissolving 67.5 g of hydroquinone monomethacrylate, 8.87 g of acenaphthylene, 23.6 q of 4-(2-hydroxy-2-propyl)styrene, and 10.7 g of dimethyl 2,2′-azobis(2-methylpropionate) (V601, Wako Pure Chemical Industries, Ltd.) in 120 g of methyl ethyl ketone (MEK) as solvent. A 500-mL polymerization flask was purged with nitrogen, charged with 60 g of MEK, and heated at 80° C. In this state, the solution was added dropwise to the flask over 4 hours. After the completion of dropwise addition, stirring was continued for 18 hours while maintaining the polymerization temperature of 80° C. The polymerization solution was then cooled down to room temperature and added dropwise to 2,000 g of hexane whereupon a copolymer precipitated. The copolymer precipitate was collected by filtration and washed twice with 400 g of hexane. The copolymer was filtered and dried, yielding 45.0 g of a white copolymer, designated Polymer 16. The polymer was analyzed by $^{13}$C-NMR, $^{1}$H-NMR, and GPC, with the results shown below.

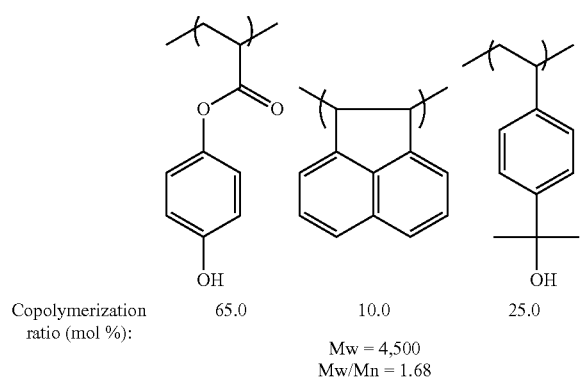

Copolymerization ratio (mol %): 65.0  10.0  25.0

Mw = 4,500
Mw/Mn = 1.68

Synthesis Example b

Synthesis of Polymers 17 to 24 and Comparative Polymers 3, 4

Polymers 17 to 24 and Comparative Polymers 3, 4 shown in Table 6 were synthesized by the same procedure as above except that the type and amount of monomers were changed, specifically the same procedure as Polymer 15 where units (A-1) are incorporated in the polymer or the same procedure as Polymer 16 where units (A-2) are incorporated in the polymer. In Table 6, a ratio of each unit incorporated is on a molar basis. Recurring units incorporated in polymers have the structures shown in Tables 2 to 5.

TABLE 6

|  |  | Unit 1 | | Unit 2 | | Unit 3 | |
|---|---|---|---|---|---|---|---|
|  |  | Type | Ratio (mol %) | Type | Ratio (mol %) | Type | Ratio (mol %) |
| Polymer | 15 | A-1 | 60.0 | B-2 | 10.0 | C-1 | 30.0 |
|  | 16 | A-2 | 65.0 | B-2 | 10.0 | C-1 | 25.0 |
|  | 17 | A-1 | 60.0 | B-1 | 13.0 | C-1 | 27.0 |
|  | 18 | A-1 | 55.0 | B-3 | 15.0 | C-1 | 30.0 |
|  | 19 | A-1 | 55.0 | B-4 | 15.0 | C-1 | 30.0 |
|  | 20 | A-1 | 65.0 | B-2 | 10.0 | C-2 | 25.0 |
|  | 21 | A-1 | 68.0 | B-2 | 9.0 | C-3 | 23.0 |

TABLE 6-continued

|  |  | Unit 1 | | Unit 2 | | Unit 3 | |
|---|---|---|---|---|---|---|---|
|  |  | Type | Ratio (mol %) | Type | Ratio (mol %) | Type | Ratio (mol %) |
|  | 22 | A-1 | 69.0 | B-2 | 9.0 | C-4 | 22.0 |
|  | 23 | A-2 | 63.0 | B-3 | 10.0 | C-1 | 27.0 |
|  | 24 | A-2 | 65.0 | B-4 | 10.0 | C-1 | 25.0 |
| Comparative Polymer | 3 | A-1 | 76.0 | B-1 | 12.0 | — | — |
|  |  |  |  | B-5 | 12.0 |  |  |
|  | 4 | A-1 | 70.0 | B-2 | 15.0 | — | — |
|  |  |  |  | B-5 | 15.0 |  |  |

Examples and Comparative Examples

Preparation of Negative Resist Compositions

Negative resist compositions were prepared by using the synthesized polymer (Polymers 1 to 24 or Comparative Polymers 1 to 4), and dissolving the polymer, an acid generator (PAG-1 to PAG-3), and a basic compound (Q-1 to Q-4 or Compar. Q-1, 2) in an organic solvent in accordance with the recipe shown in Tables 7 to 9. Each composition was filtered through a Teflon® filter having a pore size of 0.2 µm, thereby giving a negative resist composition solution.

Some solutions further contained tetramethoxymethylglycoluril (TMGU) as a crosslinker or fluorinated polymer FP-1 as additive. All the solutions further contained 0.075 pbw (relative to solids) of a surfactant PF-636 (Omnova Solutions, Inc.).

Fluorinated polymer FP-1 has the following structure.

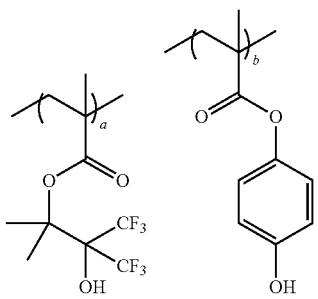

(a = 0.80, b = 0.20, Mw = 6,000)

In Tables 7 to 9, the solvents were propylene glycol monomethyl ether acetate (PGMEA), ethyl lactate (EL), and propylene glycol monomethyl ether (PGME). The acid generator and basic compound have the structures shown in Tables 10 and 11.

TABLE 7

|  |  | Resin (pbw) | PAG (pbw) | Basic compound (pbw) | Additive (pbw) | Solvent 1 (pbw) | Solvent 2 (pbw) | Solvent 3 (pbw) |
|---|---|---|---|---|---|---|---|---|
| Example | 1 | Polymer 1 (80) | — | Q-1 (4.0) | — | PGMEA (1,080) | EL (1,080) | PGME (1,440) |
|  | 2 | Polymer 2 (80) | — | Q-1 (4.0) | — | PGMEA (1,080) | EL (1,080) | PGME (1,440) |
|  | 3 | Polymer 3 (80) | — | Q-1 (4.0) | — | PGMEA (1,080) | EL (1,080) | PGME (1,440) |
|  | 4 | Polymer 4 (80) | — | Q-1 (4.0) | — | PGMEA (1,080) | EL (1,080) | PGME (1,440) |
|  | 5 | Polymer 5 (80) | — | Q-1 (4.0) | — | PGMEA (1,080) | EL (1,080) | PGME (1,440) |
|  | 6 | Polymer 6 (80) | — | Q-1 (4.0) | — | PGMEA (1,080) | EL (1,080) | PGME (1,440) |
|  | 7 | Polymer 7 (80) | — | Q-1 (4.0) | — | PGMEA (1,080) | EL (1,080) | PGME (1,440) |
|  | 8 | Polymer 8 (80) | — | Q-1 (4.0) | — | PGMEA (1,080) | EL (1,080) | PGME (1,440) |
|  | 9 | Polymer 9 (80) | — | Q-1 (4.0) | — | PGMEA (1,080) | EL (1,080) | PGME (1,440) |
|  | 10 | Polymer 10 (80) | — | Q-1 (4.0) | — | PGMEA (1,080) | EL (1,080) | PGME (1,440) |
|  | 11 | Polymer 11 (80) | — | Q-1 (4.0) | — | PGMEA (1,080) | EL (1,080) | PGME (1,440) |
|  | 12 | Polymer 12 (80) | — | Q-1 (4.0) | — | PGMEA (1,080) | EL (1,080) | PGME (1,440) |
|  | 13 | Polymer 13 (80) | — | Q-1 (4.0) | — | PGMEA (1,080) | EL (1,080) | PGME (1,440) |
|  | 14 | Polymer 14 (80) | — | Q-1 (4.0) | — | PGMEA (1,080) | EL (1,080) | PGME (1,440) |
|  | 15 | Polymer 1 (80) | PAG-1 (5.0) | Q-1 (5.0) | — | PGMEA (1,080) | EL (1,080) | PGME (1,440) |
|  | 16 | Polymer 1 (80) | PAG-2 (5.0) | Q-1 (5.0) | — | PGMEA (1,080) | EL (1,080) | PGME (1,440) |
|  | 17 | Polymer 1 (80) | PAG-3 (5.0) | Q-1 (5.0) | — | PGMEA (1,080) | EL (1,080) | PGME (1,440) |
|  | 18 | Polymer 1 (80) | PAG-1 (5.0) | Q-2 (5.0) | — | PGMEA (1,080) | EL (1,080) | PGME (1,440) |
|  | 19 | Polymer 2 (80) | PAG-1 (5.2) | Q-3 (5.0) | — | PGMEA (1,080) | EL (1,080) | PGME (1,440) |
|  | 20 | Polymer 2 (80) | PAG-1 (5.0) | Q-4 (5.0) | — | PGMEA (1,080) | EL (1,080) | PGME (1,440) |

TABLE 8

|  |  | Resin (pbw) | PAG (pbw) | Basic compound (pbw) | Additive (pbw) | Solvent 1 (pbw) | Solvent 2 (pbw) | Solvent 3 (pbw) |
|---|---|---|---|---|---|---|---|---|
| Example | 21 | Polymer 1 (40) Polymer 15 (40) | — | Q-1 (4.0) | — | PGMEA (1,080) | EL (1,080) | PGME (1,440) |
|  | 22 | Polymer 1 (40) Polymer 15 (40) | PAG-1 (5.0) | Q-1 (5.0) | — | PGMEA (1,080) | EL (1,080) | PGME (1,440) |
|  | 23 | Polymer 2 (40) Polymer 16 (40) | PAG-1 (5.0) | Q-2 (5.0) | — | PGMEA (1,080) | EL (1,080) | PGME (1,440) |
|  | 24 | Polymer 2 (40) Polymer 16 (40) | PAG-1 (5.0) | Q-3 (5.0) | — | PGMEA (1,080) | EL (1,080) | PGME (1,440) |
|  | 25 | Polymer 1 (40) Polymer 15 (40) | PAG-2 (5.0) | Q-1 (5.0) | — | PGMEA (1,080) | EL (1,080) | PGME (1,440) |
|  | 26 | Polymer 1 (40) Polymer 15 (40) | PAG-3 (5.0) | Q-1 (5.0) | — | PGMEA (1,080) | EL (1,080) | PGME (1,440) |
|  | 27 | Polymer 2 (40) Polymer 16 (40) | PAG-1 (5.0) | Q-1 (5.0) | — | PGMEA (1,080) | EL (1,080) | PGME (1,440) |
|  | 28 | Polymer 3 (40) Polymer 17 (40) | PAG-1 (5.0) | Q-1 (5.0) | — | PGMEA (1,080) | EL (1,080) | PGME (1,440) |
|  | 29 | Polymer 10 (40) Polymer 18 (40) | PAG-1 (5.0) | Q-1 (5.0) | — | PGMEA (1,080) | EL (1,080) | PGME (1,440) |
|  | 30 | Polymer 11 (40) Polymer 19 (40) | PAG-1 (5.0) | Q-1 (5.0) | — | PGMEA (1,080) | EL (1,080) | PGME (1,440) |
|  | 31 | Polymer 12 (40) Polymer 20 (40) | PAG-1 (5.0) | Q-1 (5.0) | — | PGMEA (1,080) | EL (1,080) | PGME (1,440) |
|  | 32 | Polymer 13 (40) Polymer 21 (40) | PAG-1 (5.0) | Q-1 (5.0) | — | PGMEA (1,080) | EL (1,080) | PGME (1,440) |
|  | 33 | Polymer 14 (40) Polymer 22 (40) | PAG-1 (5.0) | Q-1 (5.0) | — | PGMEA (1,080) | EL (1,080) | PGME (1,440) |

TABLE 8-continued

| | Resin (pbw) | PAG (pbw) | Basic compound (pbw) | Additive (pbw) | Solvent 1 (pbw) | Solvent 2 (pbw) | Solvent 3 (pbw) |
|---|---|---|---|---|---|---|---|
| 34 | Polymer 10 (40)<br>Polymer 23 (40) | PAG-1<br>(5.0) | Q-1<br>(5.0) | — | PGMEA<br>(1,080) | EL<br>(1,080) | PGME<br>(1,440) |
| 35 | Polymer 11 (40)<br>Polymer 24 (40) | PAG-1<br>(5.0) | Q-1<br>(5.0) | — | PGMEA<br>(1,080) | EL<br>(1,080) | PGME<br>(1,440) |
| 36 | Polymer 12 (40)<br>Polymer 24 (40) | PAG-1<br>(5.0) | Q-1<br>(5.0) | — | PGMEA<br>(1,080) | EL<br>(1,080) | PGME<br>(1,440) |
| 37 | Polymer 11 (40)<br>Polymer 22 (40) | PAG-1<br>(5.0) | Q-1<br>(5.0) | — | PGMEA<br>(1,080) | EL<br>(1,080) | PGME<br>(1,440) |
| 38 | Polymer 13 (40)<br>Polymer 15 (40) | PAG-1<br>(5.0) | Q-1<br>(5.0) | — | PGMEA<br>(1,080) | EL<br>(1,080) | PGME<br>(1,440) |
| 39 | Polymer 1 (80) | — | Q-1<br>(4.0) | FP-1<br>(3.0) | PGMEA<br>(1,080) | EL<br>(1,080) | PGME<br>(1,440) |
| 40 | Polymer 1 (40)<br>Polymer 15 (40) | — | Q-1<br>(4.0) | FP-1<br>(3.0) | PGMEA<br>(1,080) | EL<br>(1,080) | PGME<br>(1,440) |
| 41 | Polymer 1 (40)<br>Polymer 15 (40) | PAG-1<br>(5.0) | Q-1<br>(5.0) | FP-1<br>(3.0) | PGMEA<br>(1,080) | EL<br>(1,080) | PGME<br>(1,440) |

TABLE 9

| | | Resin (pbw) | PAG (pbw) | Basic compound (pbw) | Additive (pbw) | Solvent 1 (pbw) | Solvent 2 (pbw) | Solvent 3 (pbw) |
|---|---|---|---|---|---|---|---|---|
| Comparative Example | 1 | Comparative Polymer 1 (80) | — | Q-1 (5.0) | TMGU (8.0) | PGMEA (1,080) | EL (1,080) | PGME (1,440) |
| | 2 | Comparative Polymer 2 (80) | — | Q-1 (5.0) | TMGU (8.0) | PGMEA (1,080) | EL (1,080) | PGME (1,440) |
| | 3 | Comparative Polymer 1 (80) | PAG-1 (5.0) | Q-1 (5.0) | TMGU (8.0) | PGMEA (1,080) | EL (1,080) | PGME (1,440) |
| | 4 | Comparative Polymer 2 (80) | PAG-1 (5.0) | Q-1 (5.0) | TMGU (8.0) | PGMEA (1,080) | EL (1,080) | PGME (1,440) |
| | 5 | Comparative Polymer 3 (80) | PAG-1 (5.0) | Q-1 (5.0) | TMGU (8.0) | PGMEA (1,080) | EL (1,080) | PGME (1,440) |
| | 6 | Comparative Polymer 4 (80) | PAG-1 (5.0) | Q-1 (5.0) | TMGU (8.0) | PGMEA (1,080) | EL (1,080) | PGME (1,440) |
| | 7 | Polymer 1 (80) | — | Comparative Q-1 (2.0) | — | PGMEA (1,080) | EL (1,080) | PGME (1,440) |
| | 8 | Polymer 1 (80) | — | Comparative Q-2 (2.8) | — | PGMEA (1,080) | EL (1,080) | PGME (1,440) |
| | 9 | Polymer 1 (40)<br>Polymer 15 (40) | PAG-1 (5.0) | Comparative Q-1 (2.5) | — | PGMEA (1,080) | EL (1,080) | PGME (1,440) |
| | 10 | Polymer 1 (40)<br>Polymer 15 (40) | PAG-1 (5.0) | Comparative Q-2 (3.3) | — | PGMEA (1,080) | EL (1,080) | PGME (1,440) |
| | 11 | Polymer 1 (40)<br>Polymer 15 (40) | — | Comparative Q-1 (2.0) | — | PGMEA (1,080) | EL (1,080) | PGME (1,440) |
| | 12 | Polymer 1 (40)<br>Polymer 15 (40) | — | Comparative Q-2 (2.5) | — | PGMEA (1,080) | EL (1,080) | PGME (1,440) |
| | 13 | Polymer 15 (80) | PAG-1 (8.0) | Q-1 (5.0) | — | PGMEA (1,080) | EL (1,080) | PGME (1,440) |
| | 14 | Polymer 15 (80) | PAG-1 (8.0) | Q-2 (5.0) | — | PGMEA (1,080) | EL (1,080) | PGME (1,440) |

TABLE 10

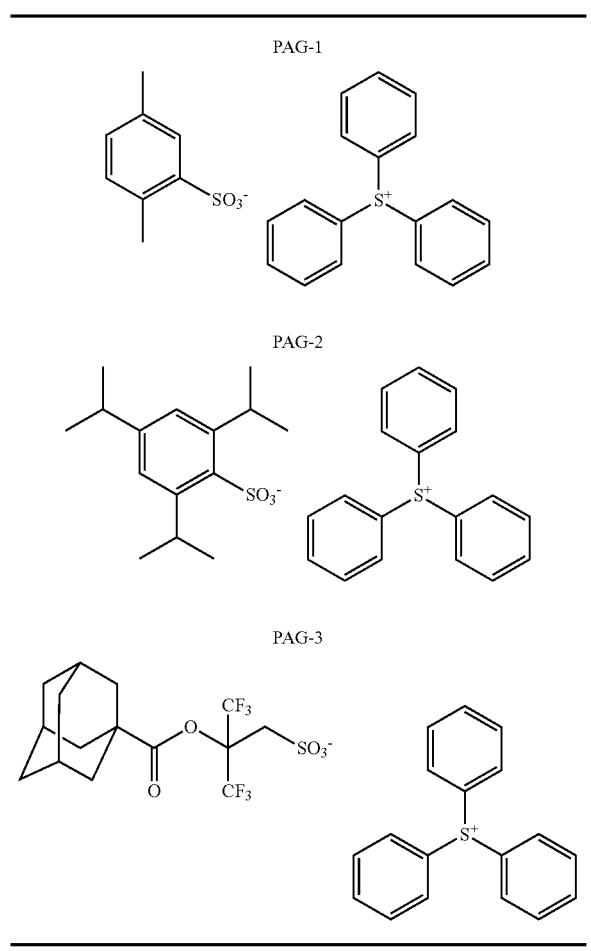

TABLE 11

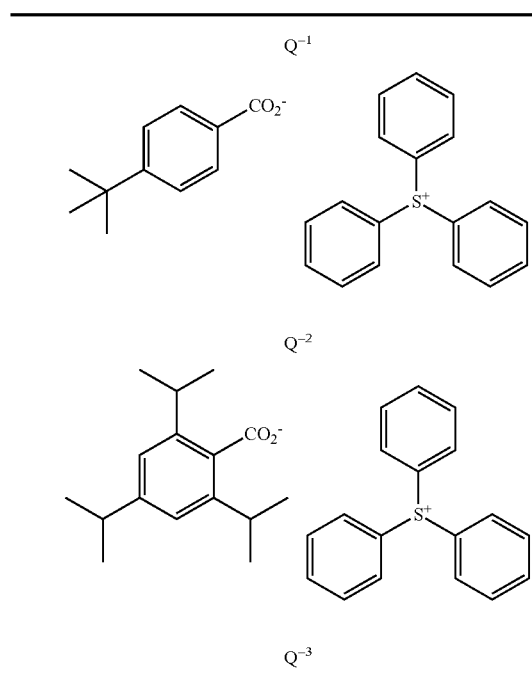

TABLE 11-continued

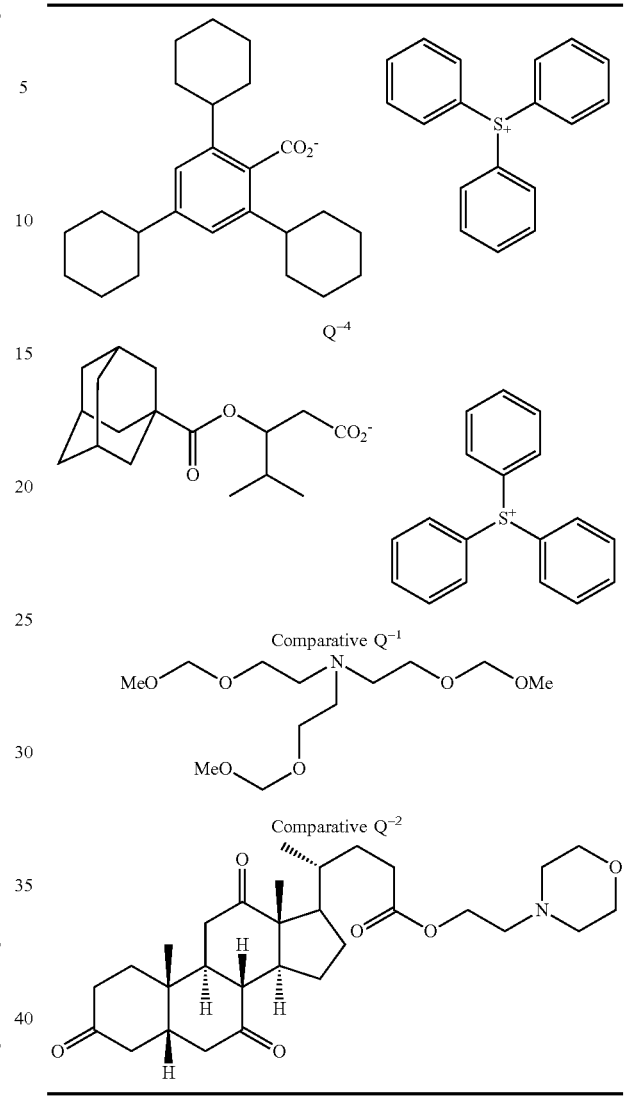

EB Image Writing Test (1) Evaluation of Resolution

Using a coater/developer system ACT-M (Tokyo Electron Ltd.), each of the negative resist compositions (Examples 1 to 41, Comparative Examples 1 to 14) was spin-coated onto a 152-mm square mask blank having a chromium oxynitride film at the outermost surface and pre-baked on a hot plate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 keV), then baked (PEB) at 130° C. for 600 seconds, and developed with a 2.38 wt % tetramethylammonium hydroxide aqueous solution, thereby yielding negative patterns.

The patterned blank was observed under a top-down scanning electron microscope (TDSEM). The optimum exposure (Eop) was defined as the exposure dose (μC/cm²) which provided a 1:1 resolution at the top and bottom of a 400-nm 1:1 line-and-space (LS) pattern. The maximum resolution of the resist was defined as the minimum line width that could be resolved at the exposure dose providing 1:1 resolution of a 400-nm line-and-space pattern. The LER of a 200-nm line-and-space pattern was measured under SEM. Tables 12 and 13 tabulate the results of the EB image writing test on the inventive and comparative resist compositions.

In conjunction with the results in Tables 12 and 13, the resolution of LS is a resolution of a 1:1 line-and-space pattern, IL is a resolution of one line in an isolated line pattern, and IS is a resolution of one space in an isolated space pattern.

TABLE 12

|  |  | Optimum dose of LS (μC/cm²) | Resolution of LS (nm) | Resolution of IL (nm) | Resolution of IS (nm) | LER (nm) |
|---|---|---|---|---|---|---|
| Example | 1 | 48 | 40 | 40 | 40 | 4.5 |
|  | 2 | 49 | 40 | 40 | 45 | 4.9 |
|  | 3 | 51 | 40 | 45 | 40 | 4.9 |
|  | 4 | 47 | 40 | 40 | 40 | 4.8 |
|  | 5 | 46 | 45 | 40 | 40 | 4.7 |
|  | 6 | 48 | 40 | 40 | 45 | 4.6 |
|  | 7 | 49 | 40 | 40 | 40 | 4.7 |
|  | 8 | 50 | 40 | 45 | 40 | 4.6 |
|  | 9 | 51 | 40 | 40 | 45 | 4.7 |
|  | 10 | 50 | 40 | 40 | 40 | 4.8 |
|  | 11 | 50 | 40 | 40 | 40 | 4.5 |
|  | 12 | 49 | 40 | 40 | 40 | 4.8 |
|  | 13 | 49 | 45 | 45 | 40 | 4.8 |
|  | 14 | 47 | 40 | 40 | 40 | 4.7 |
|  | 15 | 48 | 40 | 45 | 40 | 4.6 |
|  | 16 | 47 | 40 | 40 | 45 | 5.0 |
|  | 17 | 48 | 40 | 40 | 40 | 4.6 |
|  | 18 | 48 | 45 | 45 | 40 | 4.8 |
|  | 19 | 48 | 40 | 40 | 40 | 5.0 |
|  | 20 | 49 | 45 | 40 | 40 | 4.8 |
|  | 21 | 47 | 40 | 40 | 45 | 4.9 |
|  | 22 | 51 | 40 | 40 | 40 | 4.9 |
|  | 23 | 50 | 40 | 45 | 40 | 4.7 |
|  | 24 | 50 | 45 | 40 | 40 | 4.9 |
|  | 25 | 49 | 40 | 40 | 40 | 4.6 |
|  | 26 | 49 | 40 | 45 | 40 | 4.6 |
|  | 27 | 48 | 40 | 40 | 45 | 4.5 |
|  | 28 | 50 | 40 | 45 | 40 | 4.6 |
|  | 29 | 50 | 40 | 40 | 40 | 4.8 |
|  | 30 | 48 | 45 | 40 | 40 | 4.7 |
|  | 31 | 47 | 40 | 45 | 40 | 4.8 |
|  | 32 | 48 | 40 | 40 | 40 | 4.7 |
|  | 33 | 49 | 40 | 45 | 40 | 4.8 |
|  | 34 | 51 | 40 | 40 | 40 | 4.9 |
|  | 35 | 50 | 40 | 40 | 40 | 4.7 |
|  | 36 | 49 | 40 | 40 | 40 | 4.9 |
|  | 37 | 49 | 40 | 40 | 40 | 4.8 |
|  | 38 | 49 | 40 | 40 | 40 | 4.7 |
|  | 39 | 48 | 40 | 40 | 40 | 4.6 |
|  | 40 | 47 | 40 | 40 | 45 | 4.5 |
|  | 41 | 51 | 40 | 40 | 40 | 4.7 |

TABLE 13

|  |  | Optimum dose of LS (μC/cm²) | Resolution of LS (nm) | Resolution of IL (nm) | Resolution of IS (nm) | LER (nm) |
|---|---|---|---|---|---|---|
| Comparative Example | 1 | 48 | 55 | 60 | 65 | 6.1 |
|  | 2 | 49 | 55 | 60 | 55 | 6.3 |
|  | 3 | 47 | 60 | 55 | 60 | 6.4 |
|  | 4 | 53 | 55 | 60 | 60 | 6.8 |
|  | 5 | 50 | 55 | 55 | 60 | 6.2 |
|  | 6 | 49 | 60 | 60 | 55 | 6.6 |
|  | 7 | 48 | 50 | 45 | 50 | 5.3 |
|  | 8 | 49 | 50 | 55 | 50 | 7.1 |
|  | 9 | 51 | 45 | 45 | 45 | 5.6 |
|  | 10 | 50 | 45 | 45 | 45 | 7.1 |
|  | 11 | 50 | 45 | 45 | 45 | 5.4 |
|  | 12 | 52 | 45 | 45 | 45 | 6.9 |
|  | 13 | 51 | 50 | 50 | 50 | 5.8 |
|  | 14 | 51 | 50 | 50 | 50 | 5.7 |

(2) Dependence on Prebake Temperature

Exposure and development were carried out by the same procedure as in (1) evaluation of resolution except that the prebake temperature after spin coating was changed from 110° C. to 100° C. An exposure dose (μC/cm²) capable of resolving a 400-nm 1:1 LS pattern was determined. This dose is designated $E_{100}$. Next, exposure and development were carried out by the same procedure as in (1) evaluation of resolution except that the prebake temperature after spin coating was changed from 110° C. to 120° C. and the dose was set equal to $E_{100}$. Provided that the design pattern had a line width of 400 nm, an actual size was measured and reported as $W_{120}$. The dependence of line width on prebake temperature was computed according to the following equation.

Dependence on prebake temperature=$(W_{120}-400)/20$

The value indicates how the pattern line width varies with a change of prebake temperature, with a smaller value indicating less dependence on prebake temperature. The results are shown in Table 14.

TABLE 14

|  |  | Dependence on prebake temperature |
|---|---|---|
| Example | 1 | 0.10 nm/° C. |
|  | 21 | 0.10 nm/° C. |
|  | 22 | 0.15 nm/° C. |
| Comparative Example | 7 | 0.65 nm/° C. |
|  | 9 | 0.72 nm/° C. |
|  | 11 | 0.71 nm/° C. |

(3) Dependence on PEB Temperature

The optimum dose in (1) evaluation of resolution is designated $E_{130}$. Exposure and development were carried out by the same procedure as in (1) evaluation of resolution except that the PEB temperature was changed from 130° C. to 150° C. and the dose was set equal to $E_{130}$. Provided that the design pattern had a line width of 400 nm, an actual size was measured and reported as $W_{150}$. The dependence of line width on PEB temperature was computed according to the following equation.

Dependence on PEB temperature=$(W_{150}-400)/20$

The value indicates how the pattern line width varies with a change of PEB temperature, with a smaller value indicating less dependence on PEB temperature. The results are shown in Table 15.

TABLE 15

|  |  | Dependence on PEB temperature |
|---|---|---|
| Example | 1 | 0.20 nm/° C. |
|  | 21 | 0.15 nm/° C. |
|  | 22 | 0.15 nm/° C. |
| Comparative | 7 | 2.10 nm/° C. |
| Example | 9 | 2.30 nm/° C. |
|  | 11 | 2.05 nm/° C. |

(4) Evaluation of Chemical Flare Resistance

A resist film was formed under the same conditions as in (1) evaluation of resolution, exposed in a setup designed to form a space of 1 μm squares at the center of a negative pattern of 1 cm squares, and developed. The resist film was rated OK when a space of 1 μm squares was formed, and NG when not formed. The results are shown in Table 16.

TABLE 16

|  |  | Chemical flare resistance (formation of 1-μm square space at the center) |
|---|---|---|
| Example | 1 | OK |
|  | 21 | OK |
|  | 22 | OK |
| Comparative | 7 | NG (not formed because of negative working) |
| Example | 9 | NG (not formed because of negative working) |
|  | 11 | NG (not formed because of negative working) |

(5) Evaluation of Post-Coating Delay (PCD)

A resist film was exposed immediately after its formation (or coating) in a dose capable of resolution of a 400-nm line-and-space pattern. Also a resist film was exposed after 2 weeks from its formation (or coating) in the same dose as the initial. A difference in line width between these patterns was determined. A line width variation per month was reported as PCD. A smaller value of PCD indicates better storage stability of resist film after coating. The results are shown in Table 17.

TABLE 17

|  |  | PCD |
|---|---|---|
| Example | 1 | <1.0 nm/1 month |
|  | 21 | <1.0 nm/1 month |
|  | 22 | <1.0 nm/1 month |
| Comparative | 7 | 2.2 nm/1 month |
| Example | 9 | 2.1 nm/1 month |
|  | 11 | 1.9 nm/1 month |

The results in Tables 12 to 17 are interpreted as follow. All the inventive resist compositions showed satisfactory values of resolution and LER. The resist compositions of Comparative Examples 1 to 6 containing a crosslinker and the resist compositions of Comparative Examples 13 and 14 containing a polymer free of acid-generating units were inferior in resolution.

The resist compositions of Comparative Examples 7, 9 and 11 containing an amine compound as the basic compound showed unsatisfactory values of resolution and LER, strong temperature dependence, low chemical flare resistance, and poor stability of resist film after coating. If is believed that the temperature dependence becomes stronger because as the bake temperature elevates, the basic compound volatilizes off and thus the line width becomes thicker despite an identical exposure dose. It is also believed that the stability of resist film after coating becomes poorer because the basic compound gradually volatilizes during storage.

It is believed that the chemical flare resistance becomes poorer because the acid generated in the image region volatilizes without, being trapped by the amine compound in the image region, and re-deposits on the unexposed region where unwanted negative tone working takes place. As a result, the space pattern is not formed. In the inventive negative resist composition using a carboxylic acid salt as the basic compound, the volatilization of the basic compound from the image region does not occur, which accounts for the mitigation of temperature dependence of a pattern and satisfactory results in the evaluation of chemical flare resistance.

It is contemplated that improvements in temperature dependence, storage stability and chemical flare resistance may be achieved by an approach of using a basic compound having a high boiling point as in Comparative Examples 8, 10 and 12, but the pattern formed by this approach has increased LER.

(6) Evaluation of EB Exposure of Resist Film Covered with Anti-Charging Film

Reference Examples 1 to 6

When a resist film is subjected to EB pattern writing at a current quantity of at least 50 A, especially a high current quantity of at least 0.200 A, it sometimes occurs that pattern writing at a high positional accuracy is inhibited because the orbit of EB is deflected by the electrostatic repulsion due to charging of the resist film. To solve this problem, an anti-charging film is formed on top of the resist film before pattern writing is carried out.

A resist film was formed under the same conditions as in (1) evaluation of resolution. Using a coater/developer system ACT-M (Tokyo Electron Ltd.), a conductive polymer composition was spin-coated over the resist film and pre-baked on a hot plate at 90° C. for 600 seconds to form a anti-charging film of 60 nm thick. The conductive polymer composition used herein was a water dispersion of polystyrene-doped polyaniline as described in Proc. SPIE Vol. 8522, 852200-1. The photomask blank having the resist film and anti-charging film thereon was exposed to electron beam using an EB writer system EBM-5000Plus (NuFlare Technology Inc., accelerating voltage 50 keV), then baked (PEB) at 130° C. for 600 seconds, and developed in a 2.38 wt % TMAH aqueous solution, thereby yielding a negative pattern.

The resist film, anti-charging film and the resulting resist pattern were evaluated as follows.
[Optimum Dose and Maximum Resolution]
Evaluated as in (1) evaluation of resolution
[Surface Resistivity]
The resist film and anti-charging film were measured for surface resistivity by a resistivity meter Hiresta UP MCP-HT450 (Mitsubishi Chemical Co., Ltd.).

[Change of Sensitivity]

The resist films of Reference Examples 1 to 6 were measured for sensitivity. It was compared with the sensitivity of Examples 1, 21, 22, 39, 40 and 41, from which a deviation (%) was computed.

[Pattern Profile]

The resist film pattern was sectioned and observed under SEM. A profile was judged by visual observation of a SEM image of the section.

[Post-Coating Delay (PCD)]

A resist film was exposed immediately after the formation of anti-charging film in a dose capable of resolution of a 400-nm line-and-space pattern. Also a resist film was exposed after 2 weeks from the formation of anti-charging film in the same dose as the initial. A difference in line width between these patterns was determined. A line width variation per day was reported as PCD.

The results are shown in Table 18.

TABLE 18

| | | Resist composition | Optimum dose ($\mu C/cm^2$) | Maximum resolution (nm) | Surface resistivity ($\Omega/\square$) | Sensitivity change | Pattern profile | PCD (nm/day) |
|---|---|---|---|---|---|---|---|---|
| Reference Example | 1 | Example 1 | 41 | 50 | $3.1 \times 10^8$ | −14.58% | inversely tapered | 0.29 |
| | 2 | Example 21 | 43 | 50 | $3.3 \times 10^8$ | −8.51% | inversely tapered | 0.34 |
| | 3 | Example 22 | 47 | 50 | $3.2 \times 10^8$ | −7.84% | inversely tapered | 0.48 |
| | 4 | Example 39 | 47 | 40 | $3.2 \times 10^8$ | −2.08% | rectangular | 0.07 |
| | 5 | Example 40 | 46 | 40 | $3.3 \times 10^8$ | −2.13% | rectangular | 0.07 |
| | 6 | Example 41 | 50 | 40 | $3.2 \times 10^8$ | −1.96% | rectangular | 0.07 |

In Reference Examples 1 to 3 using resist compositions not containing the fluorine-containing resin, the acid component in the anti-charging film composition penetrated into the resist film, resulting in a substantial change of sensitivity, a pattern of inversely tapered profile, and an increased value of PCD. In contrast, Reference Examples 4 to 6 using resist compositions containing the fluorine-containing resin showed a little change of sensitivity, a pattern of rectangular profile, and an acceptable value of PCD. The difference in surface resistivity among Reference Examples 1 to 6 was of no significance, indicating that patterns could be written at a high positional accuracy. The foregoing results demonstrate that when image writing is carried out after the anti-charging film is formed on the resist film, the resist film is preferably formed of a resist composition containing a fluorine-containing resin.

It has been demonstrated that the negative resist composition of the invention is used to form a pattern having a high resolution, minimal LER, and mitigated temperature dependence of feature size. Due to these advantages, the negative resist composition is suited for the fabrication of microelectronic devices and especially the processing of photomask blanks by high current flow photolithography.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application Nos. 2015-078433 and 2015-078904 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A negative resist composition comprising (A) a polymer comprising recurring units having the general formula (1), recurring units of at least one type selected from units having the general formulae (a1), (a2), and (a3), and recurring units of at least one type selected from units having the general formulae (2) and (3):

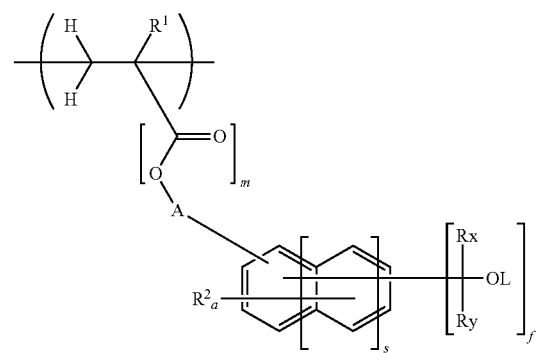

(1)

wherein A is a single bond or a $C_1$-$C_{10}$ alkylene group which may contain an ethereal oxygen atom at an intermediate of the chain, $R^1$ is hydrogen, fluorine, methyl or trifluoromethyl, $R^2$ is hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, L is hydrogen, a monovalent, straight, branched or cyclic, aliphatic $C_1$-$C_{10}$ hydrocarbon group which may contain an ethereal oxygen atom, carbonyl moiety or carbonyloxy moiety at an intermediate of the chain, or an optionally substituted monovalent aromatic group, Rx and Ry each are hydrogen, a $C_1$-$C_{15}$ alkyl group which may be substituted with hydroxy or alkoxy, or an optionally substituted monovalent aromatic group, Rx and Ry may bond together to form a ring with the carbon atom to which they are attached, excluding the case where Rx and Ry are hydrogen at the same time, f is an integer of 1 to 3, s is an integer of 0 to 2, a is an integer (5+2s-f), and m is 0 or 1,

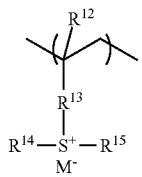
(a1)

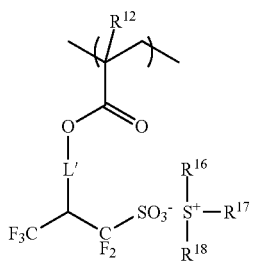
(a2)

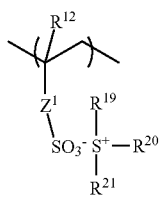
(a3)

wherein $R^{12}$ is each independently hydrogen or methyl, $R^{13}$ is a single bond, phenylene group, —O—$R^{22}$—, or —C(=O)—$Z^2$—$R^{22}$—, $Z^2$ is oxygen or NH, $R^{22}$ is a straight, branched or cyclic $C_1$-$C_6$ alkylene, alkenylene or phenylene group which may contain a carbonyl (—CO—), ester (—COO—), ether (—O—) or hydroxyl moiety, L' is a single bond or —$Z^3$—C(=O)—O—, $Z^3$ is a straight, branched or cyclic divalent $C_1$-$C_{20}$ hydrocarbon group which may be substituted with a heteroatom, $Z^1$ is a single bond, methylene, ethylene, phenylene, fluorinated phenylene, —O—$R^{23}$—, or —C(=O)—$Z^4$—$R^{23}$—, $Z^4$ is oxygen or NH, $R^{23}$ is a straight, branched or cyclic $C_1$-$C_6$ alkylene, alkenylene or phenylene group which may contain a carbonyl, ester, ether or hydroxyl moiety, $M^-$ is a non-nucleophilic counter ion $R^{14}$, $R^{15}$, $R^{16}$, $R^{17}$, $R^{18}$, $R^{19}$, $R^{20}$, and $R^{21}$ are each independently a straight $C_1$-$C_{20}$, branched or cyclic $C_3$-$C_{20}$ monovalent hydrocarbon group in which at least one hydrogen atom may be replaced by a heteroatom selected from oxygen, sulfur, nitrogen and halogen, or in which a heteroatom selected from oxygen, sulfur and nitrogen may intervene, so that a hydroxyl group, cyano group, carbonyl group, ether bond, ester bond, sulfonic acid ester bond, carbonate bond, lactone ring, sultone ring, carboxylic anhydride, or haloalkyl group may form or intervene, or $R^{14}$ and $R^{15}$ may bond together to form a ring with the sulfur atom, or any two or more of $R^{16}$, $R^{17}$ and $R^{18}$ or any two or more of $R^{19}$, $R^{20}$ and $R^{21}$ may bond together to form a ring with the sulfur atom,

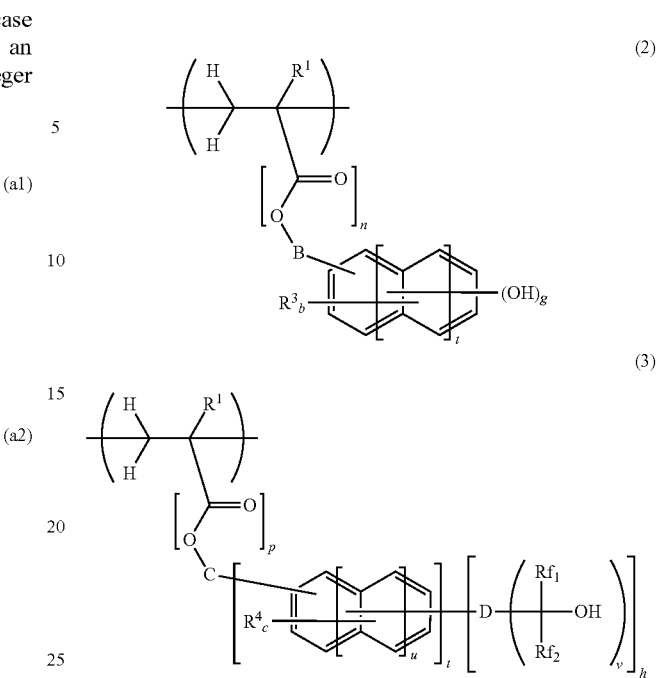

wherein B and C each are a single bond or a $C_1$-$C_{10}$ alkylene group which may contain an ethereal oxygen atom at an intermediate of the chain, D is a single bond or a (v+1)-valent, straight, branched or cyclic, aliphatic $C_1$-$C_{10}$ hydrocarbon group which may be substituted with fluorine and which may contain an ethereal oxygen atom, carbonyl moiety or carbonyloxy moiety at an intermediate of the chain, $R^1$ is hydrogen, fluorine, methyl, or trifluoromethyl, $R^3$ and $R^4$ are each independently hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, $Rf_1$ and $Rf_2$ each are a $C_1$-$C_6$ alkyl group having at least one fluorine, $Rf_1$ may bond with D to form a ring with the carbon atom to which they are attached, g is an integer of 0 to 3, h is 1 or 2, r is 0 or 1, v is 1 or 2, t and u each are an integer of 0 to 2, b is an integer (5+2t-g), c is an integer (5+2u-h), n and p are each independently 0 or 1, with the proviso that p is 1 when r is 0, (B) an acid diffusion regulator comprising a salt having the general formula (3a):

$$R^{11}-CO_2^-M^+ \quad (3a)$$

wherein $R^{11}$ is a straight, branched or cyclic $C_1$-$C_{20}$ alkyl group, $C_2$-$C_{20}$ alkenyl group or $C_6$-$C_{20}$ aryl group, which may contain fluorine, nitrogen, ether moiety, ester moiety, lactone ring, lactam ring, carbonyl moiety, or hydroxyl moiety, and M is a substituent-bearing counter cation selected from sulfonium, iodonium and ammonium cations, and (C) an additional polymer comprising recurring units having the general formula (1), but free of recurring units having a site capable of generating an acid upon exposure to high-energy radiation.

2. The negative resist composition of claim 1 wherein the polymer (A) further comprises recurring units of at least one type selected from units having the general formulae (4) and (5):

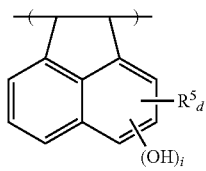
(4)

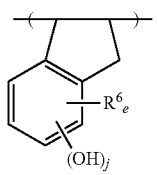
(5)

wherein $R^5$ and $R^6$ are each independently hydrogen, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, i and j each are an integer of 0 to 3, d is an integer of 0 to 5, and e is an integer of 0 to 3.

3. The negative resist composition of claim 1, further comprising a compound capable of generating an acid upon exposure to high-energy radiation.

4. The negative resist composition of claim 3 wherein the compound capable of generating an acid upon exposure to high-energy radiation is a compound comprising an anion selected from the group consisting of the following formulae:

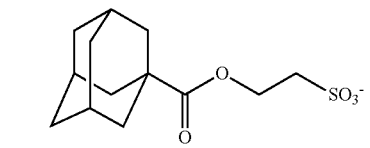

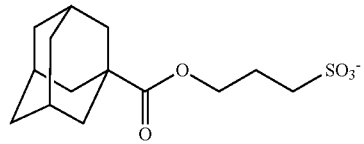

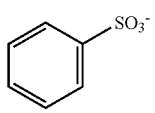

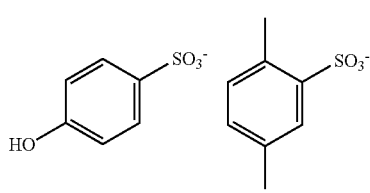

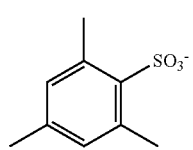

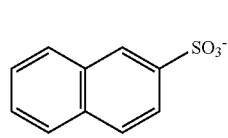

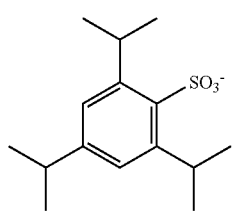

-continued

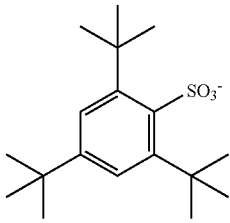

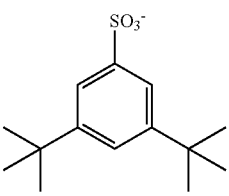

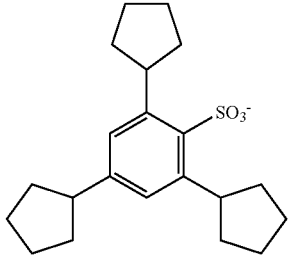

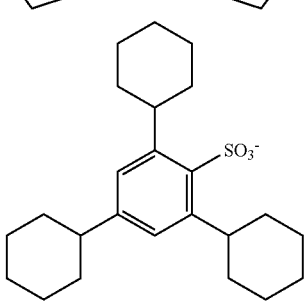

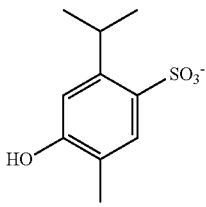

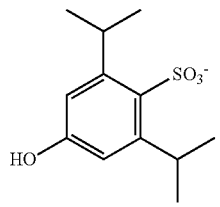

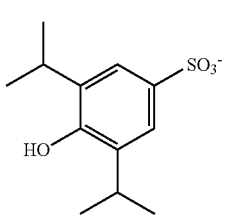

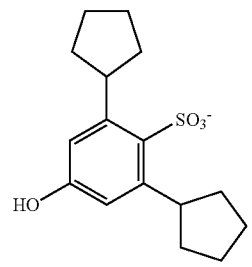

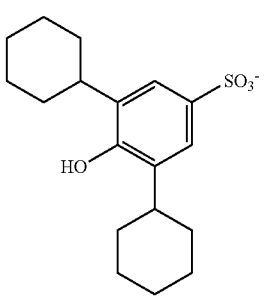

85
-continued
86
-continued
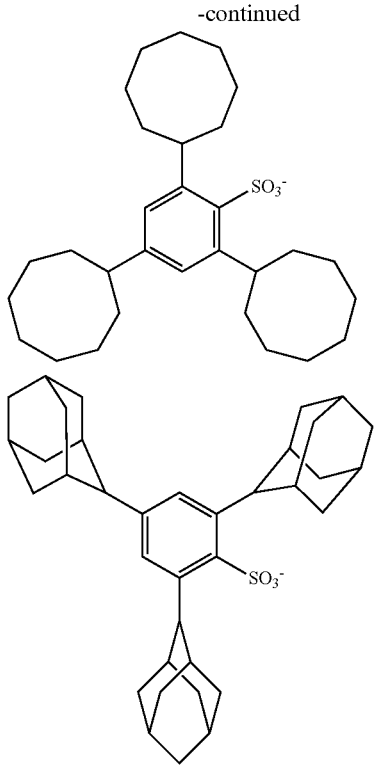
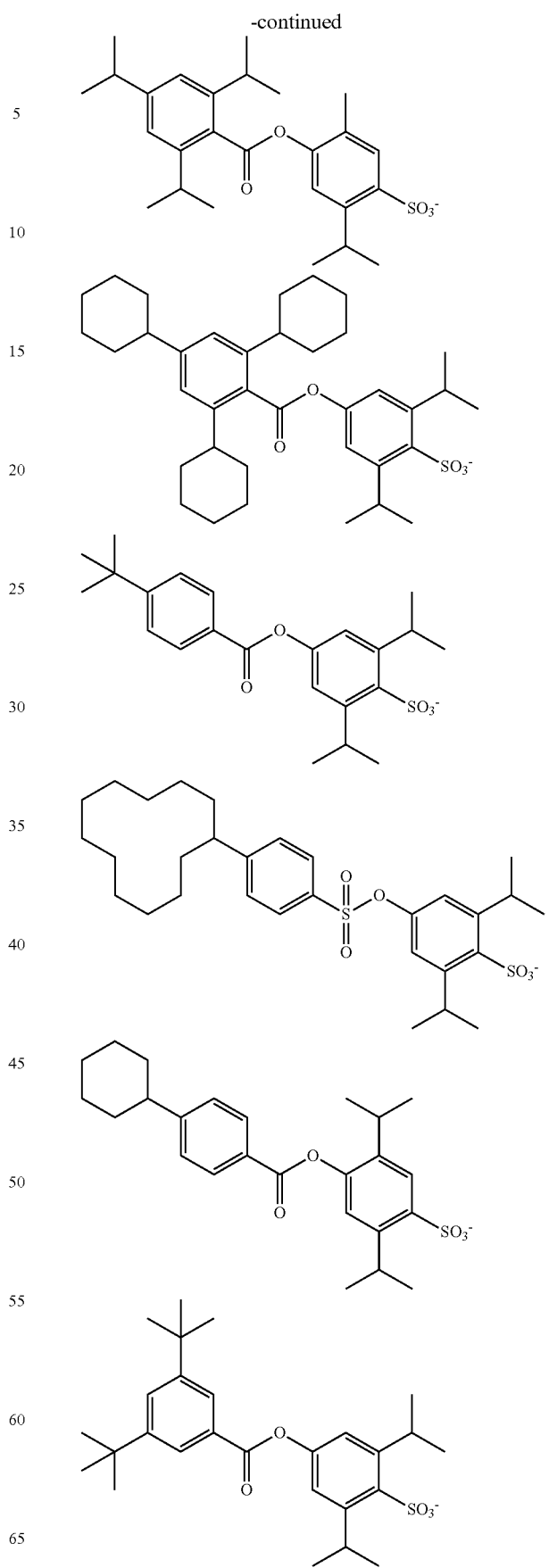

87
-continued
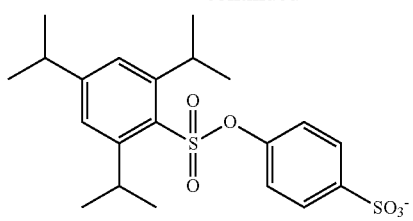
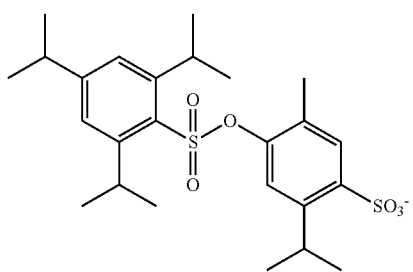
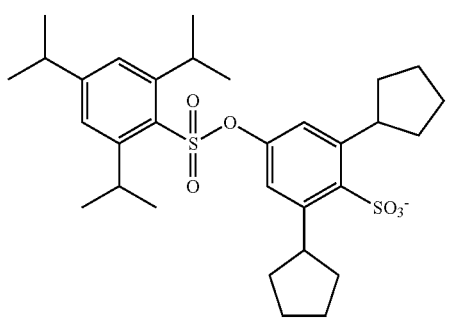
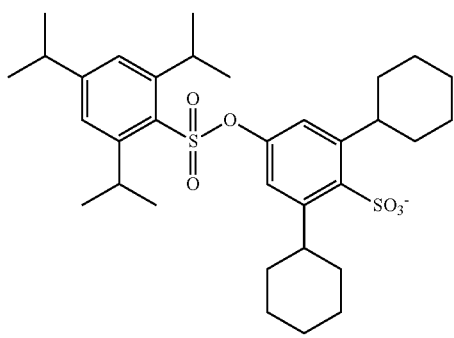
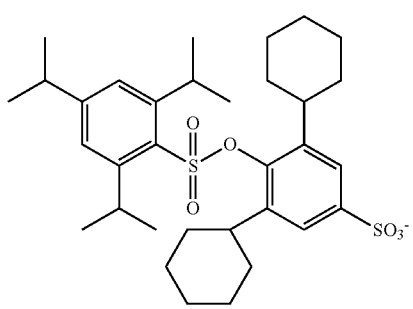
88
-continued
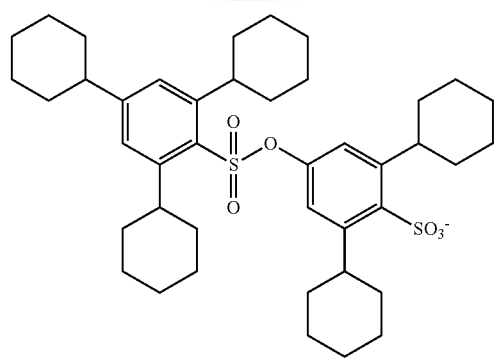
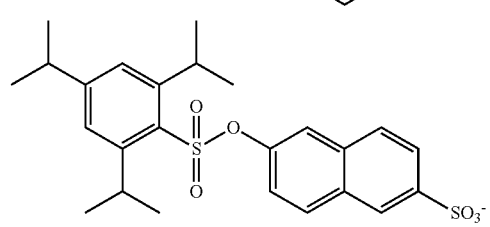
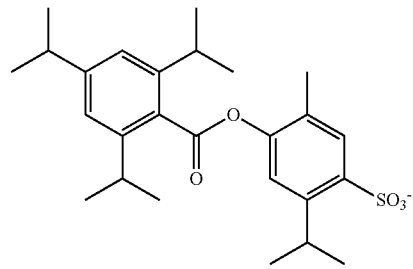
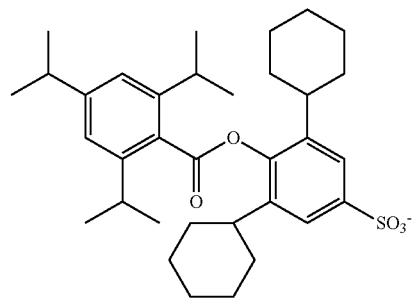
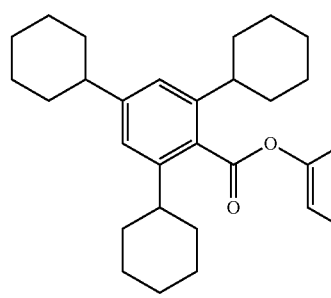
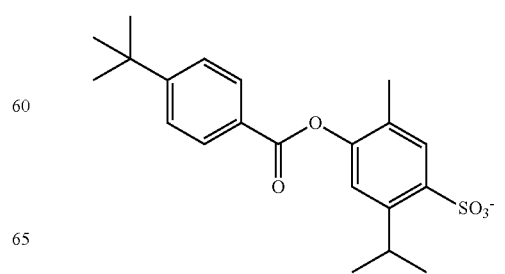

89
-continued
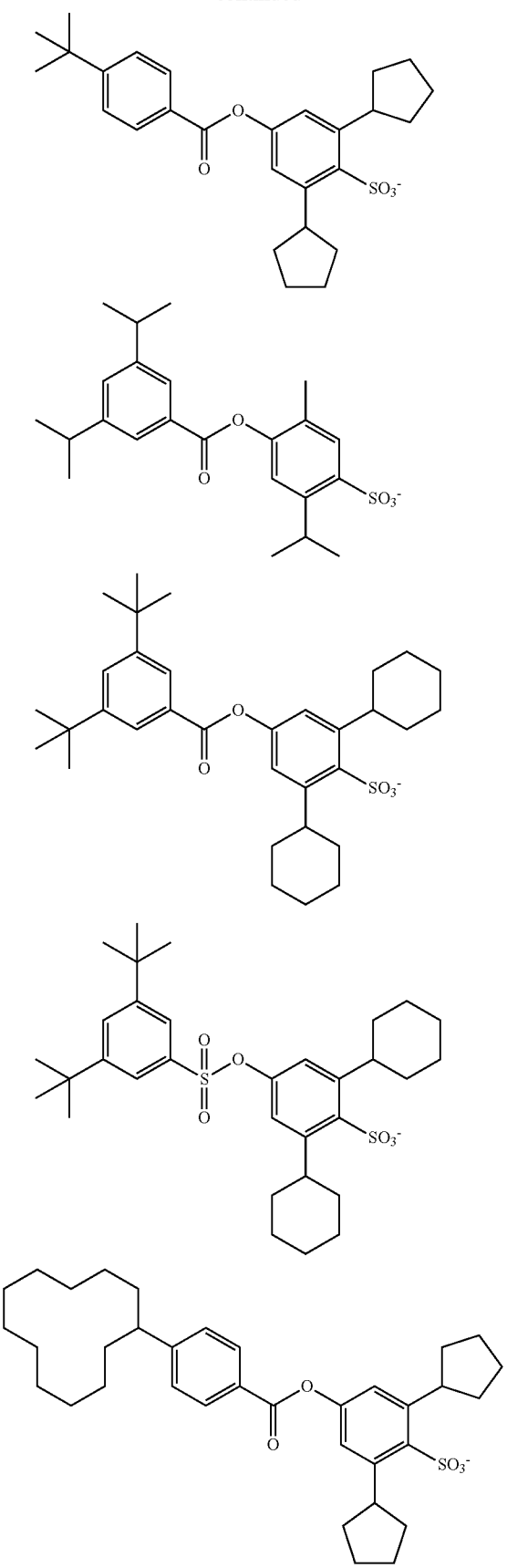
90
-continued
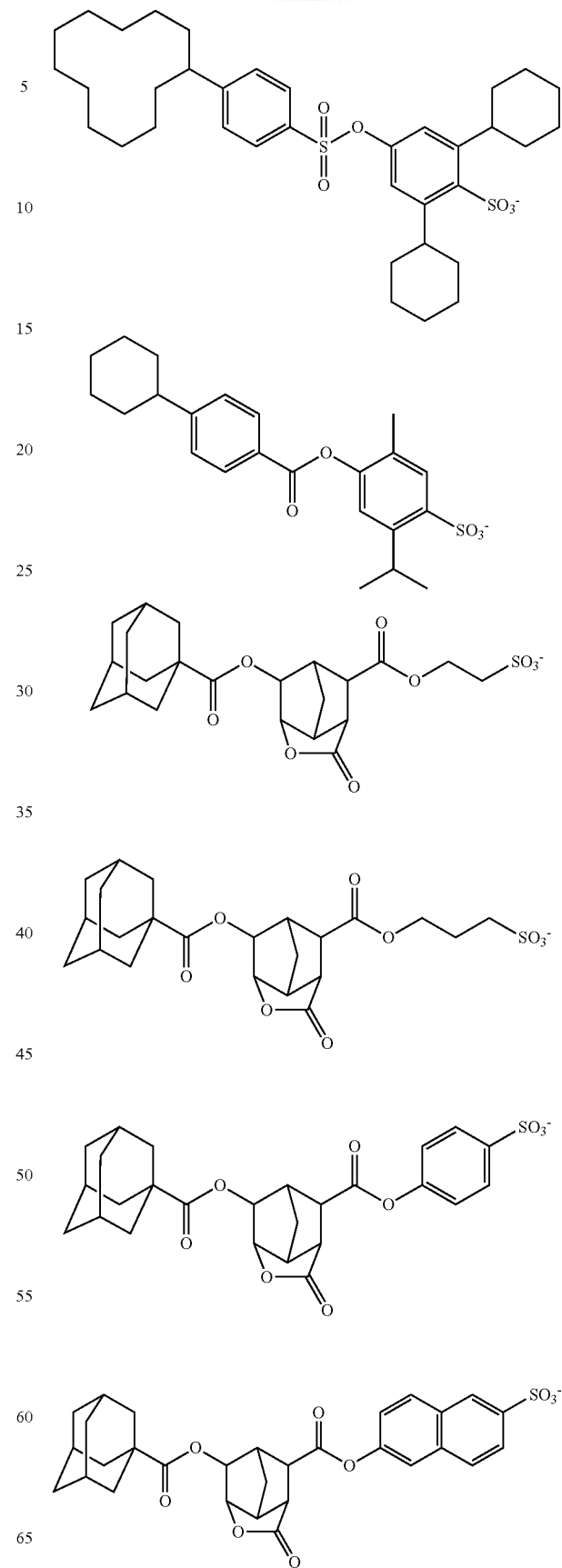

91
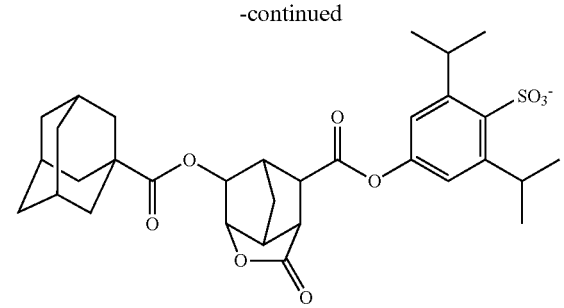
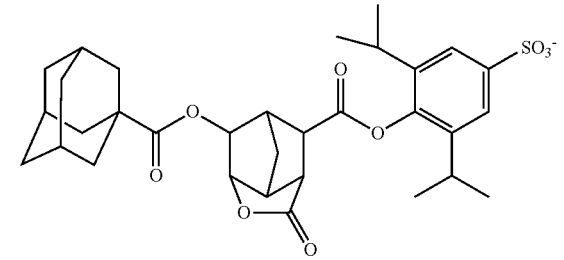
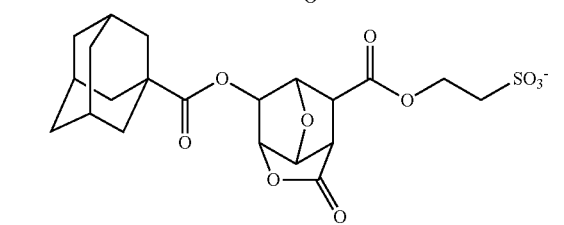
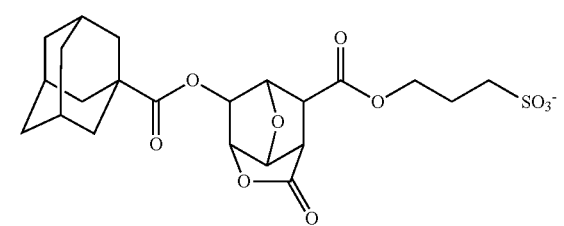
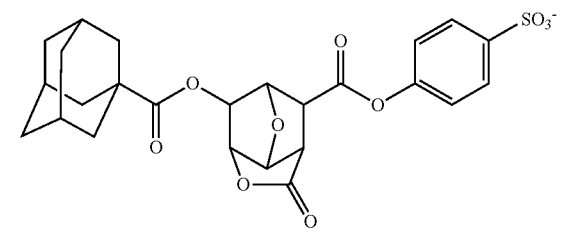
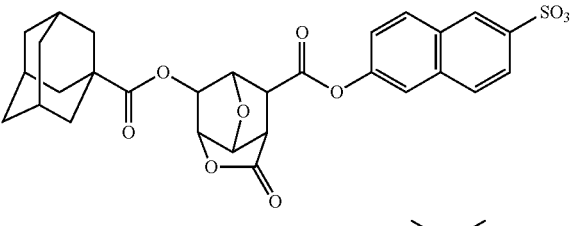
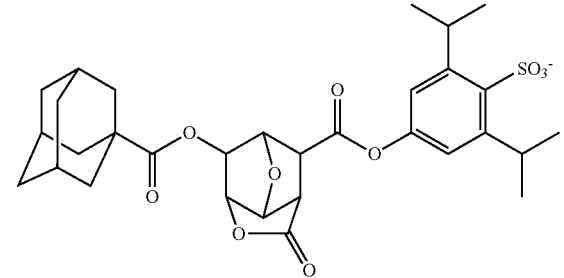
92
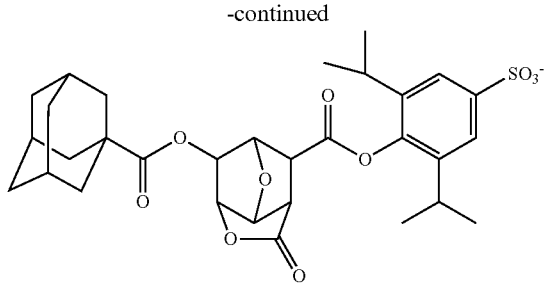
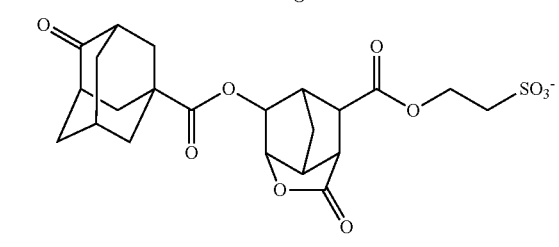
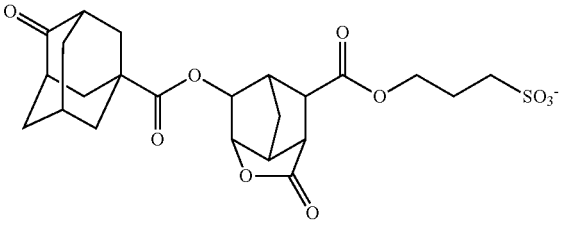
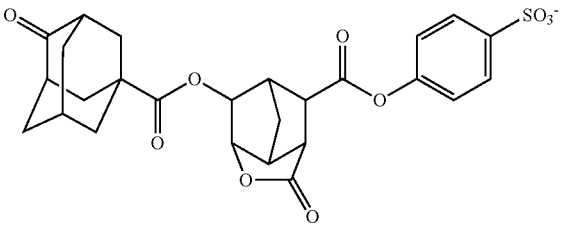
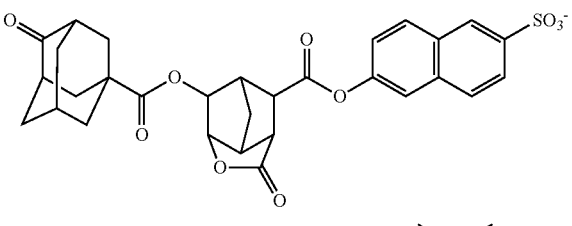
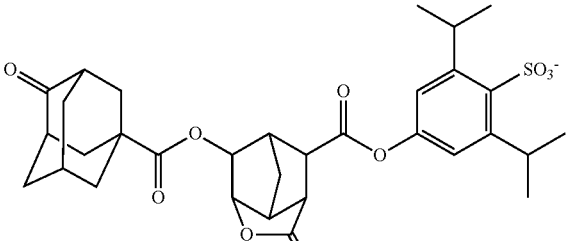
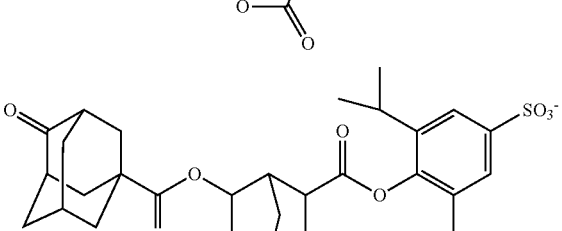
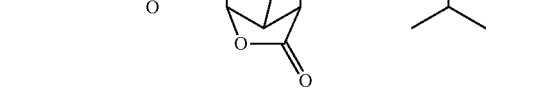

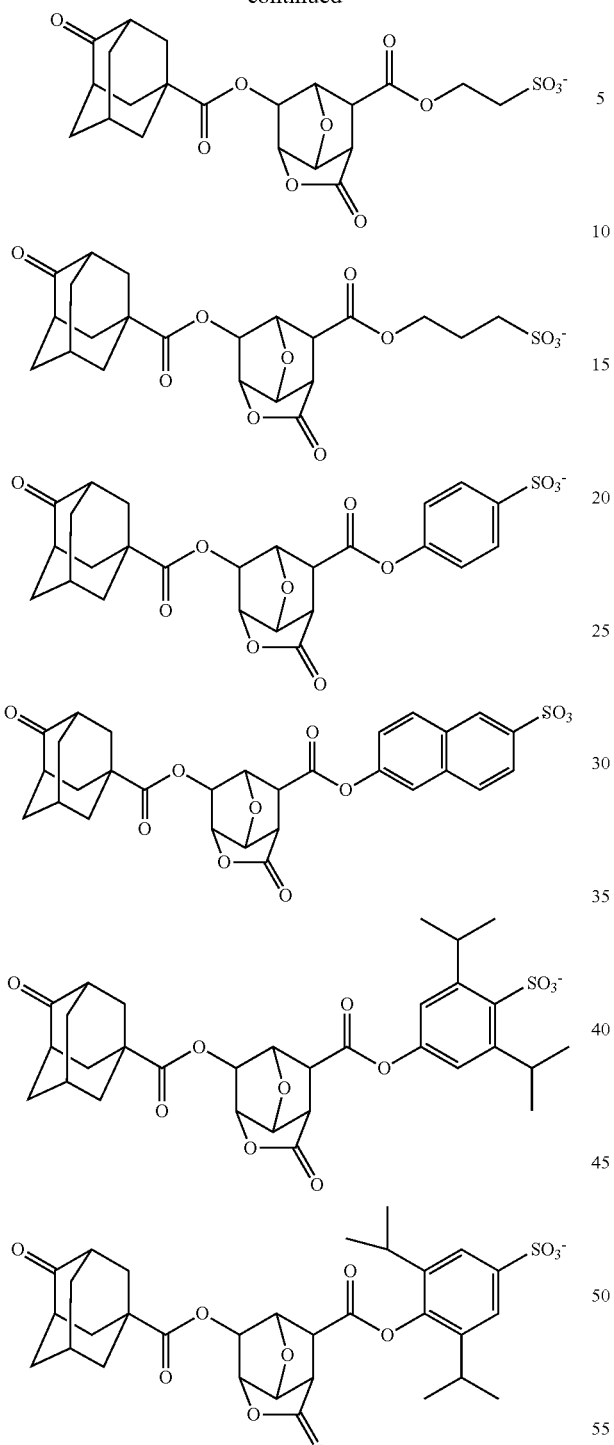
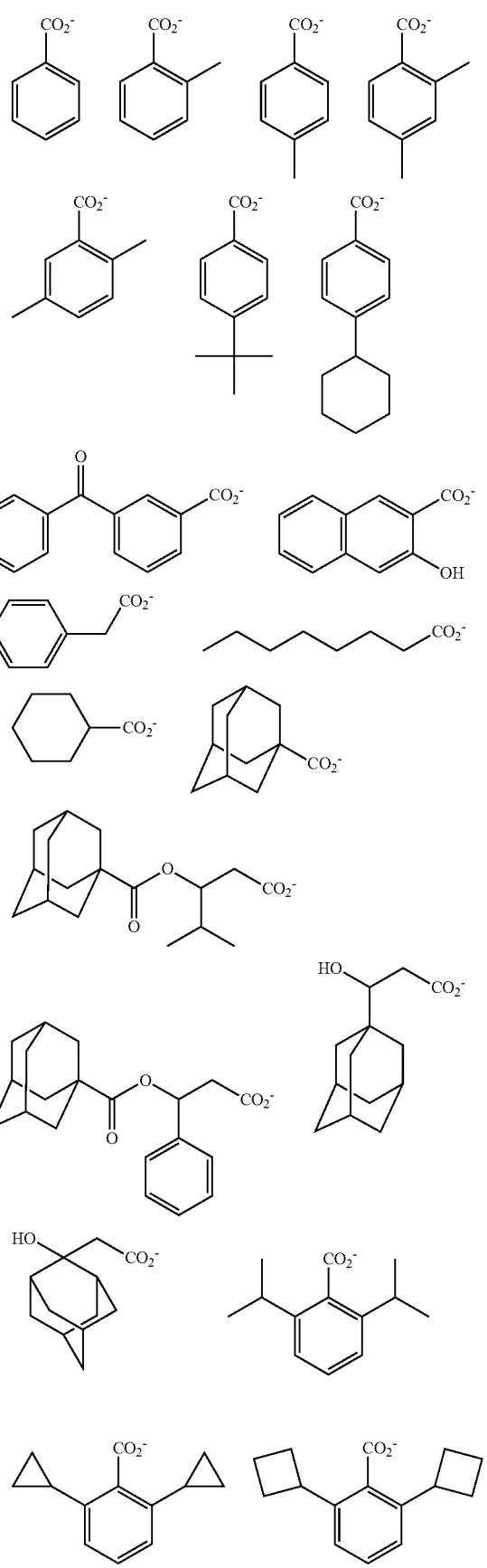
5. The negative resist composition of claim 1 wherein the acid diffusion regulator (B) consists of the salt having the general formula (3a).
6. The negative resist composition of claim 1 wherein the anion moiety in the salt of formula (3a) is selected from the group consisting of the following formulae:

95
-continued
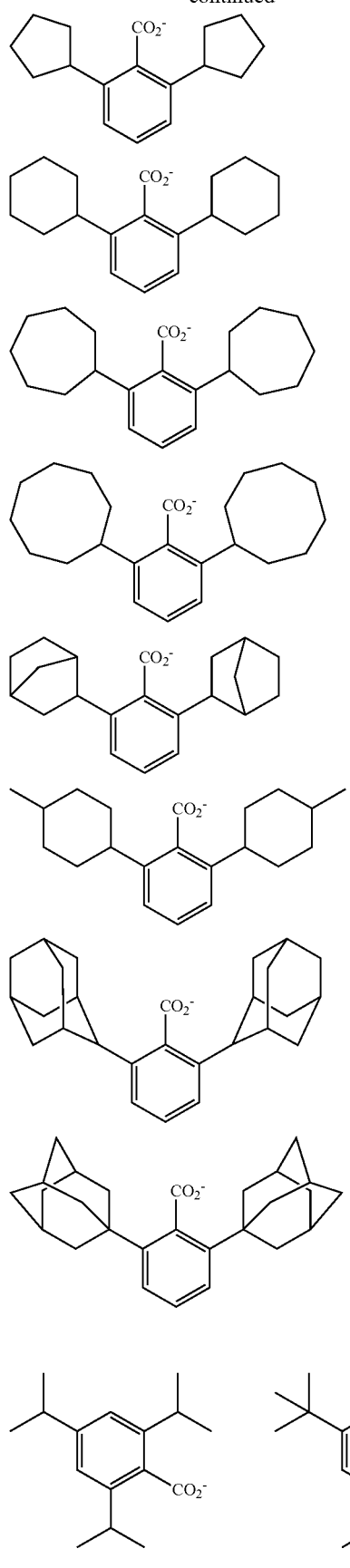
96
-continued
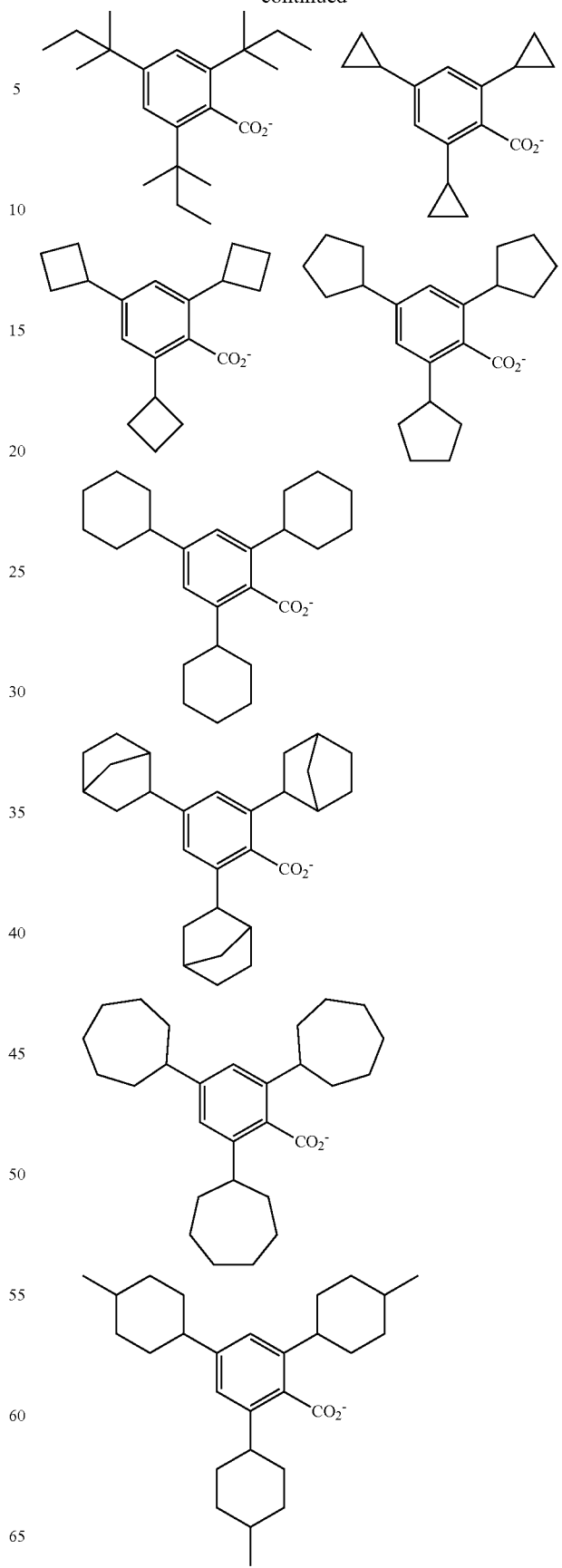

-continued

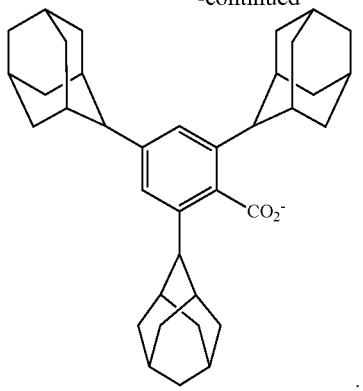

7. A photomask blank coated with the negative resist composition of claim 1.

8. A pattern forming process comprising the steps of applying the negative resist composition of claim 1 onto a processable substrate to form a resist film thereon, exposing patternwise the resist film to high-energy radiation, and developing the resist film in an alkaline developer to form a resist pattern.

9. The pattern forming process of claim 8 wherein the high-energy radiation is EUV or EB.

10. The pattern forming process of claim 8 wherein the processable substrate is a photomask blank.

11. The pattern forming process of claim 10 wherein the photomask blank has an outermost surface formed of a chromium based material.

* * * * *